United States Patent
Ferrer Montiel et al.

(10) Patent No.: US 9,333,152 B2
(45) Date of Patent: May 10, 2016

(54) PEPTIDES WHICH INHIBIT ACTIVATED RECEPTORS AND THEIR USE IN COSMETIC OR PHARMACEUTICAL COMPOSITIONS

(71) Applicant: LIPOTEC, S.A., Gava (ES)

(72) Inventors: Antonio Vicente Ferrer Montiel, Alicante (ES); José María García Antón, Barcelona (ES); Raquel Delgado González, Gava (ES)

(73) Assignee: Lipotec, S.A., Gava, Barcelona (ES)

( * ) Notice: Subject to any disclaimer, the term of this patent is extended or adjusted under 35 U.S.C. 154(b) by 0 days.

(21) Appl. No.: 14/355,982

(22) PCT Filed: Oct. 31, 2012

(86) PCT No.: PCT/EP2012/071637
§ 371 (c)(1),
(2) Date: May 2, 2014

(87) PCT Pub. No.: WO2013/064583
PCT Pub. Date: May 10, 2013

(65) Prior Publication Data
US 2014/0322307 A1    Oct. 30, 2014

Related U.S. Application Data

(60) Provisional application No. 61/555,897, filed on Nov. 4, 2011.

(30) Foreign Application Priority Data

Nov. 4, 2011 (ES) .................................. 201131777

(51) Int. Cl.
| | |
|---|---|
| *C07K 7/06* | (2006.01) |
| *A61K 9/127* | (2006.01) |
| *A61K 45/06* | (2006.01) |
| *A61Q 17/04* | (2006.01) |
| *A61K 8/02* | (2006.01) |
| *A61Q 11/00* | (2006.01) |
| *A61K 9/16* | (2006.01) |
| *A61K 8/64* | (2006.01) |
| *A61K 8/14* | (2006.01) |
| *A61K 38/08* | (2006.01) |
| *A61Q 19/00* | (2006.01) |

(52) U.S. Cl.
CPC ................. *A61K 8/0275* (2013.01); *A61K 8/14* (2013.01); *A61K 8/64* (2013.01); *A61K 9/127* (2013.01); *A61K 9/1652* (2013.01); *A61K 38/08* (2013.01); *A61K 45/06* (2013.01); *A61Q 11/00* (2013.01); *A61Q 17/04* (2013.01); *A61Q 19/00* (2013.01); *A61Q 19/007* (2013.01); *C07K 7/06* (2013.01)

(58) Field of Classification Search
None
See application file for complete search history.

(56) References Cited

U.S. PATENT DOCUMENTS

| | | |
|---|---|---|
| 6,750,229 B2 | 6/2004 | Seiberg et al. |
| 2004/0266687 A1 | 12/2004 | Hembrough et al. |
| 2006/0104944 A1 | 5/2006 | Mousa |
| 2006/0142203 A1 | 6/2006 | Hembrough et al. |
| 2006/0183664 A1 | 8/2006 | Takizawa et al. |

FOREIGN PATENT DOCUMENTS

| | | |
|---|---|---|
| EP | 0948308 B1 | 2/2004 |
| EP | 1139974 A1 | 7/2007 |
| EP | 1077063 B1 | 8/2007 |
| WO | WO 03/006048 A1 | 1/2001 |
| WO | WO 2006/035936 A1 | 4/2006 |
| WO | WO 2006/127379 A2 | 11/2006 |
| WO | WO 2009/117481 A1 | 9/2009 |
| WO | WO 2011/146704 | 11/2011 |

OTHER PUBLICATIONS

Albericio, F. et al., "Preparation and application of the 5-(4-(9-fluorenylmethyloxycarbonyl) aminomethyl-3,5-dimethoxyphenoxy)valeric acid (PAL) handle for the solid-phase synthesis of C-terminal peptide amides under mild conditions," J. Org. Chem., 55, 3730-3743 (1990).

Amadesi, S. et al., "Protease-Activated Receptor 2 Sensitizes the Capsaicin Receptor Transient Receptor Potential Vanilloid Receptor 1 to Induce Hyperalgesia," J. Neurosci., 24(18), 4300-4312 (2004).

Atherton, B. and Sheppard R.C., "Solid Phase Peptide Synthesis: A practical approach," IRL Oxford University Press, pp. v., 2-9, 16-21, 47-61(1989).

Barlos, K. et al., "Darstellung geschützter Peptid-Fragmente unter Einsatz substituierter Triphenylmethyl-Harze," (1989), Tetrahedron Lett., 30, 3943-3946.

Barlos, K. et al., "Veresterung von partiell geschützten Peptid-Fragmenten mit Harzen. Einsatz von 2-Chlorotritylchlorid zur Synthese von Leu1-Gastrin I," Tetrahedron Lett., 30, 3947-3951 (1989).

Berge, S.M., et al., "Pharmaceutical Salts," J. Pharm. Sci., 66, 1-19 (1977).

Berger, P., et al., "Tryptase and agonists of PAR-2 induce the proliferation of human airway smooth muscle cells," J. Appl. Physiol., 91(3), 1372-1379 (2001).

Bodanzsky, M. and Bodanzsky A., "The practice of Peptide Synthesis," pp. 76- 126, Springer Verlag, Berlin (1994).

(Continued)

*Primary Examiner* — Marcela M Cordero Garcia
*Assistant Examiner* — Catherine Mader
(74) *Attorney, Agent, or Firm* — Fay Sharpe LLP

(57) ABSTRACT

The present invention refers to a peptide of general formula (I)  $R_1\text{-}W_n\text{-}X_m\text{-}AA_1\text{-}AA_2\text{-}AA_3\text{-}AA_4\text{-}AA_5\text{-}AA_6\text{-}Y_p\text{-}Z_q\text{-}R_2$, cosmetic compositions which comprises said peptide, method of preparation of said peptides and its use in the treatment and/or prevention of itching, inflammation, pain, diseases and/or disorders of the respiratory airways.

25 Claims, No Drawings

(56) References Cited

OTHER PUBLICATIONS

Carvalho, R.F. et al. "Increased mast cell expression of PAR-2 in skin inflammatory diseases and release of IL-8 upon PAR-2 activation," Exp. Dermatol., 19(2), 117-122 (2010).
Cenac, N., et al., "Role for protease activity in visceral pain in irritable bowel syndrome," J. Clin. Invest., 117(3), 636-647 (2007).
Chiu, L.L., et al., "Mold allergen, Pen c13, induced IL-8 expression in human airway epithelial cells by activated Protease-Activated Receptor 1 and 2," J. Immunol., 178(8), 5237-5244 (2007).
Christensen, T., "A Qualitative Test for Monitoring Coupling Completeness in Solid Phase Peptide Synthesis Using Chloranil," (1979), Acta Chem. Scand., 33B, 763-766.
Costa, R., et al. "Evidence for the role of neurogenic inflammation components in trypsin-elicited scratching behaviour in mice," Br. J. Pharmacol., 154(5), 1094-1103 (2008).
Dai, Y. et al., "Proteinase-Activated Receptor 2-Mediated Potentiation of Transient Receptor Potential Vanilloid Subfamily 1 Activity Reveals a Mechanism for Proteinase-Induced Inflammatory Pain," J. Neurosci., 24(18), 4293-4299 (2004).
D'Andrea, M., et al., "Characterization of Protease-Activated Receptor-2 immunoreactivity in normal human tissues," J. Histochem. Cytochem., 46(2), 157-164 (1998).
D'Andrea, M.R., et al., "Differential expression of Protease-Activated Receptors-1 and -2 in stromal fibroblasts of normal, benign, and malignant human tissues," Am. J. Pathol., 158(6), 2031-2041 (2001).
Darmoul, D., et al., "Initiation of human colon cancer cell proliferation by trypsin acting at Protease-Activated Receptor-2," Br. J. Cancer, 85(5), 772-779 (2001).
De Graaf, K.L., "Characterization of the encephalitogenic immune response in a model of multiple sclerosis," Eur. J. Immunol., 38: 299-308 (2008).
Derian, C.K., et al., "Differential regulation of human keratinocyte growth and differentiation by a novel family of protease-activated receptors," Cell Growth Differ., 8(7), 743-749 (1997).
Dooley, T.P., "Recent advances in cutaneous melanoma oncogenesis research," Onco. Res., 6, 1-9 (1994).
Elste, A.P., et al., "Expression of proteinase-activated receptor 1-4 (PAR 1-4) in human cancer," J. Mol. Histol., 41(2-3), 89-99 (2010).
Elsner, P., "Antimicrobials and the Skin, Physiological and Pathological Flora," Hipler, U.C. and Elsner, P., eds., "Biofunctional Textiles and the Skin" Curr. Probl. Dermatol. v.33, S. Karger AG, Basel, Switzerland, pp. 35-41 (2006).
Ferrell, W.R. et al., "Essential role for Proteinase-Activated Receptor-2 in arthritis," (2003), J. Clin. Invest., 111(1), 35-41.
Gottschalck, T.E., et al., eds, CTFA International Cosmetic Ingredient Dictionary & Handbook, 12th Edition, vol. 3, pp. 3040-3065 (2008).
Greaves, M., "Recent advances in pathophysiology and current management of itch," Ann. Acad. Med. Singapore, 36(9), 788-792 (2007).
Hachem, J.-P. et al., "Serine protease signaling of epidermal permeability barrier homeostasis," J. Invest. Dermatol., 126(9), 2074-2086 (2006).
Haug, S., et al., "Coated Textiles in the Treatment of Atopic Dermatitis," Hipler, U.C. and Elsner, P., eds., "Biofunctional Textiles and the Skin" Curr. Probl. Dermatol. v.33, S. Karger AG, Basel, Switzerland, pp. 144-151 (2006).
Hollenberg, M.D., "Physiology and pathophisiology of Proteinase Activated Receptors (PARs): proteinases as hormone-like signal messengers: PARs and more," J. Pharmacol. Sci., 97, pp. 8-13 (2005).
Holzhausen, M., et al., "Role of Protease-Activated Receptor-2 in inflammation, and its possible implications as a putative mediator of periodontitis," Mem. Inst. Oswaldo Cruz, 100(1), 177-180 (2005).
Hoogerwerf, W.A., et al., "The Proteinase-Activated Receptor-2 is involved in nociception," J. Neurosci., 21(22), 9036-9042 (2001).
Hou, L. et al., "Immunolocalization of Protease-Activated Receptor-2 in skin: receptor activation stimulates interleukin-8 secretion by keratinocytes in vitro," Immunology, 94(3), 356-362 (1998).

Ikeda, O. et al., "Signal of Proteinase-Activated Receptor-2 contributes to highly malignant potential of human pancreatic cancer by up-regulation of interleukin-8 release," Int. J. Oncol., 28(4), 939-946 (2006).
IUPAC-IUB Commission of Biochemical Nomenclature, Nomenclature and Symbolism for Amino Acids and Peptides, specified in Eur. J. Biochem., 138, 9-37 (1984).
Jeong, S.K., et al., "Mite and cockroach allergens activate Protease-Activated Receptor 2 and delay epidermal permeability barrier recovery," J. Invest. Dermatol., 128(8), 1930-1939 (2008).
Jin, E., et al., "Protease-Activated Receptor (PAR)-1 and PAR-2 participate in the cell growth of alveolar capillary endothelium in primary lung adenocarcinomas," Cancer, 97(3), 703-713 (2003).
Kaiser, E. et al., "Color test for detection of free terminal amino groups in the solid-phase synthesis of peptides," (1970), Anal. Biochem., 34(2), 595-598.
Kanke, T., et al., "Novel antagonists for proteinase-activated receptor 2: inhibition of cellular and vascular responses in vitro and in vivo," Br. J. Pharmacol., 158, 361-371 (2009).
Kawabata, A. et al., "Increased vascular permeability by a specific agonist of Protease-Activated Receptor-2 in rat hindpaw," Br. J. Pharmacol., 125(3), 419-422 (1998).
Kawagoe, J., et al., "Effect of Protease-Activated Receptor-2 deficiency on allergic dermatitis in the mouse ear," Jpn. J. Pharmacol., 88(1), 77-84 (2002).
Kelso, E.B., et al., "Therapeutic promise of Proteinase-Activated Receptor-2 antagonism in joint inflammation," J. Pharmacol. Exp. Ther., 316(3), 1017-1024 (2006).
King, C. et al., "Dust mite proteolytic allergens induce cytokine release from cultured airway epithelium," J. Immunol., 161(7), 3645-3651 (1998).
Knight, D.A., et al., "Protease-Activated Receptors in human airways: upregulation of PAR2 in respiratory epithelium from patients with asthma," J. Allergy Clin. Immunol., 108(5), 797-803 (2001).
Komatsu, N., et al., "Elevated human tissue kallikrein levels in the stratum corneum and serum of peeling skin syndrome-type B patients suggests an over-desquamation of corneocytes," J. Invest. Dermatol., 126(10), 2338-2342 (2006).
Kullmann, W., "Proteases as catalysts for enzymic syntheses of opioid peptides," J. Biol. Chem., 255(17) 8234-8238 (1980).
Lam, D.K. et al., "Serine proteases and Protease-Activated Receptor-2-dependent allodynia: a novel cancer pain pathway," Pain, 149(2), 263-272 (2010).
Li, Z. et al., "Expression of Protease-Activated Receptor-2 (PAR-2) in patients with nasopharyngeal carcinoma: correlation with clinicopathological features and prognosis," Pathol. Res. Pract., 205(8), 542-550 (2009).
Lloyd-Williams, P., et al., "Chemical Approaches to the Synthesis of Peptides and Proteins," pp. 19-93 CRC, Boca Raton, FL, USA (1997).
Lourbakos, A. et al., "Arginine-specific protease from *Porphyromonas gingivalis* activates Protease-Activated Receptors on human oral epithelial cells and induces interleukin-6 secretion," Infect. Immun., 69(8), 5121-5130 (2001).
Malcolm, R.K. et al., "Controlled release of a model antibacterial drug from a novel self-lubricating silicone biomaterial," J. Cont. Release, 97(2), 313-320 (2004).
Matsueda, G.R. et al., "A p-methylbenzhydrylamine resin for improved solid-phase synthesis of peptide amides," Peptides, 2, 45-50 (1981).
Meredith, P., et al., "Radiative relaxation quantum yields for synthetic eumelanin," Photochem. Photobiol., 79(2), 211-216 (2004).
Miike, S. et al., "Trypsin induces activation and inflammatory mediator release from human eosinophils through Protease-Activated Receptor-2," J. Immunol., 167(11), 6615-6622 (2001).
Miki, M., et al., "Effect of human airway trypsin-like protease on intracellular free $Ca^{2+}$ concentration in human bronchial epithelial cells," J. Med. Invest., 50(1-2), 95-107 (2003).
Morris, D.R. et al., "Protease-Activated Receptor-2 is essential for factor Vlla and Xa-induced signaling, migration, and invasion of breast cancer cells," Cancer Res., 66(1), 307-314 (2006).
Nelson, G., "Application of microencapsulation in textiles," (2002), Int. J. Pharm., 242(1-2), 55-62.

(56) References Cited

OTHER PUBLICATIONS

Noorbakhsh, F. et al., "Proteinase-Activated Receptor-2 modulates neuroinflammation in experimental autoimmune encephalomyelitis and multiple sclerosis," J. Exp. Med., 203(2), 425-435 (2006).

Nystedt, S., et al. "The Proteinase-activated Receptor 2 is induced by inflammatory mediators in human endothelial cells. Comparison with the thrombin receptor," J. Biol. Chem., 1271(25), 14910-14915 (1996).

Ossovskaya, V.S., et al., "Protease-Activated Receptors-contribution to physiology and disease," Physiol. Rev., 84, 579-621 (2004).

Page, K., et al., "Mucosal sensitization to German cockroach involves Protease-Activated Receptor-2," Respir. Res., 11(1), 62, 1-10 (2010).

Rink, H., "Solid-phase synthesis of protected peptide fragments using a trialkoxy-diphenyl-methylester resin," Tetrahedron Lett., 28, 3787-3790 (1987).

Roberts, D.C. et al., "Unusual amino acids in peptide synthesis," in The Peptides, vol. 5. (1983), Chapter VI, Gross E. and Meienhofer J., Eds., Academic Press, New York, USA.

Sánchez-Hernández, P.E., et al., "Protease-Activated Receptor-2 (PAR-2) in cervical cancer proliferation," Gynecol. Oncol., 108(1), 19-26 (2008).

Saifeddine, M., et al., "Rat Proteinase-Activated Receptor-2 (PAR-2): cDNA sequence and activity of receptor-derived peptides in gastric and vascular tissue," (1996), Br. J. Pharmacol., 118, 521-530.

Schmidlin, F., et al., "Protease-Activated Receptor-2 mediates eosinophil infiltration and hyperreactivity in allergic inflammation of the airway," J. Immunol., 169(9), 5315-5321 (2002).

Scott, G., et al., "Protease-Activated Receptor-2, a receptor involved in melanosome transfer, is upregulated in human skin by ultraviolet irradiation," J. Invest. Dermatol., 117(6), 1412-1420 (2001).

Schaab, C.K., HAPPI pp. 84-86 (May 1986).

Seiberg, M., "Keratinocyte-melanocyte interactions during melanosome transfer," Pigment Cell Res., 14(4), 236-242 (2001).

Seiberg, M., et al., "Inhibition of melanosome transfer results in skin lightening," J. Invest. Dermatol., 115(2), 162-167 (2000).

Shimada, S.G., et al., "Scratching behavior in mice induced by the Proteinase-Activated Receptor-2 agonist, SLIGRL-NH2," Eur. J. Pharmacol., 530(3), 281-283 (2006).

Smith-Swintowski, V.L., et al., "Protease-Activated Receptor-2 (PAR-2) is present in the rat hippocampus and is associated with neurodegeneration," J. Neurochem., 69(5), 1890-1896 (1997).

Sobey, C.G., et al., "Activation of Protease-Activated Receptor-2 (PAR-2) elicits nitric oxide-dependent dilatation of the basilar artery in vivo," Stroke, 29(7), 1439-1444 (1998).

Steinhoff, M., et al. "Agonists of Proteinase-Activated Receptor-2 induce inflammation by a neurogenic mechanism," Nat. Med., 6(2), 151-158 (2000).

Steinhoff, M., et al., "Proteinase-Activated Receptor-2 mediates itch: a novel pathway for pruritus in human skin," J. Neurosci., 23(15), 6176-6180 (2003).

Stewart, J.M., and Young, J.D., "Solid Phase Peptide Synthesis," 2nd edition, pp. 1-9 and 70-95, Pierce Chemical Company, Rockford, Illinois (1984).

Sun, G., et al., "Interaction of mite allergens Der P3 and Der P9 with Protease-Activated Receptor-2 expressed by lung epithelial cells," J. Immunol., 167(2), 1014-1021 (2001).

Vergnolle, N., et al., "Characterization of the inflammatory response to Proteinase-Activated Receptor-2 ($PAR_2$)-activating peptides in the rat paw," Br. J. Pharmacol., 127(5), 1083-1090 (1999).

Vergnolle, N., et al., "Proteinase-Activated Receptor-2 and hyperalgesia: a novel pain pathway," Nat. Med., 7(7), 821-826 (2001).

Wang, S.S., "p-Alkoxybenzyl Alcohol Resin and p-Alkoxybenzyloxycarbonylhydrazide Resin for Solid Phase Synthesis of Protected Peptide Fragments," J.Am.Chem.Soc., 95, 1328-1333 (1973).

Wilson, S., et al., "The membrane-anchored serine protease, TMPRSS2, activates PAR-2 in prostate cancer cells," Biochem. J., 388(Pt 3), 967-972 (2005).

Wilkinson J.B., Moore, R.J., eds., "Harry's Cosmeticology," Seventh edition, pp. 51-73 and 757-798, Longman House, Essex, GB (1982).

Lloyd-Williams, et al., "Convergent Solid-Phase Peptide Synthesis," Tetrahedron, vol. 49(48), pp. 11065-11133 (1993).

SEQUENCE LISTING

```
<160> NUMBER OF SEQ ID NOS: 98

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: X at 1 and 2 is any amino acid or absent
<220> FEATURE:
<221> NAME/KEY: misc_feature
<222> LOCATION: (3)..(3)
<223> OTHER INFORMATION: X at 3 is Phe, Ser, Trp, or Phg
<220> FEATURE:
<221> NAME/KEY: misc_feature
<222> LOCATION: (4)..(4)
<223> OTHER INFORMATION: X at 4 is Met, Phe, Nle, Trp, Phg, or Nva
<220> FEATURE:
<221> NAME/KEY: misc_feature
<222> LOCATION: (5)..(5)
<223> OTHER INFORMATION: X at 5 is Arg, Gln, Trp, Lys, Orn, His, Cit,
      Asn, or Phg
<220> FEATURE:
<221> NAME/KEY: misc_feature
<222> LOCATION: (6)..(6)
<223> OTHER INFORMATION: X at 6 is Asp, Phe, Asn, Gln, Tyr, Trp, or Phg
<220> FEATURE:
<221> NAME/KEY: misc_feature
<222> LOCATION: (7)..(7)
<223> OTHER INFORMATION: X at 7 is His, Ile, Orn, Cit, Nle, or Nva
```

```
<220> FEATURE:
<221> NAME/KEY: misc_feature
<222> LOCATION: (8)..(8)
<223> OTHER INFORMATION: X at 8 is Ser, Val, Thr, Nle, Ile, Ala, or Nva
<220> FEATURE:
<221> NAME/KEY: misc_feature
<222> LOCATION: (9)..(10)
<223> OTHER INFORMATION: X at 9 and 10 is any amino acid or absent

<400> SEQUENCE: 1

Xaa Xaa Xaa Xaa Xaa Xaa Xaa Xaa Xaa Xaa
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Phe Met Arg Asp His Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Phe Met Gln Phe His Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Phe Phe Gln Phe His Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ser Phe Gln Phe His Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Phe Met Trp Phe His Ser
1               5
```

```
<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Ser Met Trp Phe His Ser
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Phe Phe Trp Phe His Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Ser Phe Trp Phe His Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Phe Phe Gln Asp Ile Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Phe Met Trp Asp Ile Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Phe Phe Trp Asp Ile Ser
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Phe Met Arg Phe Ile Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Ser Phe Arg Phe Ile Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Phe Met Gln Phe Ile Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Ser Met Gln Phe Ile Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Phe Phe Gln Phe Ile Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Ser Phe Gln Phe Ile Ser
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Phe Met Trp Phe Ile Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Ser Met Trp Phe Ile Ser
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Phe Phe Trp Phe Ile Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Ser Phe Trp Phe Ile Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Phe Phe Arg Asp His Val
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Phe Phe Trp Asp His Val
1               5
```

```
<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Phe Met Arg Phe His Val
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Phe Phe Arg Phe His Val
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

Phe Met Gln Phe His Val
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Ser Met Gln Phe His Val
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Phe Phe Gln Phe His Val
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Phe Met Trp Phe His Val
1               5
```

```
<210> SEQ ID NO 31
<211> LENGTH: 6
<212> TYPE: PRT
<213> ORGANISM: Artificial Sequence
<220> FEATURE:
<223> OTHER INFORMATION: Synthetic peptide

<400> SEQUENCE: 31

Ser Met Trp Phe His Val
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide

<400> SEQUENCE: 32

Phe Phe Trp Phe His Val
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide

<400> SEQUENCE: 33

Ser Phe Trp Phe His Val
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide

<400> SEQUENCE: 34

Phe Phe Arg Asp Ile Val
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide

<400> SEQUENCE: 35

Phe Met Gln Asp Ile Val
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Phe Phe Gln Asp Ile Val
1               5
```

```
<210> SEQ ID NO 37
<211> LENGTH: 6
<212> TYPE: PRT
<213> ORGANISM: Artificial Sequence
<220> FEATURE:
<223> OTHER INFORMATION: Synthetic peptide

<400> SEQUENCE: 37

Phe Met Trp Asp Ile Val
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Phe Phe Trp Asp Ile Val
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide

<400> SEQUENCE: 39

Phe Met Arg Phe Ile Val
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Ser Met Arg Phe Ile Val
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide

<400> SEQUENCE: 41

Phe Phe Arg Phe Ile Val
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide

<400> SEQUENCE: 42

Ser Phe Arg Phe Ile Val
1               5
```

```
<210> SEQ ID NO 43
<211> LENGTH: 6
<212> TYPE: PRT
<213> ORGANISM: Artificial Sequence
<220> FEATURE:
<223> OTHER INFORMATION: Synthetic peptide

<400> SEQUENCE: 43

Phe Met Gln Phe Ile Val
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide

<400> SEQUENCE: 44

Ser Met Gln Phe Ile Val
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide

<400> SEQUENCE: 45

Phe Phe Gln Phe Ile Val
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide

<400> SEQUENCE: 46

Ser Phe Gln Phe Ile Val
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide

<400> SEQUENCE: 47

Phe Met Trp Phe Ile Val
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide

<400> SEQUENCE: 48

Ser Met Trp Phe Ile Val
1               5
```

```
<210> SEQ ID NO 49
<211> LENGTH: 6
<212> TYPE: PRT
<213> ORGANISM: Artificial Sequence
<220> FEATURE:
<223> OTHER INFORMATION: Synthetic peptide

<400> SEQUENCE: 49

Phe Phe Trp Phe Ile Val
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at 6 is Nva

<400> SEQUENCE: 50

Phe Met Asn Trp Ile Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X at 6 is Nva

<400> SEQUENCE: 51

Phe Met Asn Tyr Ile Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is Nva

<400> SEQUENCE: 52

Phe Met Gln Trp Xaa Ile
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is Nva

<400> SEQUENCE: 53

Phe Met Asn Tyr Xaa Ile
1               5
```

```
<210> SEQ ID NO 54
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is Nle

<400> SEQUENCE: 54

Phe Met Gln Trp Xaa Ile
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is Phg
<220> FEATURE:
<221> NAME/KEY: MISC_FEATURE
<222> LOCATION: (5)..(5)
<223> OTHER INFORMATION: X is Nle

<400> SEQUENCE: 55

Phe Met Gln Xaa Xaa Ala
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(6)
<223> OTHER INFORMATION: X at 5 and 6 is Nle

<400> SEQUENCE: 56

Phe Met Gln Tyr Xaa Xaa
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is Phg
<220> FEATURE:
<221> NAME/KEY: MISC_FEATURE
<222> LOCATION: (5)..(5)
<223> OTHER INFORMATION: X is Nva

<400> SEQUENCE: 57

Phe Met Gln Xaa Xaa Ala
1               5
```

```
<210> SEQ ID NO 58
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is Nva

<400> SEQUENCE: 58

Phe Met Gln Trp Xaa Ala
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is Phg
<220> FEATURE:
<221> NAME/KEY: MISC_FEATURE
<222> LOCATION: (6)..(6)
<223> OTHER INFORMATION: X is Nle

<400> SEQUENCE: 59

Phe Trp Gln Xaa Ile Xaa
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(6)
<223> OTHER INFORMATION: X at 5 and 6 is Nle

<400> SEQUENCE: 60

Phe Trp Gln Tyr Xaa Xaa
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is Cit

<400> SEQUENCE: 61

Phe Trp Xaa Gln Ile Val
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (2)..(2)
<223> OTHER INFORMATION: X is Nle
<220> FEATURE:
<221> NAME/KEY: MISC_FEATURE
<222> LOCATION: (3)..(3)
<223> OTHER INFORMATION: X is Cit

<400> SEQUENCE: 62

Phe Xaa Xaa Gln Ile Val
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Nle

<400> SEQUENCE: 63

Phe Xaa His Asn Ile Val
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Nva

<400> SEQUENCE: 64

Phe Xaa His Gln Ile Val
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Nva
<220> FEATURE:
<221> NAME/KEY: MISC_FEATURE
<222> LOCATION: (3)..(3)
<223> OTHER INFORMATION: X is Cit

<400> SEQUENCE: 65

Phe Xaa Xaa Gln Ile Val
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (2)..(2)
<223> OTHER INFORMATION: X is Nva

<400> SEQUENCE: 66

Phe Xaa His Asn Ile Val
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Nva
<220> FEATURE:
<221> NAME/KEY: MISC_FEATURE
<222> LOCATION: (3)..(3)
<223> OTHER INFORMATION: X is Cit

<400> SEQUENCE: 67

Phe Xaa Xaa Asn Ile Val
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Nle
<220> FEATURE:
<221> NAME/KEY: MISC_FEATURE
<222> LOCATION: (3)..(3)
<223> OTHER INFORMATION: X is Orn

<400> SEQUENCE: 68

Phe Xaa Xaa Asp Ile Thr
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Nle

<400> SEQUENCE: 69

Phe Xaa Lys Asp Ile Val
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (2)..(2)
<223> OTHER INFORMATION: X is Phg
<220> FEATURE:
<221> NAME/KEY: MISC_FEATURE
<222> LOCATION: (3)..(3)
<223> OTHER INFORMATION: X is Orn
<220> FEATURE:
<221> NAME/KEY: MISC_FEATURE
<222> LOCATION: (5)..(5)
<223> OTHER INFORMATION: X is Cit

<400> SEQUENCE: 70

Phe Xaa Xaa Asp Xaa Thr
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Phg
<220> FEATURE:
<221> NAME/KEY: MISC_FEATURE
<222> LOCATION: (3)..(3)
<223> OTHER INFORMATION: X is Orn
<220> FEATURE:
<221> NAME/KEY: MISC_FEATURE
<222> LOCATION: (5)..(5)
<223> OTHER INFORMATION: X is Cit

<400> SEQUENCE: 71

Phe Xaa Xaa Asp Xaa Val
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Phg
<220> FEATURE:
<221> NAME/KEY: MISC_FEATURE
<222> LOCATION: (5)..(5)
<223> OTHER INFORMATION: X is Orn

<400> SEQUENCE: 72

Phe Xaa Arg Asp Xaa Thr
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is Phg
<220> FEATURE:
<221> NAME/KEY: MISC_FEATURE
<222> LOCATION: (5)..(5)
<223> OTHER INFORMATION: X is Cit
```

-continued

```
<400> SEQUENCE: 73

Phe Xaa Lys Asp Xaa Val
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: X is Cit

<400> SEQUENCE: 74

Phe Phe Lys Asp Xaa Thr
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is Orn

<400> SEQUENCE: 75

Phe Phe Lys Asp Xaa Thr
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is Phg
<220> FEATURE:
<221> NAME/KEY: MISC_FEATURE
<222> LOCATION: (5)..(5)
<223> OTHER INFORMATION: X is Orn

<400> SEQUENCE: 76

Xaa Phe Lys Asp Xaa Val
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is Phg
<220> FEATURE:
<221> NAME/KEY: MISC_FEATURE
<222> LOCATION: (3)..(3)
<223> OTHER INFORMATION: X is Phg
<220> FEATURE:
<221> NAME/KEY: MISC_FEATURE
<222> LOCATION: (5)..(5)
<223> OTHER INFORMATION: X is Orn
```

```
<400> SEQUENCE: 77

Xaa Phe Xaa Asp Xaa Val
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is Phg
<220> FEATURE:
<221> NAME/KEY: MISC_FEATURE
<222> LOCATION: (3)..(3)
<223> OTHER INFORMATION: X is Phg
<220> FEATURE:
<221> NAME/KEY: MISC_FEATURE
<222> LOCATION: (6)..(6)
<223> OTHER INFORMATION: X is Nva

<400> SEQUENCE: 78

Xaa Phe Xaa Asp Ile Xaa
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is Phg
<220> FEATURE:
<221> NAME/KEY: MISC_FEATURE
<222> LOCATION: (3)..(3)
<223> OTHER INFORMATION: X is Phg
<220> FEATURE:
<221> NAME/KEY: MISC_FEATURE
<222> LOCATION: (6)..(6)
<223> OTHER INFORMATION: X is Nle

<400> SEQUENCE: 79

Xaa Phe Xaa Asp Ile Xaa
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is Phg

<400> SEQUENCE: 80

Trp Phe Xaa Asp Ile Ile
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (6)..(6)
<223> OTHER INFORMATION: X is Nva

<400> SEQUENCE: 81

Trp Phe Trp Asn Ile Xaa
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic peptide

<400> SEQUENCE: 82

Trp Phe His Gln Ile Val
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic peptide

<400> SEQUENCE: 83

Trp Trp Asn Asp His Val
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide

<400> SEQUENCE: 84

Gly Phe Phe Trp Phe His Val
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic peptide

<400> SEQUENCE: 85

Phe Phe Trp Phe His Val Ala Val
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic peptide

<400> SEQUENCE: 86

Ile Phe Phe Trp Phe His Val Gly
1               5
```

```
<210> SEQ ID NO 87
<211> LENGTH: 8
<212> TYPE: PRT
<213> ORGANISM: Artificial Sequence
<220> FEATURE:
<223> OTHER INFORMATION: Synthetic peptide

<400> SEQUENCE: 87

Ala Gly Phe Phe Trp Phe His Val
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 88

Phe Phe Trp Phe His Val Tyr
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 89

Ala Phe Met Trp Phe His Val
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic peptide

<400> SEQUENCE: 90

Phe Met Trp Phe His Val Ala Gly
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic peptide

<400> SEQUENCE: 91

Ala Leu Phe Met Trp Phe His Val
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Phe Met Trp Phe His Val Val
1               5
```

```
<210> SEQ ID NO 93
<211> LENGTH: 8
<212> TYPE: PRT
<213> ORGANISM: Artificial Sequence
<220> FEATURE:
<223> OTHER INFORMATION: Synthetic peptide

<400> SEQUENCE: 93

Gly Phe Met Trp Phe His Val Gly
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide

<400> SEQUENCE: 94

Ala Phe Phe Trp Asp Ile Val
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic peptide

<400> SEQUENCE: 95

Phe Phe Trp Asp Ile Val Gly Gly
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic peptide

<400> SEQUENCE: 96

Ile Phe Phe Trp Asp Ile Val Ile
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic peptide

<400> SEQUENCE: 97

Thr Gly Phe Phe Trp Asp Ile Val
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 98

Phe Phe Trp Asp Ile Val Tyr
1               5
```

PEPTIDES WHICH INHIBIT ACTIVATED RECEPTORS AND THEIR USE IN COSMETIC OR PHARMACEUTICAL COMPOSITIONS

This application claims the priority and benefit of International Application PCT/EP2012/071637, filed Oct. 31, 2012, ES P2011-31777, filed Nov. 4, 2011, and U.S. Application Ser. No. 61/555,897, filed Nov. 4, 2011, from which the PCT application claims priority, the disclosures of which are incorporated herein by reference in their entireties.

FIELD OF THE INVENTION

This invention relates to peptides capable of inhibiting the activity of the Proteinase-Activated Receptor-2, PAR-2 and cosmetic or pharmaceutical compositions which contain said peptides and their use in the treatment and/or care of conditions, disorders and/or diseases which improve or are prevented by the inhibition of PAR-2 activity.

BACKGROUND OF THE INVENTION

Proteases participate in a great variety of biological processes, from the digestion of proteins in the diet in the lumen of the gastrointestinal tract to controlling the cell cycle. An important role of proteases is their participation in signal transduction processes, whether this is by proteolytically cutting ligands or cell surface receptors to generate active ligands, or, on the contrary, to degrade and inactivate agonists of certain receptors. One type of these cell surface receptors which are attacked by the proteases generating active ligands is the family of protease-activated G protein-coupled receptors, PAR (proteinase-activated receptors), for which a protease cuts in a specific place on the extracellular N-terminal domain of the receptor, and this cut means that a new N-terminal domain is exposed which acts as an anchored ligand, bringing about the beginning of the signal transduction [Hollenberg M. D., "*Physiology and pathophisiology of Proteinase Activated Receptors (PARs): proteinases as hormone-like signal messengers: PARs and more*", (2005), *J. Pharmacol. Sci.*, 97, 8-13]. The family of PARs has four members, PAR-1 to PAR-4, which are activated by a large number of proteases, such as coagulation cascade proteases such as thrombin or the TF-FVIIa-FXa complex, inflammatory cell proteases such as mast cell proteases (tryptase) and leucocytes (cathepsin G, elastase and proteinase-3), digestive tract proteases such as trypsins and pancreatic and extrapancreatic trypsinogens, tissue proteases such as kallikreins, as well as non-mammalian proteases, such as bacterial proteases, fungi, mites or insects [Ossovskaya V. S. and Bunnet N. W., "*Protease Activated Receptors-contribution to physiology and disease*", (2004), *Physiol. Rev.*, 84, 579-621]. There is a certain selectivity in PAR activation; thrombin, for example, can activate PAR-1, PAR-3 and PAR-4 with varying degrees of intensity, but does not activate PAR-2, whilst trypsin and tryptase or mast cell proteases activate PAR-2.

Specifically, PAR-2 is widely distributed in the human body, including the skin, the gastrointestinal tract and the circulatory, respiratory and nervous systems, modulating different physiological functions such as coagulation, proliferation and survival, inflammation, neurotransmission and pain. In pathological conditions, such as hemostasis or inflammation, both an overexpression of PAR-2 has been observed [Nystedt S. et al. "*The Proteinase-activated Receptor 2 is induced by inflammatory mediators in human endothelial cells. Comparison with the thrombin receptor*", (1996), *J. Biol. Chem.*, 1271(25), 14910-14915] as well as an overproduction of proteases capable of activating PAR-2.

In the skin, PAR-2 is expressed abundantly in almost all cells types, especially in keratinocytes, and is particularly important in the stratum granulosum, which means its expression can depend on the state of epidermal differentiation. In the stratum corneum there are three families of proteases; specific epidermal serine proteases such as kallikrein-5 (SCTE or stratum corneum tryptic enzyme) or kallikrein-7 (SCCE or stratum corneum chymotryptic enzyme), cysteine proteases such as cathepsins C, L, and V (stratum corneum thiol proteases), and at least one aspartate protease (cathepsin D). The activity of these proteases is closely regulated by specific inhibitors and acts as a mediator of several cells responses in the skin, such as inflammation and immune responses, chemotaxis, cytokine expression, vascular function, tissue and apoptosis repair. As well as said endogenous proteases, signaling in the epidermis can also be due to some exogenous allergen proteases such as domestic mites, cockroaches, pollen, certain bacteria and fungi. PAR-2 is a sensor for all these proteases, playing an important role in the maintenance of homeostasis of the barrier function of the skin. The participation of PAR-2 in homeostasis of the barrier function of the skin has been proven both in cell cultures and in animal models; the activation of PAR-2 in keratinocytes in culture inhibits cell proliferation, which is consistent with the delay in recovery of the barrier and inhibition of the secretion of lamellar bodies observed after the topical application of a PAR-2 peptide agonist or allergens on the skin of mice, whilst an increase in the secretion of lamellar bodies and an accelerated recovery of the barrier function after the disruption to said barrier function has been observed in PAR-2 knockout mice, in comparison with their wild phenotype littermates [Derian C. K. et al., "*Differential regulation of human keratinocyte growth and differentiation by a novel family of protease-activated receptors*", (1997), *Cell Growth Differ.*, 8(7), 743-749; Hachem J.-P. et al., "*Serine protease signaling of epidermal permeability barrier homeostasis*", (2006), *J. Invest. Dermatol.*, 126(9), 2074-2086; Jeong S. K. et al., "*Mite and cockroach allergens activate Protease-Activated Receptor 2 and delay epidermal permeability barrier recovery*", (2008), *J. Invest. Dermatol.*, 128(8), 1930-1939].

The abnormal expression or abnormal activity of proteases and, therefore, the overactivation of PAR-2 is associated with skin disorders or diseases such as atopic dermatitis, Netherton's syndrome, psoriasis and peeling skin syndrome [Komatsu N. et al., "*Elevated human tissue kallikrein levels in the stratum corneum and serum of peeling skin syndrome-type B patients suggests an over-desquamation of corneocytes*", (2006), *J. Invest. Dermatol.*, 126(10), 2338-2342]. Elevated levels of PAR-2 have also been described in skin inflammatory or immune diseases such as lichen planus, atopic dermatitis, psoriasis [Carvalho R. F. et al. "*Increased mast cell expression of PAR-2 in skin inflammatory diseases and release of IL-8 upon PAR-2 activation*"; (2010), *Exp. Dermatol.*, 19(2), 117-122] or rosacea [Hachem J.-P. et al., "*Serine protease signaling of epidermal permeability barrier homeostasis*", (2006), *J. Invest. Dermatol.*, 126(9), 2074-2086].

PAR-2 is also involved in the development of inflammatory processes. Many of the cells which orchestrate the response of the immune system during inflammation express PAR-type receptors; for example eosinophilic infiltrates express PAR-2 [Miike S. et al., "*Trypsin induces activation and inflammatory mediator release from human eosinophils through Protease-Activated Receptor-2*", (2001), *J. Immunol.*, 167(11), 6615-6622]. During the inflammatory processes potential endogenous PAR-2 activators are released, such as leukocyte elastase, mast cell tryptase, proteinases of the trypsin family produced by keratinocytes and proteases of the fibrinolytic cascade such as factors FVIIa or FXa. These components activate PAR-2 in keratinocytes, endothelial cells, inflammatory cells and dermal sensory nerves to amplify inflammation by over-regulating inflammatory mediators. The activation of PAR-2 causes nitric oxide-dependent vasodilation [Saifeddine M. et al., "*Rat Proteinase-Activated Receptor-2 (PAR-2): cDNA sequence and activity of receptor-derived peptides in gastric and vascular tissue*", (1996), *Br. J. Pharmacol.*, 118, 521-530; Sobey C. G. et al., "*Activation of Protease-Activated Receptor-2 (PAR-2) elicits nitric oxide-dependent dilatation of the basilar artery in vivo*", (1998), *Stroke*, 29(7), 1439-1444], induces extravasation of plasma proteins and infiltration of neutrophils [Vergnolle N. et al., "*Characterization of the inflammatory response to Proteinase-Activated Receptor-2-activating peptides in the rat paw*", (1999), *Br. J. Pharmacol.*, 127(5), 1083-1090; Kawabata A. et al., "*Increased vascular permeability by a specific agonist of Protease-Activated Receptor-2 in rat hindpaw*", (1998), *Br. J. Pharmacol.*, 125(3), 419-422], and stimulates the secretion of pro-inflammatory cytokines [Hou L. et al., "*Immunolocalization of Protease-Activated Receptor-2 in skin: receptor activation stimulates interleukin-8 secretion by keratinocytes in vitro*", (1998), *Immunology*, 94(3), 356-362]. Furthermore, it has been described that in an animal model of contact hypersensitivity on mice ears, PAR-2 knockout mice show a reduction in the swelling of ears and in the volume of inflammatory infiltrates, corroborating that PAR-2 plays a role as an inflammatory mediator in allergic dermatitis [Kawagoe J. et al., "*Effect of Protease-Activated Receptor-2 deficiency on allergic dermatitis in the mouse ear*", (2002), *Jpn. J. Pharmacol.*, 88(1), 77-84]. It is also described that PAR-2 intervenes in the development of oral diseases and disorders such as periodontitis; the protease of the microorganism *Porphyromonas gingivalis* presents PAR-2 in the active oral cavity and induces the secretion of IL-6, causing the infiltration of granulocytes in the gums and periodontitis through a mechanism which comprises the release of prostaglandin and the activation of matrix metalloproteinases with the consequential destruction of the collagen tissue supporting the teeth [Lourbakos A. et al., "*Arginine-specific protease from Porphyromonas gingivalis activates Protease-Activated Receptors on human oral epithelial cells and induces interleukin-6 secretion*", (2001), *Infect. Immun.*, 69(8), 5121-5130; Holzhausen M., Spolidorio L. C. and Vergnolle N., "*Role of Protease-Activated Receptor-2 in inflammation, and its possible implications as a putative mediator of periodontitis*", (2005), *Mem. Inst. Oswaldo Cruz.*, 100(1), 177-180].

Chronic inflammatory processes are also mediated by PAR-2, as is the case of rheumatoid arthritis. Activation of PAR-2 in a mouse's knee joint with PAR-2-activating peptides results in a swelling of the joint and hyperemia, clear indicators of inflammation. The duration of the inflammation and swelling can vary according to the nature of the PAR-2-activating peptide. At the same time, an increase in the expression of PAR-2 in the inflamed synovium is detected, as well as in adjacent muscle and skin, presumably by discharge of adjuvant into said tissues during induction, this indicating that the increase in PAR-2 expression is associated with chronic inflammatory responses in different types of tissue. However, mutant PAR-2 knockout mice are protected from arthritis induced by intra-articular and peri-articular injections of CFA [Ferrell W. R. et al., "*Essential role for Proteinase-Activated Receptor-2 in arthritis*", (2003), *J. Clin. Invest.*, 111(1), 35-41; Kelso E. B. et al., "*Therapeutic promise of Proteinase-Activated Receptor-2 antagonism in joint inflammation*", (2006), *J. Pharmacol. Exp. Ther.*, 316(3), 1017-1024].

PAR-2 does not just participate in nociception, but also in the transmission of pain. The injection of sub-inflammatory doses of PAR-2-agonists in murinae induces hyperalgesia sustained by mechanical and thermal stimuli, whilst this somatic hyperalgesia is absent in PAR-2 knockout animals [Vergnolle N. et al., "*Proteinase-Activated Receptor-2 and hyperalgesia: a novel pain pathway*", (2001), *Nat. Med.*, 7(7), 821-826]. The involvement of PAR-2 has also been described, and in particular in inflammatory pain, in visceral pain and pain due to cancer. For example, pancreatitis is associated with premature activation of trypsinogen in the pancreas which induces hyperalgesia by a PAR-2-dependant mechanism [Hoogerwerf W. A. et al., "*The Proteinase-Activated Receptor-2 is involved in nociception*", (2001), *J. Neurosci.*, 21(22), 9036-9042] as well as visceral pain in different diseases of the digestive tract such as irritable bowel syndrome, ulcerative colitis and Crohn's disease [Cenac N., "Role for protease activity in visceral pain in irritable bowel syndrome", (2007), J. Clin. Invest., 117(3), 636-647]. In the same way, mechanical allodynia caused in cancerous processes disappears in PAR-2 knockout mice [Lam D. K. and Schmidt B. L., "*Serine proteases and Protease-Activated Receptor-2-dependent allodynia: a novel cancer pain pathway*", (2010), *Pain*, 149(2), 263-272]. The document WO 2009/117481 A1 describes the use of PAR-2 activity inhibitors for the treatment of chronic pain, inflammatory pain, postoperative pain, neuropathic pain, pain due to fractures, osteoporotic fractures, cancer or joint pain caused by gout, among others.

PAR-2 notably contributes to neurogenic inflammation, as it is expressed in nociceptive peptidergic neurons of the peripheral system, which are responsible for this inflammation. During neurogenic inflammation, different endogenous serine proteases such as mast cell tryptase and keratinocyte trypsin activate PAR-2 in sensory nerve ends to release a calcitonin gene-related peptide (CGRP) and substance P (SP). These neuropeptides are pro-inflammatory: they induce vasodilatation, edema, and leukocyte recruitment, which results in neurogenic inflammation [Steinhoff M. et al. "*Agonists of Proteinase Activated Receptor-2 induce inflammation by a neurogenic mechanism*", (2000), *Nat. Med.*, 6(2), 151-158].

PAR-2 activation also mediates in the induction of itching [Shimada S. G., et al., "*Scratching behavior in mice induced by the Proteinase-Activated Receptor-2 agonist, SLIGRL-NH2*", (2006), *Eur. J. Pharmacol.*, 530(3), 281-283], and this itching is independent of histamine. PAR-2 activation triggers the release of substance P, which, as well as causing itchiness, promotes the continued activation of mast cells via TRK receptors and the resulting release of tryptase, which in turn activates PAR-2 [Greaves M., "*Recent advances in pathophysiology and current management of itch*", (2007), *Ann. Acad. Med. Singapore.*, 36(9), 788-792]. The levels of tryptase are abnormally high in disorders or diseases of which involve itching, such as in atopic dermatitis, in which the concentrations of tryptase are up to four times higher than those observed in healthy skin [Steinhoff M. et al., "*Proteinase-Activated Receptor-2 mediates itch: a novel pathway for pruritus in human skin*", (2003), *J. Neurosci.*, 23(15), 6176-6180]. It is described that PAR-2 antagonists are capable of inhibiting trypsin-elicited scratching [Costa R. et al. "*Evidence for the role of neurogenic inflammation components in trypsin-elicited scratching behaviour in mice*", (2008), *Br. J. Pharmacol.*, 154(5), 1094-1103]. This property opens the door to the treatment of different conditions, disorders or diseases which involve itching through PAR-2 activity inhibitors, such as dermatitis, including contact dermatitis and atopic dermatitis, urticaria, food allergies or allergies to insect bites, among others.

PAR-2 sensitizes the transient receptor potential vanilloid 1 (TRPV-1), which belongs to the TRP channel superfamily, amplifying the response to pain, inflammation and itching [Amadesi S. et al., *"Protease-Activated Receptor 2 Sensitizes the Capsaicin Receptor Transient Receptor Potential Vanilloid Receptor 1 to Induce Hyperalgesia"*, (2004), *J. Neurosci.*, 24(18), 4300-4312; Dai Y. et al., *"Proteinase-Activated Receptor 2-Mediated Potentiation of Transient Receptor Potential Vanilloid Subfamily 1 Activity Reveals a Mechanism for Proteinase-Induced Inflammatory Pain"*, (2004), *J. Neurosci.*, 24(18), 4293-4299].

PAR-2 is also expressed in neurons and astrocytes of the central nervous system in humans and rodents, and has been related to the pathogenesis associated with ischemia and neurodegeneration [Smith-Swintowski V. L. et al., *"Protease-Activated Receptor-2 (PAR-2) is present in the rat hippocampus and is associated with neurodegeneration"*, (1997), *J. Neurochem.*, 69(5), 1890-1896] as well as with the development of multiple sclerosis and in experimental autoimmune encephalomyelitis (EAE) [Noorbakhsh F. et al., *"Proteinase-Activated Receptor-2 modulates neuroinflammation in experimental autoimmune encephalomyelitis and multiple sclerosis"*, (2006), *J. Exp. Med.*, 203(2), 425-435].

PAR-2 also plays an important role in regulating pigmentation. The exposure to UV radiation induces an overexpose of PAR-2 in keratinocytes [Scott G. et al., *"Protease-Activated Receptor-2, a receptor involved in melanosome transfer, is upregulated in human skin by ultraviolet irradiation"*, (2001), *J. Invest. Dermatol.*, 117(6), 1412-1420], whose activation induces melanoma phagocytosis, which involves a transfer of melanocyte melanin to the keratinocyte with the resulting darkening of the epidermis [Seiberg M., *"Keratinocyte-melanocyte interactions during melanosome transfer"*, (2001), *Pigment Cell Res.*, 14(4), 236-242]. Skin coloration has been a concern for human beings for many years. In particular, the capacity to eliminate hyperpigmentation, whether due to age (marks, freckles or the general aging of the skin), or due to disorders or diseases (melasma, chloasma, post-inflammatory hyperpigmentation) is of interest for individuals who want an even-looking skin complexion. Likewise, when exposure to UV radiation is prolonged or excessive, cancerous hyperpigmented lesions or melanomas can develop [Dooley T. P., *"Recent advances in cutaneous melanoma oncogenesis research"*, (1994), *Onco. Res.*, 6, 1-9] as well as benign hyperpigmented marks due to photoaging. It is described that PAR-2 inhibition has a depigmenting effect on the skin [Seiberg M. et al., *"Inhibition of melanosome transfer results in skin lightening"*, (2000), *J. Invest. Dermatol.*, 115(2), 162-167], therefore the treatment of skin with PAR-2 activity inhibitors is a valid strategy to lessen skin pigmentation, as described in documents EP 0948308 B1, EP 1077063 B1, U.S. Pat. No. 6,750,229 B2 and EP 1139974 A1.

However, the use of whitening or depigmenting compounds, whether for the treatment of hyperpigmented areas or areas close to hypopigmented areas, for aesthetic reasons to lighten the natural skin color, its collateral effect is to increase the risk of damage by UV radiation, as they reduce the quantity of melanin produced by melanocytes. Melanin is the skin's natural photoprotector, as it clears, as heat, over 99.9% of UV radiation absorbed [Meredith P. et al., *"Radiative relaxation quantum yields for synthetic eumelanin"*, (2004), *Photochem. Photobiol.*, 79(2), 211-216]. This means that less than 0.1% of radiation absorbed will be capable of generating free radicals, which cause direct and indirect DNA damage and, therefore, photoaging. The cosmetic and pharmaceutical industries compensate this lack of protection inherent in the use of whiteners or depigmenting agents with the addition of formulations of photoprotective substances or solar filters. Solar filters protect the skin from UVB radiation, which may cause burns, and from UVA radiation, which damages the skin on a more long-term scale by causing accelerated aging or photoaging. However, many of these substances are potentially irritating, sensitizing or toxic, their use being regulated and even limited or prohibited in different countries. Therefore, there is a need to develop whitening or depigmenting compounds with an intrinsic photoprotective effectiveness which enable the use of additional photoprotectors to be reduced.

There is also expression of PAR-2 receptors in respiratory channels, in ciliated and non-ciliated epithelial cells, as well as in glands, smooth muscle, vascular smooth muscle cells and endothelial cells [D'Andrea M. et al., *"Characterization of Protease-Activated Receptor-2 immunoreactivity in normal human tissues"*, (1998), *J. Histochem. Cytochem.*, 46(2), 157-164]. Said receptors are activated by endogenous proteases such as trypsin produced in the airway epithelial cells [Miki M. et al., *"Effect of human airway trypsin-like protease on intracellular free $Ca^{2+}$ concentration in human bronchial epithelial cells"*, (2003), *J. Med. Invest.*, 50(1-2), 95-107], or isolated tryptase in human pulmonary mast cells [Berger P. et al., *"Tryptase and agonists of PAR-2 induce the proliferation of human airway smooth muscle cells"*, (2001), *J Appl Physiol.*, 91(3), 1372-1379], as well as by proteases of different allergens, such as cockroaches, mites such as *Dermatophagoides pteronyssinus* or mold [Sun G. et al., *"Interaction of mite allergens Der P3 and Der P9 with Protease-Activated Receptor-2 expressed by lung epithelial cells"*, (2001), *J. Immunol.*, 167(2), 1014-1021; King C. et al., *"Dust mite proteolytic allergens induce cytokine release from cultured airway epithelium"*, (1998), *J Immunol.*, 161(7), 3645-3651; Page K. et al., *"Mucosal sensitization to German cockroach involves Protease-Activated Receptor-2"*, (2010), *Respir. Res.*, 11(1), 62; Chiu L. L. et al., *"Mold allergen, Pen c13, induced IL-8 expression in human airway epithelial cells by activated Protease-Activated Receptor 1 and 2"*, (2007), *J. Immunol.*, 178(8), 5237-5244].

PAR-2 activation correlates with the mast cell infiltration observed in the allergic inflammation of airways; in PAR-2 knockout animal models there is a lesser infiltration of eosinophils in the event of allergic inflammation induced in airways, whilst the mutant which overexpresses PAR-2 presents an increase in this response [Schmidlin F. et al., *"Protease-Activated Receptor-2 mediates eosinophil infiltration and hyperreactivity in allergic inflammation of the airway"*, (2002), *J. Immunol.*, 169(9), 5315-5321]. Likewise, patients with asthma overexpress PAR-2 en respiratory epithelial cells but not in smooth muscle or alveolar macrophages [Knight D. A. et al., *"Protease-Activated Receptors in human airways: upregulation of PAR-2 in respiratory epithelium from patients with asthma"*, (2001), *J. Allergy Clin. Immunol.*, 108(5), 797-803]. Thus, the inhibition of PAR-2 activity is a useful strategy for the treatment of inflammatory diseases of airways, such as allergic rhinitis, chronic obstructive pulmonary disease, bronchial hyperreactivity and asthma.

PAR-2 is expressed in different tumor cells and tissues [D'Andrea M. R. et al., *"Differential expression of Protease-Activated Receptors-1 and -2 in stromal fibroblasts of normal, benign, and malignant human tissues"*, (2001), *Am. J. Pathol.*, 158(6), 2031-2041; Elste A. P. and Petersen I., "*Expression of proteinase-activated receptor 1-4 (PAR 1-4) in human cancer*", (2010), *J. Mol. Histol.*, 41(2-3), 89-99], and plays an important role in the invasion and tumor growth in different malignant neoplasms, such as in the stomach, colon, pancreas, lungs, airways, prostate, uterus and breast [Darmoul D. et al., "*Initiation of human colon cancer cell proliferation by trypsin acting at Protease-Activated Receptor-2*", (2001), *Br. J. Cancer*, 85(5), 772-779; Ikeda O. et al., "*Signal of Proteinase-Activated Receptor-2 contributes to highly malignant potential of human pancreatic cancer by up-regulation of interleukin-8 release*", 2006, *Int. J. Oncol.*, 28(4), 939-946; Jin E. et al., "*Protease Activated Receptor [PAR]-1 and PAR-2 participate in the cell growth of alveolar capillary endothelium in primary lung adenocarcinomas*", (2003), *Cancer*, 97(3), 703-713; Li Z. et al., "*Expression of Protease-Activated Receptor-2 (PAR-2) in patients with nasopharyngeal carcinoma: correlation with clinicopathological features and prognosis*", (2009), *Pathol. Res. Pract.*, 205(8), 542-550; Wilson S. et al., "*The membrane-anchored serine protease, TMPRSS2, activates PAR-2 in prostate cancer cells*", (2005), *Biochem. J.*, 388(Pt 3), 967-972; Sánchez-Hernández P. E. et al., "*Protease-Activated Receptor-2 (PAR-2) in cervical cancer proliferation*", (2008), *Gynecol. Oncol.*, 108(1), 19-26; Morris D. R. et al., "*Protease-Activated Receptor-2 is essential for factor VIIa and Xa-induced signaling, migration, and invasion of breast cancer cells*", (2006), *Cancer Res.*, 66(1), 307-314]. PAR-2 activation gives rise to classic intracellular signals including the induction of an extensive repertoire of proangiogenic factors which facilitate the proliferation and migration of tumor cells; the inhibition of PAR-2 activity is therefore a useful strategy to restrict the growth of tumors and metastasis, as described in document US 2006/0104944 A1.

The cosmetic and pharmaceutical industry has tried on many occasions to find molecules or extracts which inhibit PAR-2, such as those described in documents WO 2006/035936 A1, WO 2006/127379 A2, US 2004/0266687 A1, US 2006/0142203 A1 and US 2006/0183664 A1 among others. However, despite the arsenal of existing compounds and/or extracts, the cosmetic and pharmaceutical sector is still interested in developing alternatives to the compounds known in the prior art for the treatment and/or care of those conditions, disorders and/or diseases that improve or are prevented by the inhibition of PAR-2 activity.

BRIEF DESCRIPTION OF THE INVENTION

In accordance with one aspect of the invention, a peptide of general formula (I)

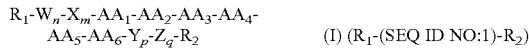

$R_1$-$W_n$-$X_m$-$AA_1$-$AA_2$-$AA_3$-$AA_4$-$AA_5$-$AA_6$-$Y_p$-$Z_q$-$R_2$    (I) ($R_1$-(SEQ ID NO:1)-$R_2$)

its stereoisomers, mixtures thereof and/or its cosmetic or pharmaceutical acceptable salts, wherein:
$AA_1$ is selected from the group consisting of -Phe-, -Ser-, -Trp- and -Phg-;
$AA_2$ is selected from the group consisting of -Met-, -Phe-, -Nle-, -Trp-, -Phg- and -Nva-;
$AA_3$ is selected from the group consisting of -Arg-, -Gln-, -Trp-, -Lys-, -Orn-, -His-, -Cit-, -Asn- and -Phg-;
$AA_4$ is selected from the group consisting of -Asp-, -Phe-, -Asn-, -Gln-, -Tyr-, -Trp- and -Phg-;
$AA_5$ is selected from the group consisting of -His-, -Ile-, -Orn-, -Cit-, -Nle- and -Nva-;
$AA_6$ is selected from the group consisting of -Ser-, -Val-, -Thr-, -Nle-, -Ile-, -Ala- and -Nva-;

W, X, Y, Z are amino acids and are independently selected from amongst themselves;
n, m, p and q are independently selected from amongst themselves and have a value of 0 or 1;
n+m+p+q is smaller than or equal to 2;
$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
$R_1$ or $R_2$ are not α-amino acids.

DETAILED DESCRIPTION OF THE INVENTION

This invention provides a solution to the above-mentioned problem. Surprisingly the authors of this invention have found that the activity of PAR-2 can be inhibited by certain synthetic peptides. Said peptides are useful for the treatment and/or care of those conditions, disorders and/or diseases which improve or are prevented by the inhibition of PAR-2 activity.

DEFINITIONS

In order to facilitate the comprehension of this invention, the meanings of some terms and expressions as used in the context of the invention are included.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes, mast cells, neurons and/or adipocytes among others. The term "skin" also includes the scalp.

The term "treatment", as used in the context of this report, refers to the administration of a peptide according to the invention to alleviate or eliminate a disease or disorder or reduce or eliminate one or more symptoms associated with this disease or disorder. The term "treatment" also covers the ability to alleviate or eliminate the physiological consequences of the disease or disorder.

In the context of this invention "care" comprises the prevention of diseases and/or disorders.

The term "prevention", as used in this invention, refers to the ability of a peptide in the invention to prevent, delay, or hinder the appearance or development of a disease or disorder before its appearance.

In the context of this invention, the term "aging" refers to the changes experienced by the skin with age (chronoaging) or through exposure to the sun (photoaging) or to environmental agents such as tobacco smoke, extreme climatic conditions of cold or wind, chemical contaminants or pollutants, and includes all the external visible and/or perceptible changes through touch, for example and not restricted to, the development of discontinuities on the skin such as wrinkles, fine lines, expression lines, stretch marks, striae, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and present the same physical characteristics as aging, for example and not restricted to, flaccidity, sagging, changes to the color or irregularities in pigmentation, abnormal and/or excessive keratinization.

In this description the abbreviations used for amino acids follow the recommendations of the IUPAC-IUB Commission of Biochemical Nomenclature specified in *Eur. J. Biochem.*, (1984), 138, 9-37.

Thus, for example, Ala represents $NH_2$—$CH(CH_3)$—COOH, Ala- represents $NH_2$—$CH(CH_3)$—CO, -Ala represents —NH—$CH(CH_3)$—COOH and -Ala- represents —NH—$CH(CH_3)$—CO—. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

| Name | Residue | Symbol | Residue |
|---|---|---|---|
| Alanyl -Ala- A | | Glutaminyl -Gln- Q | |
| Histidyl -His- H | | Glycyl -Gly- G | |
| Seryl -Ser- S | | Threonyl -Thr- T | |
| Tyrosyl -Tyr- Y | | Valyl -Val- V | |
| Phenylalanyl -Phe- F | | Methionyl -Met- M | |

TABLE 1-continued

| Name | Residue | Symbol | Residue |
|---|---|---|---|
| Tryptophyl -Trp- W | | Lysyl -Lys- K | |
| Aspartyl -Asp- D | | Isoleucyl -Ile- I | |
| Asparagyl -Asn- N | | Norleucyl -Nle- | |
| Phenylglycyl -Phg- | | Norvalyl -Nva- | |
| Ornithyl -Orn- | | Citrullyl -Cit- | |

The abbreviation "Ac-" is used in this description to denote the acetyl group ($CH_3$—CO—) and the abbreviation "Palm-" is used to denote the palmitoyl group ($CH_3$—$(CH_2)_{14}$—CO—).

The term "non-cyclic aliphatic group" is used in this invention to cover linear or branched alkyl, alkenyl and alkynyl groups.

The term "alkyl group" refers to a saturated linear or branched group which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a simple bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a simple bond, including, for example and not restricted to, vinyl (—CH$_2$=CH$_2$), allyl (—CH$_2$—CH=CH$_2$), oleyl, linoleyl and similar groups.

The term "alkynyl group" refers to a linear or branched group which has between 2 and 24, preferably between 2 and 16, more preferably between 2 and 14, even more preferably between 2 and 12, yet more preferably 2, 3, 4, 5 or 6 carbon atoms with one or more triple carbon-carbon bonds, preferably 1, 2 or 3 triple carbon-carbon bonds, conjugated or unconjugated, which is bound to the rest of the molecule by a simple bond, including, for example and not restricted to the ethynyl group, 1-propynyl, 2-propynyl, 1-butynyl, 2-butynyl, 3-butynyl, pentynyl, such as 1-pentynyl, and similar. The alkynyl groups can also contain one or more double carbon-carbon bonds, including, for example and not restricted to, but-1-en-3-inyl, pent-4-en-1-inyl groups and similar.

The term "alycyclic group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and which is bound to the rest of the molecule by a simple bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, which is bound to the rest of the molecule by a simple bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, which is bound to the rest of the molecule by a simple bond, including, for example and not restricted to, the cyclooct-2-in-1-yl group and similar. Cycloalkynyl groups can also contain one or more double carbon-carbon bonds, including, for example and not restricted to, the cyclooct-4-en-2-inyl group and similar.

The term "aryl group" refers to an aromatic group which has between 6 and 30, preferably between 6 and 18, more preferably between 6 and 10, yet more preferably 6 or 10 carbon atoms, which comprises 1, 2, 3 or 4 aromatic rings, bound by a carbon-carbon bond or fused, including, for example and not restricted to, phenyl, naphthyl, diphenyl, indenyl, phenanthryl or antranyl among others; or to an aralkyl group.

The term "aralkyl group" refers to an alkyl group substituted by an aromatic group, with between 7 and 24 carbon atoms and including, for example and not restricted to, —(CH$_2$)$_{1-6}$-phenyl, —(CH$_2$)$_{1-6}$-(1-naphthyl), —(CH$_2$)$_{1-6}$-(2-naphthyl), —(CH$_2$)$_{1-6}$—CH(phenyl)$_2$ and similar.

The term "heterocyclyl group" refers to a hydrocarbonated ring of 3-10 members, in which one or more of the atoms of the ring, preferably 1, 2 or 3 of the atoms of the ring, is a different element to carbon, such as nitrogen, oxygen or sulfur and can be saturated or unsaturated. For the purposes of this invention, the heterocycle can be a cyclic, monocyclic, bicyclic or tricyclic system, which may include systems of fused rings; and the nitrogen, carbon or sulfur atoms in the heterocyclyl radical may be optionally oxidized; the nitrogen atom may be optionally quaternized; and the heterocyclyl radical may be partially or completely saturated or be aromatic. The greatest preference is for the term heterocyclyl to refer to a ring of 5 or 6 members. Examples of saturated heterocyclyl groups are dioxane, piperidine, piperazine, pyrrolidine, morpholine and thiomorpholine. Examples of aromatic heterocyclyl groups, also known as heteroaromatic groups are pyridine, pyrrol, furan, thiophene, benzofuran, imidazoline, quinolein, quinoline, pyridazine and naphthyridine.

The term "heteroarylalkyl group" refers to an alkyl group substituted by a substituted or unsubstituted aromatic heterocyclyl group, the alkyl group having from 1 to 6 carbon atoms and the aromatic heterocyclyl group between 2 and 24 carbon atoms and from to 3 atoms different to carbon including, for example and not restricted to, —(CH$_2$)$_{1-6}$-imidazolyl, —(CH$_2$)$_{1-6}$-triazolyl, —(CH$_2$)$_{1-6}$-thienyl, —(CH$_2$)$_{1-6}$-furyl, —(CH$_2$)$_{1-6}$-pyrrolidinyl and similar.

As is understood in this technical field, there may be a certain degree of substitution of the aforementioned groups. Therefore, there can be substitution in any of the groups of this invention where it is explicitly stated. The references in this document to substituted groups in the groups of this invention indicate that the specified radical can be substituted in one or more positions available by one or more substitutes, preferably in 1, 2 or 3 positions, more preferably in 1 or 2 positions, yet more preferably in 1 position. These substituents include, for example and not restricted to, alkyl C$_1$-C$_4$; hydroxyl; alcoxyl C$_1$-C$_4$; amino; aminoalkyl carbonyloxyl C$_1$-C$_4$; oxycarbonyl C$_1$-C$_4$; halogen such as fluoride, chlorine, bromine and iodine; cyano; nitro; azide; alkylsulfonyl thiol; alkylthio C$_1$-C$_4$; aryloxyl such as phenoxyl; —NR$_b$(C=NR$_b$)NR$_b$R$_c$; wherein R$_b$ and R$_c$ are independently selected from the group formed by H, alkyl C$_1$-C$_4$, alkenyl C$_2$-C$_4$, alkynyl C$_2$-C$_4$, cycloalkyl C$_3$-C$_{10}$, aryl C$_6$-C$_{18}$, aralkyl C$_7$-C$_{17}$, heterocyclyl of 3-10 members or protective group of the amino group.

Compounds in the Invention

The peptides of the invention are defined by the general formula (I)

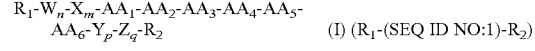

R$_1$-W$_n$-X$_m$-AA$_1$-AA$_2$-AA$_3$-AA$_4$-AA$_5$-AA$_6$-Y$_p$-Z$_q$-R$_2$          (I) (R$_1$-(SEQ ID NO:1)-R$_2$)

its stereoisomers, mixtures thereof and/or its cosmetically or pharmaceutically acceptable salts, wherein:

AA$_1$ is selected from the group formed by -Phe-, -Ser-, -Trp- and -Phg-;

AA$_2$ is selected from the group formed by -Met-, -Phe-, -Nle-, -Trp-, -Phg- and -Nva-;

AA$_3$ is selected from the group formed by -Arg-, -Gln-, -Trp-, -Lys-, -Orn-, -His-, -Cit-, -Asn- and -Phg-;

AA$_4$ is selected from the group formed by -Asp-, -Phe-, -Asn-, -Gln-, -Tyr-, -Trp- and -Phg-;

AA$_5$ is selected from the group formed by -His-, -Ile-, -Orn-, -Cit-, -Nle- and -Nva-;

AA$_6$ is selected from the group formed by -Ser-, -Val-, -Thr-, -Nle-, -Ile-, -Ala- and -Nva-;

W, X, Y, Z are amino acids and are independently selected from amongst themselves;

n, m, p and q are independently selected from amongst themselves and have a value of 0 or 1;

n+m+p+q is smaller or equal to 2;

R$_1$ is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

R$_2$ is selected from the group formed by —NR$_3$R$_4$, —OR$_3$ and —SR$_3$, wherein R$_3$ and R$_4$ are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and R$_1$ or R$_2$ are not α-amino acids.

Groups R$_1$ and R$_2$ are bound to the amino-terminal ends (N-terminal) and carboxy-terminal (C-terminal) of the peptide sequences respectively.

In accordance with a preferred embodiment of this invention R$_1$ is selected from the group formed by H or R$_5$—CO—, wherein R$_5$ is selected from the group formed by substituted or unsubstituted alkyl radical C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{24}$, substituted or unsubstituted cycloalkenyl C$_5$-C$_{24}$, substituted or unsubstituted cycloalkynyl C$_8$-C$_{24}$, substituted or unsubstituted aryl C$_6$-C$_{30}$, substituted or unsubstituted aralkyl C$_7$-C$_{24}$, substituted or unsubstituted heterocyclyl of 3-10 ring members, and substituted or unsubstituted heteroarylalkyl of 2 to 24 carbon atoms and 1 to 3 atoms other than carbon and an alkyl chain of 1 to 6 carbon atoms. More preferably, R$_1$ is selected from H, acetyl, tert-butanoyl, hexanoyl, 2-methyl-hexanoyl, cyclohexanecarboxyl, octanoyl, decanoyl, lauroyl myristoyl, palmitoyl, stearoyl, oleoyl and linoleoyl. Even more preferably, R$_1$ is H, acetyl, lauroyl, myristoyl or palmitoyl. In an even more preferred embodiment, R$_1$ is acetyl or palmitoyl.

In accordance with another preferred embodiment, R$_2$ is —NR$_3$R$_4$, —OR$_3$ or —SR$_3$ wherein R$_3$ and R$_4$ are independently selected from the group formed by H, substituted or unsubstituted alkyl C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{24}$, substituted or unsubstituted cycloalkenyl C$_5$-C$_{24}$, substituted or unsubstituted cycloalkynyl C$_8$-C$_{24}$, substituted or unsubstituted aryl C$_6$-C$_{30}$, substituted or unsubstituted aralkyl C$_7$-C$_{24}$, substituted or unsubstituted heterocyclyl of 3-10 ring members, and substituted or unsubstituted heteroarylalkyl of 2 to 24 carbon atoms and 1 to 3 atoms other than carbon wherein the alkyl chain is of 1 to 6 carbon atoms. Optionally, R$_3$ and R$_4$ can be bound by a saturated or unsaturated carbon-carbon bond, forming a cycle with the nitrogen atom. More preferably R$_2$ is —NR$_3$R$_4$ or —OR$_3$, wherein R$_3$ and R$_4$ are independently selected from the group formed by H, substituted or unsubstituted alkyl C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{10}$, substituted or unsubstituted aryl C$_6$-C$_{15}$ and substituted or unsubstituted heterocyclyl of 3-10 members, substituted or unsubstituted heteroarylalkyl with a ring of 3 to 10 members and an alkyl chain of 1 to 6 carbon atoms. More preferably R$_3$ and R$_4$ are selected from the group formed by H, methyl, ethyl, hexyl, dodecyl or hexadecyl. Even more preferably R$_3$ is H and R$_4$ is selected from the group formed by H, methyl, ethyl, hexyl, dodecyl, or hexadecyl. In accordance with an even more preferred embodiment, R$_2$ is selected from —OH and —NH$_2$.

In accordance with another embodiment of this invention R$_1$ is selected from the group formed by H, acetyl, lauroyl, myristoyl or palmitoyl, AA$_1$ is -L-Phe-, AA$_2$ is -L-Met-, AA$_3$ is -L-Trp-, AA$_4$ is -L-Phe-, AA$_5$ is -L-His-, AA$_6$ is -L-Val-, and R$_2$ is —NR$_3$R$_4$ or —OR$_3$ wherein R$_3$ and R$_4$ are independently selected from H, methyl, ethyl, hexyl, dodecyl and hexadecyl, preferably R$_2$ is —OH or —NH$_2$. More preferably, R$_1$ is acetyl or palmitoyl and R$_2$ is —NH$_2$. Even more preferably, n, m, p and q are 0.

In accordance with another embodiment of this invention R$_1$ is selected from the group formed by H, acetyl, lauroyl, myristoyl or palmitoyl, AA$_1$ is -L-Phe-, AA$_2$ is -L-Phe-, AA$_3$ is -L-Trp-, AA$_4$ is -L-Phe-, AA$_5$ is -L-His-, AA$_6$ is -L-Val- and R$_2$ is —NR$_3$R$_4$ or wherein R$_3$ and R$_4$ are independently selected from H, methyl, ethyl, hexyl, dodecyl and hexadecyl, preferably R$_2$ is —OH or —NH$_2$. More preferably, R$_1$ is acetyl or palmitoyl and R$_2$ is —NH$_2$. Even more preferably, n, m, p and q are 0.

In accordance with another embodiment of this invention R$_1$ is selected from the group formed by H, acetyl, lauroyl, myristoyl or palmitoyl, AA$_1$ is -L-Phe-, AA$_2$ is -L-Phe-, AA$_3$ is -L-Trp-, AA$_4$ is -L-Asp-, AA$_5$ is -L-Ile-, AA$_6$ is -L-Val-, and R$_2$ is —NR$_3$R$_4$ or —OR$_3$ wherein R$_3$ and R$_4$ are independently selected from H, methyl, ethyl, hexyl, dodecyl and hexadecyl, preferably R$_2$ is —OH or —NH$_2$. More preferably, R$_1$ is acetyl or palmitoyl and R$_2$ is —NH$_2$. Even more preferably, n, m, p and q are 0.

In accordance with another embodiment of this invention R$_1$ is selected from the group formed by H, acetyl, lauroyl, myristoyl and palmitoyl, preferably R$_1$ is selected from the group formed by H, acetyl and palmitoyl and R$_2$ is selected from the group formed by —OH and —NH$_2$.

In accordance with another embodiment of this invention n, m, p and q are 0.

Specifically, the Peptides which inhibit PAR-2 activity of the invention, represented according to the formula (I) are selected from the group of sequences outlined in Table 2, in which their sequence identifier is detailed:

TABLE 2

| SEQUENCE | IDENTIFIER |
|---|---|
| Phe-Met-Arg-Asp-His-Ser | SEQ ID NO: 2 |
| Phe-Met-Gln-Phe-His-Ser | SEQ ID NO: 3 |
| Phe-Phe-Gln-Phe-His-Ser | SEQ ID NO: 4 |
| Ser-Phe-Gln-Phe-His-Ser | SEQ ID NO: 5 |
| Phe-Met-Trp-Phe-His-Ser | SEQ ID NO: 6 |
| Ser-Met-Trp-Phe-His-Ser | SEQ ID NO: 7 |
| Phe-Phe-Trp-Phe-His-Ser | SEQ ID NO: 8 |

TABLE 2-continued

| SEQUENCE | IDENTIFIER |
|---|---|
| Ser-Phe-Trp-Phe-His-Ser | SEQ ID NO: 9 |
| Phe-Phe-Gln-Asp-Ile-Ser | SEQ ID NO: 10 |
| Phe-Met-Trp-Asp-Ile-Ser | SEQ ID NO: 11 |
| Phe-Phe-Trp-Asp-Ile-Ser | SEQ ID NO: 12 |
| Phe-Met-Arg-Phe-Ile-Ser | SEQ ID NO: 13 |
| Ser-Phe-Arg-Phe-Ile-Ser | SEQ ID NO: 14 |
| Phe-Met-Gln-Phe-Ile-Ser | SEQ ID NO: 15 |
| Ser-Met-Gln-Phe-Ile-Ser | SEQ ID NO: 16 |
| Phe-Phe-Gln-Phe-Ile-Ser | SEQ ID NO: 17 |
| Ser-Phe-Gln-Phe-Ile-Ser | SEQ ID NO: 18 |
| Phe-Met-Trp-Phe-Ile-Ser | SEQ ID NO: 19 |
| Ser-Met-Trp-Phe-Ile-Ser | SEQ ID NO: 20 |
| Phe-Phe-Trp-Phe-Ile-Ser | SEQ ID NO: 21 |
| Ser-Phe-Trp-Phe-Ile-Ser | SEQ ID NO: 22 |
| Phe-Phe-Arg-Asp-His-Val | SEQ ID NO: 23 |
| Phe-Phe-Trp-Asp-His-Val | SEQ ID NO: 24 |
| Phe-Met-Arg-Phe-His-Val | SEQ ID NO: 25 |
| Phe-Phe-Arg-Phe-His-Val | SEQ ID NO: 26 |
| Phe-Met-Gln-Phe-His-Val | SEQ ID NO: 27 |
| Ser-Met-Gln-Phe-His-Val | SEQ ID NO: 28 |
| Phe-Phe-Gln-Phe-His-Val | SEQ ID NO: 29 |
| Phe-Met-Trp-Phe-His-Val | SEQ ID NO: 30 |
| Ser-Met-Trp-Phe-His-Val | SEQ ID NO: 31 |
| Phe-Phe-Trp-Phe-His-Val | SEQ ID NO: 32 |
| Ser-Phe-Trp-Phe-His-Val | SEQ ID NO: 33 |
| Phe-Phe-Arg-Asp-Ile-Val | SEQ ID NO: 34 |
| Phe-Met-Gln-Asp-Ile-Val | SEQ ID NO: 35 |
| Phe-Phe-Gln-Asp-Ile-Val | SEQ ID NO: 36 |
| Phe-Met-Trp-Asp-Ile-Val | SEQ ID NO: 37 |
| Phe-Phe-Trp-Asp-Ile-Val | SEQ ID NO: 38 |
| Phe-Met-Arg-Phe-Ile-Val | SEQ ID NO: 39 |
| Ser-Met-Arg-Phe-Ile-Val | SEQ ID NO: 40 |
| Phe-Phe-Arg-Phe-Ile-Val | SEQ ID NO: 41 |
| Ser-Phe-Arg-Phe-Ile-Val | SEQ ID NO: 42 |
| Phe-Met-Gln-Phe-Ile-Val | SEQ ID NO: 43 |
| Ser-Met-Gln-Phe-Ile-Val | SEQ ID NO: 44 |
| Phe-Phe-Gln-Phe-Ile-Val | SEQ ID NO: 45 |
| Ser-Phe-Gln-Phe-Ile-Val | SEQ ID NO: 46 |
| Phe-Met-Trp-Phe-Ile-Val | SEQ ID NO: 47 |
| Ser-Met-Trp-Phe-Ile-Val | SEQ ID NO: 48 |
| Phe-Phe-Trp-Phe-Ile-Val | SEQ ID NO: 49 |
| Phe-Met-Asn-Trp-Ile-Nva | SEQ ID NO: 50 |
| Phe-Met-Asn-Tyr-Ile-Nva | SEQ ID NO: 51 |
| Phe-Met-Gln-Trp-Nva-Ile | SEQ ID NO: 52 |
| Phe-Met-Asn-Tyr-Nva-Ile | SEQ ID NO: 53 |
| Phe-Met-Gln-Trp-Nle-Ile | SEQ ID NO: 54 |
| Phe-Met-Gln-Phg-Nle-Ala | SEQ ID NO: 55 |
| Phe-Met-Gln-Tyr-Nle-Nle | SEQ ID NO: 56 |
| Phe-Met-Gln-Phg-Nva-Ala | SEQ ID NO: 57 |
| Phe-Met-Gln-Trp-Nva-Ala | SEQ ID NO: 58 |
| Phe-Trp-Gln-Phg-Ile-Nle | SEQ ID NO: 59 |
| Phe-Trp-Gln-Tyr-Nle-Nle | SEQ ID NO: 60 |
| Phe-Trp-Cit-Gln-Ile-Val | SEQ ID NO: 61 |
| Phe-Nle-Cit-Gln-Ile-Val | SEQ ID NO: 62 |
| Phe-Nle-His-Asn-Ile-Val | SEQ ID NO: 63 |
| Phe-Nva-His-Gln-IIe-Val | SEQ ID NO: 64 |
| Phe-Nva-Cit-Gln-Ile-Val | SEQ ID NO: 65 |
| Phe-Nva-His-Asn-Ile-Val | SEQ ID NO: 66 |
| Phe-Nva-Cit-Asn-Ile-Val | SEQ ID NO: 67 |
| Phe-Nle-Orn-Asp-Ile-Thr | SEQ ID NO: 68 |
| Phe-Nle-Lys-Asp-Ile-Val | SEQ ID NO: 69 |
| Phe-Phg-Orn-Asp-Cit-Thr | SEQ ID NO: 70 |
| Phe-Phg-Orn-Asp-Cit-Val | SEQ ID NO: 71 |
| Phe-Phg-Arg-Asp-Orn-Thr | SEQ ID NO: 72 |
| Phe-Phg-Lys-Asp-Cit-Val | SEQ ID NO: 73 |
| Phe-Phe-Lys-Asp-Cit-Thr | SEQ ID NO: 74 |
| Phe-Phe-Lys-Asp-Orn-Thr | SEQ ID NO: 75 |
| Phg-Phe-Lys-Asp-Orn-Val | SEQ ID NO: 76 |
| Phg-Phe-Phg-Asp-Orn-Val | SEQ ID NO: 77 |
| Phg-Phe-Phg-Asp-Ile-Nva | SEQ ID NO: 78 |
| Phg-Phe-Phg-Asp-Ile-Nle | SEQ ID NO: 79 |
| Trp-Phe-Phg-Asp-Ile-Ile | SEQ ID NO: 80 |
| Trp-Phe-Trp-Asn-Ile-Nva | SEQ ID NO: 81 |
| Trp-Phe-His-Gln-Ile-Val | SEQ ID NO: 82 |
| Trp-Trp-Asn-Asp-His-Val | SEQ ID NO: 83 |
| Gly-Phe-Phe-Trp-Phe-His-Val | SEQ ID NO: 84 |
| Phe-Phe-Trp-Phe-His-Val-Ala-Val | SEQ ID NO: 85 |
| Ile-Phe-Phe-Trp-Phe-His-Val-Gly | SEQ ID NO: 86 |

TABLE 2-continued

| SEQUENCE | IDENTIFIER |
|---|---|
| Ala-Gly-Phe-Phe-Trp-Phe-His-Val | SEQ ID NO: 87 |
| Phe-Phe-Trp-Phe-His-Val-Tyr | SEQ ID NO: 88 |
| Ala-Phe-Met-Trp-Phe-His-Val | SEQ ID NO: 89 |
| Phe-Met-Trp-Phe-His-Val-Ala-Gly | SEQ ID NO: 90 |
| Ala-Leu-Phe-Met-Trp-Phe-His-Val | SEQ ID NO: 91 |
| Phe-Met-Trp-Phe-His-Val-Val | SEQ ID NO: 92 |
| Gly-Phe-Met-Trp-Phe-His-Val-Gly | SEQ ID NO: 93 |
| Ala-Phe-Phe-Trp-Asp-Ile-Val | SEQ ID NO: 94 |
| Phe-Phe-Trp-Asp-Ile-Val-Gly-Gly | SEQ ID NO: 95 |
| Ile-Phe-Phe-Trp-Asp-Ile-Val-Ile | SEQ ID NO: 96 |
| Thr-Gly-Phe-Phe-Trp-Asp-Ile-Val | SEQ ID NO: 97 |
| Phe-Phe-Trp-Asp-Ile-Val-Tyr | SEQ ID NO: 98 | their stereoisomers, mixtures thereof and/or their cosmetically or pharmaceutically acceptable salts.

The peptides of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the peptides of the invention are pure isomers, i.e., enantiomers or diastereomers.

For example, when it is stated that AA, can be -Ser-, it is understood that AA, is selected from -L-Ser-, -D-Ser- or mixtures of both, racemic or non-racemic. The preparation processes described in this document enable the person skilled in the art to obtain each of the stereoisomers of the peptide of the invention by choosing the amino acid with the right configuration.

In the context of this invention, the term "amino acids" includes the amino acids codified by the genetic code as well as uncodified amino acids, whether they are natural or not. Examples of non-codified amino acids are, without restriction, citrulline, ornithine, sarcosine, desmosine, norvaline, 4-aminobutyric acid, 2-aminobutyric acid, 2-aminoisobutyric acid, 6-aminohexanoyc acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, α-amino acids and β-amino acids, among others, as well as their derivatives. A list of unnatural amino acids can be found in the article "Unusual amino acids in peptide synthesis" by D. C. Roberts and F. Vellaccio, in The Peptides, Vol. 5 (1983), Chapter VI, Gross E. and Meienhofer J., Eds., Academic Press, New York, USA or in the commercial catalogues of the companies specialized in the field.

In the context of this invention, when n, m, p or q are not 0 it is clearly understood that the nature of W, X, Y and/or Z does not hinder the activity of the peptides of the invention, but contributes to the inhibition of PAR-2 activity or has no effect on it.

The cosmetically and pharmaceutically acceptable salts of the peptides provided by this invention are also found within the field of this invention. The term "cosmetically or pharmaceutically acceptable salts" means a salt recognized for its use in animals and more specifically in human beings, and includes salts used to form base addition salts, whether they are inorganic, for example and not restricted to, lithium, sodium, potassium, calcium, magnesium, manganese, copper, zinc or aluminum among others, whether they are organic, for example and not restricted to, ethylamine, diethylamine, ethylenediamine, ethanolamine, diethanolamine, arginine, lysine, histidine or piperazine among others, or acid addition salts, whether they are organic, for example and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, for example and not restricted to, chloride, sulfate, borate or carbonate, among others. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al, "*Pharmaceutical Salts*", (1977), *J. Pharm. Sci.*, 66, 1-19].

Another aspect of this invention relates to a peptide of general formula (I), its stereoisomers, mixtures thereof and/or its cosmetically or pharmaceutically acceptable salts, as described in this invention, for its use in the inhibition of PAR-2 activity.

In another particular aspect, this invention relates to a peptide of general formula (I), its stereoisomers, mixtures thereof and/or its cosmetically or pharmaceutically acceptable salts, as described in this invention, for its use in medicine.

In another particular aspect, this invention relates to a peptide of general formula (I), its stereoisomers, mixtures thereof and/or its cosmetically or pharmaceutically acceptable salts, as described in this invention, for its use in the treatment and/or prevention of itching, inflammation, pain, diseases and/or disorders of the airways.

In a preferred embodiment, the itching is selected from the itching associated with conditions, diseases and/or disorders, for example and not restricted to, dermatitis, atopic dermatitis, contact dermatitis, diaper dermatitis, dermatitis herpetiform is, photodermatosis, photosensitivity, dermatosis related to pregnancy, dermatosis related to menopause, eczema, sensitive skin, psoriasis, chickenpox, herpes, herpes zoster, Netherton's syndrome, peeling skin syndrome, lichen planus, acne, dandruff, seborrhea, seborrheic dermatitis, alopecia, athlete's foot, candidiasis, hemorrhoids, vaginal itching, pruritus ani, anogenital pruritus, sunburn, urticaria, pruritic otitis, senile pruritus, aquagenic pruritus, prurigo nodularis, prurigo planus, pityriasis rosea, xerosis and dry skin, or pruritus associated with dialysis, HIV infection, malignant neoplasms, Hodgkin's disease, leukemia, myeloma, lymphoma, solid tumors, adenocarcinomas, lung cancer, hepatic diseases, jaundice, cholestasis, liver failure, cirrhosis, polycythemia, hypereosinophilic syndrome, primary thrombocythemia, myelodysplastic syndrome, anemia due to iron deficiency, systemic lupus erythematosus, endocrine diseases, thyroid diseases, hyperthyroidism, hypothyroidism, parathyroid diseases, diabetes mellitus, kidney diseases, kidney failure, uremia, parasitic diseases, scabies, lice, intestinal worms, allergic reactions, allergies to medication, food allergies, allergies to chemical products, exposure to poisonous plants, exposure to insect bites, chemotherapy, stress and anxiety, among others.

In another particular embodiment, the pain is selected, for example and not restricted to, from the group formed by acute pain, chronic pain, nociceptive pain, neuropathic pain, inflammatory pain, visceral pain, abdominal pain, digestive system pain, respiratory system pain, urogenital system pain, endocrine system pain, heart pain, pancreatic pain, hepatic pain, pain due to gallstones, cholestasis, intestinal pain, stomach pain, pain due to duodenal ulcers, pain due to esophagitis, pain due to gastroesophageal reflux disease, spleen pain, pain in the blood vessels, thalamic syndrome pain, irritable bowel syndrome, pain associated with Crohn's disease, pain associated with ulcerative colitis, diverticulitis, gastrointestinal mucositis, headaches, tension headaches, headache associated with sinusitis, migraines, eye pain, dry eye syndrome, postoperative pain, postoperative pain due to surgical incisions, postoperative pain due to implant insertions in the bone, postoperative pain due to bone substitutions, postoperative pain due to infections, postoperative pain due to limb amputations, pain due to bone fractures, pain due to cancer, pain due to bone cancer, pain associated with benign bone tumors, pain associated with osteoid osteomas, pain associated with osteoblastomas, pain due to cancer treatment, pain due to chemotherapy, pain due to emesis, pain due to emesis resulting from chemotherapy treatment, musculoskeletal pain, spastic muscle pain, fibromyalgia, complex regional pain syndrome, psychogenic pain, neuralgic pain, pain due to demyelinating diseases, neck pain associated with cervical dystonia, back pain, lumbago, sciatica, neurogenic inflammation, neuritis, causalgia, touch sensitivity, cold sensitivity, heat sensitivity, skin irritation, post-hair removal skin irritation, post-shaving skin irritation, psoriasis, sensitive skin, dermatitis, atopic dermatitis, contact dermatitis, diaper dermatitis, seborrheic dermatitis, eczema, lichen planus, burns, sunburn, arthritis, rheumatoid arthritis, osteoarthritis, psoriatic arthritis, uveitis, pain due to nerve damage, neuralgia, postherpetic neuralgia, neuropathies, peripheral neuropathies, phantom pains, allodynia, hyperalgesia, cold hyperalgesia, pain due to carpal tunnel syndrome, burning pain, Grierson-Gopalan syndrome (better known as burning feet syndrome), burning mouth syndrome, paresthesia, Fabry's disease, facial pain, trigeminal neuralgia, neuropathic pain due to diabetes, neuropathic pain due to AIDS, orofacial pain, dental pain, pain due to tooth removal, pain due to removal of a wisdom tooth, tooth sensitivity to the cold, tooth sensitivity to heat, oral mucositis, temporomandibular joint pain, joint pain caused by gout, pain associated with tattoo or tattoo removal processes, bunion pain, testicular pain, myofascial pain, urinary bladder pain, urinary tract pain, cystitis, pain due to kidney stones, renal colic, vulval pain, vaginal pain, post-birth pain, menstrual pain, scrotal pain, perineum pain, pelvic pain or hypersensitivity, skin pain or irritation after surgery, after treatment with intense pulsed light therapy (IPL), after treatment with monochromatic pulsed light therapy (laser), after treatment with chemical peeling agents or after overexposure to aggressive external agents and pain due to chronic alcohol abuse.

In another particular aspect, the inflammation is selected, for example and not restricted to, from the group formed by neurogenic inflammation, joint inflammation, tendon inflammation, muscular inflammation, sepsis, vascular inflammation, respiratory inflammation, chronic obstructive pulmonary disease, rhinitis, allergic rhinitis, asthma, otitis, intestinal inflammation, Crohn's disease, pancreatitis, hepatitis, conditions related to chronic inflammation, acute inflammation, nephritis, systemic lupus erythematosus, arthritis, rheumatoid arthritis, adult and juvenile rheumatoid arthritis, Still's disease, psoriatic arthritis, osteoarthritis, arthritis caused by gout, rheumatoid spondylitis, glom erulonephritis, neuritis, nerve tissue inflammation, multiple sclerosis, immune system disorders, Sjögren's syndrome, atherosclerosis, myocarditis, pericarditis, vasculitis, inflammatory skin conditions, psoriasis, sensitive skin, dermatitis, atopic dermatitis, contact dermatitis, diaper dermatitis, seborrheic dermatitis, eczema, hyperproliferative skin disease, burns, sunburn, inflammation of the vaginal mucus, vulvodynia, vaginitis, inflammation of the oral mucosa, gingivitis, periodontitis, inflammatory eye diseases, uveitis, ocular and vernal conjunctivitis, sarcoidosis, peptic ulcers, urticaria, bullous pemphigoid, scleroderma, fibrosis, angioedema, anaphylaxis, alopecia, cirrhosis of the liver, restenosis, polymyalgia rheumatica, seronegative spondyloarthropathy, including ankylosing spondylitis and Reiter's syndrome, dermatomyositis, inclusion body myositis, polymyositis and lymphangioleiomyomatosis.

In another particular embodiment the diseases and/or disorders of the respiratory airways are selected, for example and not restricted to, from the group formed by asthma, chronic obstructive pulmonary disease, allergic rhinitis and bronchial hyperreactivity.

In another particular aspect, this invention relates to a peptide of general formula (I), its stereoisomers, mixtures thereof and/or its cosmetically or pharmaceutically acceptable salts, as described in this invention, for its use in the treatment of cancer.

In another particular embodiment, the cancer is selected, for example and not restricted to, from the group formed by lymphoreticular neoplasms, bone cancer, osteosarcoma, liposarcoma, breast cancer, stomach cancer, pancreatic cancer, bladder cancer, bowel cancer, endometrial cancer, cancer of the uterus, head and neck cancer, lung cancer, cancer of the respiratory airways, melanoma, ovarian cancer, prostate cancer, skin cancer and rectal cancer, among others.

In another particular aspect, this invention relates to a peptide of general formula (I), its stereoisomers, mixtures thereof and/or its cosmetically or pharmaceutically acceptable salts, as described in this invention, for the treatment and/or care of conditions, disorders and/or diseases of the digestive system.

In another particular aspect, the conditions, disorders and/or diseases of the digestive system are selected, for example and not restricted to, from the group formed by celiac disease, food allergies, Crohn's disease, gastroenteritis, inflammatory intestinal disease, intestinal colic, hepatitis, colitis, ulcerative colitis, irritable bowel syndrome, esophagitis, gastroesophageal reflux disease, idiopathic gastroparesis, pancreatitis including chronic pancreatitis, and gastric and duodenal ulcers.

Another aspect of this invention refers to a peptide of general formula (I), its stereoisomers, mixtures thereof and/or its cosmetically or pharmaceutically acceptable salts, as described in this invention, for its use in the treatment and/or care of the skin and mucous membranes.

In another particular aspect, this invention relates to a peptide of general formula (I), its stereoisomers, mixtures thereof and/or its cosmetically or pharmaceutically acceptable salts, as described in this invention, for its use in the stimulation and/or care of the skin barrier function.

In another particular aspect, this invention relates to a peptide of general formula (I), its stereoisomers, mixtures thereof and/or its cosmetically or pharmaceutically acceptable salts, as described in this invention, for its use in the re-reepithelization and/or healing of the skin and/or mucous membranes.

In another particular aspect, this invention relates to a peptide of general formula (I), its stereoisomers, mixtures thereof and/or its cosmetically or pharmaceutically acceptable salts, as described in this invention, for its use in the depigmentation and/or photoprotection of the skin or in the treatment and/or care of those skin conditions, disorders and/or diseases which improve or are prevented by the reduction of the pigmentation of the skin or by photoprotection of the skin.

In another particular aspect, the skin conditions, disorders and/or diseases which improve or are prevented by the reduction of pigmentation or by photoprotection are selected, for example and not restricted to, from the group formed by freckles, lentigo, melasma, piebaldism, Addison's disease, vitiligo, marks due to exposure to UV radiation, marks due to aging or photoaging, marks caused by inflammation, and in particular inflammation due to laser or IPL treatment or post-aesthetics surgery, marks from acne, eczema, ochronosis, marks due to scars and/or hormonal disturbances such as chloasmas and melasmas.

In another particular aspect, this invention refers to a peptide of general formula (I), its stereoisomers, mixtures thereof and/or its cosmetically or pharmaceutically acceptable salts, as described in this invention, for its use in the treatment of the scalp and/or in capillary hygiene, and in particular for its use in the treatment and/or care of alopecia, dandruff and/or seborrheic dermatitis.

In another particular aspect, this invention refers to a peptide of general formula (I), its stereoisomers, mixtures thereof and/or its cosmetically or pharmaceutically acceptable salts, as described in this invention, for its use in the treatment of oral mucosa and/or in oral hygiene, and in particular for its use in the treatment and/or care of periodontitis and/or gingivitis.

In another particular aspect, this invention refers to a peptide of general formula (I), its stereoisomers, mixtures thereof and/or its cosmetically or pharmaceutically acceptable salts, as described in this invention, for its use in the treatment of vaginal mucus and/or intimate hygiene, and in particular for its use in the treatment and/or care of candidiasis, vaginal itching, pruritus ani, anogenital pruritus and/or hemorrhoids.

In another particular aspect, this invention refers to a peptide of general formula (I), its stereoisomers, mixtures thereof and/or its cosmetically or pharmaceutically acceptable salts, as described in this invention, for its use in the inhibition of skin sensitizing agents, and particularly allergens in cosmetic compositions.

In another particular aspect, this invention refers to a peptide of general formula (I), its stereoisomers, mixtures thereof and/or its cosmetically or pharmaceutically acceptable salts, as described in this invention, which is applied by topical, transdermal, oral or parenteral route.

In another particular aspect, this invention refers to a peptide of general formula (I), its stereoisomers, mixtures thereof and/or its cosmetically or pharmaceutically acceptable salts, as described in this invention, in which the topical or transdermal application is carried out by iontophoresis, sonophoresis, electroporation, mechanical pressure, osmotic pressure gradient, occlusive cure, microinjections, by needle-free injections by means of pressure, by microelectric patches, face masks o or any combination thereof.

In another particular aspect, the treatment and/or care is carried out by oral administration.

Preparation Processes of the Peptides of the Invention

Synthesis of the peptides of the invention, their stereoisomers, mixtures thereof and/or their cosmetically or pharmaceutically acceptable salts can be carried out according to conventional methods, known in the prior art, such as using solid phase peptide synthesis methods [Stewart J. M. and Young J. D., "Solid Phase Peptide Synthesis, 2nd edition", (1984), Pierce Chemical Company, Rockford, Ill.; Bodanzsky M. and Bodanzsky A., "The practice of Peptide Synthesis", (1994), Springer Verlag, Berlin; Lloyd-Williams P. et al., "Chemical Approaches to the Synthesis of Peptides and Proteins", (1997), CRC, Boca Raton, Fla., USA], synthesis in solution, a combination of the methods of solid phase synthesis and synthesis in solution or enzymatic synthesis [Kullmann W. "Proteases as catalysts for enzymic syntheses of opioid peptides", (1980), J. Biol. Chem., 255(17), 8234-8238]. The peptides can also be obtained by fermentation of a bacterial strain, modified or unmodified, by genetic engineering to produce the desired sequences, or by controlled hydrolysis of proteins with animal or plant origins, preferably plant, which release peptide fragments which contain, at least, the desired sequence.

For example, a method of obtaining the peptides (I) of the invention, their stereoisomers and mixtures thereof comprises the stages of:

coupling of an amino acid, with the N-terminal end protected and the C-terminal end free, with an amino acid with the N-terminal end free and the C-terminal end protected or bound to a solid carrier;

elimination of the protective group of the N-terminal end;

repetition of the coupling sequence and elimination of the protective group of the N-terminal end until the desired peptide sequence is obtained;

elimination of the protective group of the C-terminal end or cleavage of the solid carrier.

Preferably, the C-terminal end is bound to a solid carrier and the process is carried out in solid phase and, therefore, comprises the coupling of an amino acid with the N-terminal end protected and the C-terminal end free with an amino acid with the N-terminal end free and the C-terminal end bound to a polymer carrier; elimination of the protective group of the N-terminal end; and repetition of this sequence as many times as is necessary to thus obtain the peptide of the desired length, finally followed by the cleavage of the synthesized peptide of the original polymeric carrier.

The functional groups of the side chains of the amino acids are maintained conveniently protected with temporary or permanent protective groups throughout synthesis, and can be unprotected simultaneously or orthogonally to the process of cleavage of the peptide of the polymeric carrier.

Alternatively, solid phase synthesis can be carried out using a convergent strategy coupling a peptide with the polymeric carrier or with an amino acid previously bound to the polymeric carrier. Convergent synthesis strategies are widely known by persons skilled in the art and are described in Lloyd-Williams P. et al., "Convergent Solid-Phase Peptide Synthesis", (1993), Tetrahedron, 49(48), 11065-11133.

The procedure can comprise the additional stages of deprotection of the N-terminal and C-terminal ends and/or cleavage of the peptide of the polymeric carrier in an indiscriminant order, using standard processes and conditions known in the prior art, after which the functional groups of these ends can be modified. The optional modification of the N-terminal and C-terminal ends can be carried out with the peptide of formula (I) anchored to the polymeric carrier or once the peptide has been separated from the polymeric carrier.

Optionally, $R_1$ can be introduced by the reaction of the N-terminal end of the peptide of the invention with a $R_1$—X compound, wherein $R_1$ has the aforementioned meaning and X is a leaving group, for example and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric carrier.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N41-(4,4-dimethyl-2,6-dioxocyclohex-1-ylidene)ethyl (Dde), 1-(4,4-dimethyl-2,6-dioxocyclohexylidene)-3-methyl-butyl (ivDde), 1-(1-adamantyl)-1-methylethoxycarbonyl (Adpoc), among others; preferably Boc or Fmoc.

Examples of representative protective groups for the carboxyl group are esters, such as the tert-butyl (tBu) ester, allyl (All) ester, triphenylmethyl ester (Trt ester), cyclohexyl (cHx) ester, benzyl (Bzl) ester, ortho-nitrobenzyl ester, para-nitrobenzyl ester, para-methoxybenzyl ester, trimethylsilylethyl ester, 2-phenylisopropyl ester, fluorenylmethyl (Fm) ester, 4-(N-[1-(4,4-dimethyl-2,6-dioxocyclohexylidene)-3-methylbutyl]amino)benzyl (Dmab) ester, among others; preferred protective groups of the invention are the All, tBu, cHex, Bzl and Trt esters.

The side chains of the trifunctional amino acids can be protected during the synthetic process with temporary or permanent protective groups orthogonal to the protective groups of the N-terminal and C-terminal ends.

The hydroxyl group of the tyrosine side chain can be protected with the 2-bromobenzyloxycarbonyl group (2-BrZ), tBu, All, Bzl or 2,6-dichlorobenzyl (2,6-diClZ) among others. The threonine and serine side chains are protected by a protective group selected from the group formed by tBu, Bzl, Trt and Ac. The histidine side chain is protected by a protective group selected from the group formed by Tos, Dnp, methyl (Me), Boc, benzyloxymethyl (Bom), Bzl, Fmoc, Mts, Trt and Mtt. The amide group of the glutamine and asparagine side chain can be protected by the Trt group or the xanthyl group (Xan) or can be used unprotected. For the protection of the carboxyl group of the aspartic acid side chain esters can be used such as tBu ester, All ester, triphenylmethyl ester (Trt ester), cHx ester, Bzl ester, ortho-nitrobenzyl ester, para-nitrobenzyl ester, para-metoxybenzyl ester, trimethylsilylethyl ester, 2-phenylisopropyl ester, Fm ester or Dmab ester, among others. The arginine side chain is protected by a protective group selected from the group formed by Tos, 4-methoxy-2,3,6-trimethylbenzenesulfonyl (Mtr), Alloc, nitro, 2,2,4,6,7-pentamethyldihydrobenzofuran-5-sulfonyl (Pbf) and 2,2,5,7,8-pentamethylchroman-6-sulfonyl (Pmc). The indole group of the tryptophan side chain can be protected by the formyl group (For), Boc, Mts or be used unprotected. For the protection of the amino groups of the lysine and ornithine side chains amides can be used, such as amide acetate, amide benzoate, amide pivalate; carbamates, such as Cbz or Z, ClZ, pNZ, Boc, Troc, Teoc, Fmoc or Alloc, Trt, Mtt, Dnp, Dde, ivDde, Adpoc, among others. The methionine side chain can be protected in sulfoxide form or be used unprotected.

In a preferred embodiment, the protective group strategy used is the strategy wherein the amino groups are protected by Boc, the carboxyl groups are protected by Bzl, cHx or All esters, the tyrosine side chain is protected with 2-BrZ or Bzl, the serine and threonine side chains are protected by the Bzl group, the histidine side chain is protected by the Tos or Bom group, the aspartic acid side chain is protected by Bzl, cHx or All, glutamine and asparagine are used unprotected in their side chain, methionine is used unprotected in its side chain, the arginine side chain is protected by Tos, the tryptophan side chain is protected by For or Mts and the lysine and ornithine side chains are protected by ClZ, Fmoc or Alloc.

In another preferred embodiment, the protective group strategy used is the strategy wherein the amino groups are protected by Fmoc, the carboxyl groups are protected by tBu, All or Trt esters, the tyrosine side chain is protected by tBu, and the serine and threonine side chains are protected by the tBu group, the histidine side chain is protected by the Trt or Mtt group, the aspartic acid side chain is protected by tBu or All, glutamine and asparagine are used protected by the Trt group in its side chain, methionine is used unprotected in its side chain, the arginine side chain is protected by Pmc or Pbf, the tryptophan side chain is protected by Boc or used unprotected, and the lysine and ornithine side chains are protected by Boc, Trt or Alloc.

Examples of these and additional protective groups, their introduction and elimination, can be found in the literature [Atherton B. and Sheppard R. C., "*Solid Phase Peptide Synthesis: A practical approach*", (1989), IRL Oxford University Press]. The term "protective groups" also includes the polymeric carriers used in solid phase synthesis.

When synthesis takes place totally or partially in solid phase, the possible solid carriers used in the procedure of the invention involve polystyrene carriers, polyethylene glycol grafted to polystyrene and similar, for example and not restricted to, p-methylbenzhydrylamine resins (MBHA) [Matsueda G. R. et al., "*A p-methylbenzhydrylamine resin for improved solid-phase synthesis of peptide amides*", (1981), *Peptides*, 2, 45-50], 2-chlorotrityl resins [Barlos K. et al., "*Darstellung geschützter Peptid-Fragmente unter Einsatz substituierter Triphenylmethyl-Harze*", (1989), *Tetrahedron Lett.*, 30, 3943-3946; Barlos K. et al., "*Veresterung von partiell geschützten Peptid-Fragmenten mit Harzen. Einsatz von 2-Chlorotritylchlorid zur Synthese von Leu1-Gastrin I*", (1989), *Tetrahedron Lett.*, 30, 3947-3951], TentaGel resins (Rapp Polymere GmbH), ChemMatrix resins (Matrix Innovation, Inc) and similar, which may or may not include a labile linker, such as 5-(4-aminomethyl-3,5-dimethoxyphenoxy) valeric acid (PAL) [Albericio F. et al., "*Preparation and application of the 5-(4-(9-fluorenylmethyloxycarbonyl) aminomethyl-3,5-dimethoxy-phenoxy)valeric acid (PAL) handle for the solid-phase synthesis of C-terminal peptide amides under mild conditions*", (1990), *J. Org. Chem.*, 55, 3730-3743], 2-[4-aminomethyl-(2,4-dimethoxyphenyl)] phenoxyl acetic acid (AM) [Rink H., "*Solid-phase synthesis of protected peptide fragments using a trialkoxy-diphenyl-methylester resin*", (1987), *Tetrahedron Lett.*, 28, 3787-3790], Wang [Wang S. S., "*p-Alkoxybenzyl Alcohol Resin and p-Alkoxybenzyloxycarbonylhydrazide Resin for Solid Phase Synthesis of Protected Peptide Fragments*"; (1973), *J. Am. Chem. Soc.*, 95, 1328-1333] and similar, which enable simultaneous deprotection and cleavage of the peptide from the polymeric carrier.

Cosmetic or Pharmaceutical Compositions of the Invention

The peptides of the invention can be administered to inhibit PAR-2 activity by any means which causes contact between the peptides and the site of action in a mammal's body, preferably that of a human being, and in the form of a composition which contains them.

To this regard, another aspect of the invention is a cosmetic or pharmaceutical composition which comprises at least one peptide of general formula (I), its stereoisomers, mixtures thereof, and/or its cosmetically or pharmaceutically acceptable salts together with at least one cosmetically or pharmaceutically acceptable adjuvant or excipient. These compositions can be prepared by conventional means known to persons skilled in the art ["*Harry's Cosmeticology*", *Seventh edition*, (1982), Wilkinson J. B., Moore R. J., ed. Longman House, Essex, GB].

The peptides of this invention have variable solubility in water, according to the nature of their sequence or any possible modifications in the N-terminal and/or C-terminal ends. Therefore, the peptides of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerine, butylene glycol or polyethylene glycol or any combination thereof.

The cosmetically or pharmaceutically effective amount of the peptides of the invention which should be administered, as well as their dosage, will depend on numerous factors, including age, state of the patient, the nature or severity of the condition, disorder or disease to be treated and/or cared for, the route and frequency of administration and of the particular nature of the peptides to be used.

"Cosmetically and pharmaceutically effective amount" is understood to mean a non-toxic but sufficient amount of the peptide or peptides of the invention to provide the desired effect. The peptides of the invention are used in the cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.00001% (in weight) and 10% (in weight) and even more preferably between 0.001% (in weight) and 5% (in weight).

The peptides of the invention or their functionally equivalent variants, their stereoisomers, mixtures thereof and/or their cosmetic or pharmaceutically acceptable salts, can also be incorporated into cosmetic or pharmaceutical delivery systems and/or sustained release systems.

The term "delivery systems" relates to a diluent, adjuvant, excipient or carrier with which the peptide of the invention is administered. These cosmetic or pharmaceutical carriers can be liquids, such as water, oils or surfactants, including those of petroleum, animal, plant or synthetic origin, for example and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the peptide of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the peptides of the invention. The amount of peptide contained in the sustained release system will depend, for example, on where the composition is to be administered, the kinetics and duration of the release of the peptide of the invention, as well as the nature of the condition, disorder and/or disease to be treated and/or cared for.

The peptides of this invention can also be adsorbed on solid organic polymers or solid mineral supports such as and not restricted to, talc, bentonite, silica, starch or maltodextrin among others.

The compositions which contain the peptides of the invention, their stereoisomers, mixtures thereof and/or their cosmetically or pharmaceutically acceptable salts can also be incorporated into fabrics, non-woven fabrics and medical devices which are in direct contact with the skin, thus releasing the peptides of the invention whether by biodegradation of the binding system to the fabric, non-woven fabric or medical device, or by friction between them and the body, due to body moisture, the skin's pH or body temperature. Furthermore, the peptides of the invention can be incorporated into the fabrics and non-woven fabrics used to make garments that are in direct contact with the body. Preferably, the fabrics, non-woven fabrics and medical devices containing the peptides of the invention are used for the treatment and/or care of conditions, disorders and/or diseases which improve or are prevented by in inhibition of PAR-2 activity.

Examples of fabrics, non-woven fabrics, garments, medical devices and means for immobilizing the peptides to them, among which are the delivery systems and/or the sustained release systems described above, can be found in literature and are known in the prior art [Schaab C. K. (1986) HAPPI May 1986; Nelson G., "*Application of microencapsulation in textiles*", (2002), *Int. J. Pharm.*, 242(1-2), 55-62; *"Biofunctional Textiles and the Skin"* (2006) *Curr. Probl, Dermatol.* v. 33, Hipler U. C. and Elsner P., eds. S. Karger A G, Basel, Switzerland; Malcolm R. K. et al., "*Controlled release of a model antibacterial drug from a novel self-lubricating silicone biomaterial*", (2004), *J. Cont. Release,* 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the peptides of this invention, their stereoisomers, mixtures thereof and/or their cosmetically or pharmaceutically acceptable salts, can be used in different types of compositions of topical or transdermal application which optionally include cosmetically or pharmaceutically acceptable excipients necessary for formulating the desired administration form. A person skilled in the art knows the different excipients which can be used in the cosmetic or pharmaceutical compositions which contain the peptides of the invention.

The compositions of topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories for example and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic or pharmaceutical compositions of the invention may include agents which increase the percutaneous absorption of the peptides of this invention, for example and not restricted to, dimethylsulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the cosmetic compositions containing the peptides of this invention, their stereoisomers and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, tablets, pills, powders, granules, chewing gum, solutions, suspensions, emulsions, syrups, elixirs, polysaccharide films, jellies or gelatins, and any other form known by the person skilled in the art. In particular, the peptides of the invention can be incorporated into any form of functional food or fortified food, such as and not restricted to, dietary bars or compact or non-compact powders. These powders can be dissolved in water, soda, dairy products, soy derivatives or can be incorporated into dietary bars. The peptides of this invention can be formulated with common excipients and adjuvants for oral compositions or food supplements, for example and not restricted to, fat components, aqueous components, humectants, preservatives, texturizing agents, flavors, aromas, antioxidants and colorants common in the food industry.

Cosmetic or pharmaceutical compositions containing the peptides of the invention, their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal route, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the peptides of the invention can be administered.

Among the cosmetically or pharmaceutically acceptable adjuvants contained in the cosmetic or pharmaceutical compositions described in this invention are additional ingredients commonly used in cosmetic or pharmaceutical compositions, for example and not restricted to, other agents which inhibit PAR-2 activity, other anti-inflammatory and/or analgesic agents, other anti-itching agents, calming agents, anesthetic agents, inhibitors of acetylcholine-receptor aggregation, agents inhibiting muscular contraction, anticholinergic agents, melanin synthesis stimulating or inhibiting agents, whitening or depigmenting agents, propigmenting agents, self-tanning agents, antiaging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances which retain moisture, alpha hydroxyacids, beta hydroxyacids, moisturizers, hydrolytic epidermal enzymes, vitamins, amino acids, proteins, pigments or colorants, dyes, biopolymers, gelling polymers, thickening agents, surfactants, softening agents, emulsifiers, binding agents, preservatives, anti-wrinkle agents, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, aquaporin synthesis-stimulating agents, hyaluronic acid synthesis-stimulating agents, fibronectin synthesis-stimulating agents, sirtuin synthesis-stimulating agents, heat shock proteins, heat shock protein synthesis-stimulating agents, agents stimulating the synthesis of lipids and components of the stratum corneum, ceramides, fatty acids, agents that inhibit collagen degradation, agents inhibiting matrix metalloproteinase, agents that inhibit elastin degradation, agents that inhibit serine proteases such as cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, agents inhibiting acetylcholinesterase, skin relaxant agents, glycosaminoglycan synthesis-stimulating agents, anti-hyperkeratosis agents, comedolytic agents, anti-psoriatic agents, DNA repair agents, DNA protecting agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1α synthesis, agents modulating the activity of PPARγ, agents which increase or reduce the triglyceride content of adipocytes, anti-cellulite agents, antiperspirant agents, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays or mixtures thereof, provided that they are physically and chemically compatible with the rest of components in the composition and particularly with the peptides of the invention. Likewise, the nature of these additional ingredients should not unacceptably alter the benefits of the peptides of this invention. The nature of these additional ingredients can be synthetic or natural, such as plant extracts, or come from a biotechnological process, or from a combination of a synthetic process and a biotechnological process. Additional examples can be found in CTFA International Cosmetic Ingredient Dictionary & Handbook, 12th Edition (2008). In the context of this invention, biotechnological process is understood to be any process to produce the active ingredient, or part of it, in an organism, or in part of it.

An additional aspect to this invention refers to a cosmetic or pharmaceutical composition which comprises a cosmetically or pharmaceutically effective quantity of at least one peptide according to the general formula (I), its stereoisomers, mixtures thereof and/or its cosmetically or pharmaceutically acceptable salts, as well as a cosmetically or pharmaceutically effective quantity of at least one extract, synthetic compound or product of biotechnological origin which is an anti-wrinkle agent and/or antiaging agent for example and not restricted to the extracts or hydrolized extracts of *Vitis vinifera, Rosa canina, Curcuma longa, Theobroma cacao, Ginkgo biloba, Leontopodium alpinum* or *Dunaliella salina* among others, Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: calcium hydroxymethionine], Renovage [INCI: teprenone], Resistem™ [INCI: *Globularia Cordifolia* Ferment] or Dermaxyl® [INCI: Palmitoyl Oligopeptide] marketed by Sederma/Croda, Vialox® [INCI: Pentapeptide 3], Syn® Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum] or Preregen® [INCI: *Glycine soja* (Soybean) Protein, Oxido Reductases] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9] or DN AGE™ LS [INCI: *Cassia alata* leaf Extract] marketed by Laboratoires Sérobiologiques/Cognis, Algisum [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI: Acetyl Hexapeptide-30], Aldenine® [INCI: Hydrolized Wheat Protein, Hydrolized Soy Protein, Tripeptide-1], Preventhelia™ [INCI: Diaminopropionoyl Tripeptide-33], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase™ [INCI: Acetylarginyltriptophyl Diphenylglycine], Thermostressine® [INCI: Acetyl Tetrapeptide-22], Lipochroman-6 [INCI: Dimethylmethoxy Chromanol], Chromabright™ [INCI: Dimethylmethoxy Chromanyl Palmitate], Antarcticine® [INCI: *Pseudoalteromonas* Ferment Extract], dGlyage™ [INCI: Lysine HCl, Lecithin, Tripeptide-9 Citrulline], Vilastene™ [INCI: Lysine HCl, Lecithin, Tripeptide-10 Citrulline], Hyadisine™ [INCI: *Pseudoalteromonas* Ferment Extract], Diffuporine™[INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Adifyline™ [INCI: Acetyl Hexapeptide-38] marketed by Lipotec, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract] or Quintescine™ IS [INCI: Dipeptide-4] marketed by Vincience/ISP, BONT-L-Peptide [INCI:

Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: *Pyrus malus* Fruit Extract, *Glycine soja* Seed Extract] or Juvenesce [INCI: Ethoxydiglicol and Caprylic Triglyceride, Retinol, Ursolic Acid, Phytonadione, Ilomastat] marketed by Coletica/Engelhard/BASF, Ameliox [INCI: Carnosine, Tocopherol, *Silybum marianum* Fruit Extract] or PhytoCellTec *Malus Domestica* [INCI: *Malus domestica* Fruit Cell Culture] marketed by Mibelle Biochemistry, Bioxilift [INCI: *Pimpinella anisum* Extract] or SMS Anti-Wrinkle® [INCI: *Annona squamosa* Seed Extract] marketed by Silab, antagonists of the $Ca^{2+}$ channel for example and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes for example and not restricted to, photolyase or T4 endonuclease V, or chloride channel agonists among others, and/or mixtures thereof.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and, in addition, a cosmetically or pharmaceutically effective amount of at least one extract which is a whitening or depigmenting agent or a melanin synthesis inhibiting agent, for example and not restricted to, *Achillea millefolium, Aloe vera, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus, Rumex occidentalis, Sapindus mukurossi, Saxifragia sarmentosa, Scutellaria galericulate, Sedum sarmentosum bunge, Stellaria medica, Triticum Vulgare, Arctostaphylos Uva ursi* or *Whitania somnifera* among others and/or in addition to a cosmetic or pharmaceutical effective quantity of at least one synthetic compound, extract or product of biotechnological origin with depigmenting or whitening activity or which inhibits melanin synthesis, for example and not restricted to Lipochroman-6 [INCI: Dimethylmethoxy Chromanol], Chromabright® [INCI: Dimethylmethoxy Chromanyl Palmitate] marketed by Lipotec, Whitami [INCI: Maltodextrin, Papain, Titanium Dioxide, Angelica Acutiloba Root Extract, Saposhnikovia Divaricata Root Extract, Thioctic Acid, Kaolin, Ascorbyl Glucoside, Pinus Pinaster Bark Oligomeric Proanthocyanidins] marketed by Alban Muller; NAB® Asafetida Extract [INCI: Aqua (Water), Butylene Glycol, Ethoxydiglycol, Ferula Foetida Extract] marketed by Arch; Licorice Roots Extract [INCI: Licorice (*Glycyrrhiza Glabra*) Extract] marketed by Campo Research; Belides™ [INCI: Bellis Perennis (Daisy) Flower Extract] marketed by CLR; Algowhite [INCI: *Ascophyllum Nodosum* Extract] marketed by Codif; Biowhite™ [INCI: Saxifraga Sarmentosa Extract, *Vitis Vinifera* (Grape) Fruit Extract, Butylene Glycol, Water, *Morus bombycis* Root Extract, Scutellaria *Baicalensis* Root Extract, Disodium EDTA], Melarrest A [INCI: Glycerin, Lactic Acid, Kojic Acid, Ascorbic Acid], Melarrest® L [INCI: Water, Cyclopentasiloxane, Butylene Glycol, Propylene Glycol, Phospholipids, *Glycyrrhiza Glabra* (Licorice) Extract, Kojic Acid, Ammonium Glycyrrhizate] Vitagen [INCI: Aminopropyl Ascorbyl Phosphate] marketed by Coletica/Engelhard/BASF; DC Skin Bright™ [INCI: PEG-12 Glyceryl Distearate, Methyl Dihydroxybenzoate, Ethoxydiglycol, Polyethylene, Water] marketed by DC Ingredients; DS-WHITEKLE [INCI: Acetylphytosphingosine] marketed by Doosan; TEGO Cosmo C 250 [INCI: 1-methylhydantoine-2-imide] marketed by Evonik Goldschmidt; Albatin® [INCI: Aminoethylphosphinic Acid, Butylene Glycol, Water] marketed by Exsymol; Synerlight™ [INCI: Actinidia Chinensis (Kiwi) Fruit Water, Butylene Glycol, Alcohol, Sophora Angustifolia Root Extract] marketed by Gattefossé; Clerilys™ [INCI: Water, Cucumis Santivus, *Morus Alba* Extract, *Hibiscus Sabdariffa* Extract, Wine Extract] marketed by Greentech; Melanostatine®-5 [INCI: Dextran, Nonapeptide-1] marketed by IEB/Unipex; Actiwhite™ [INCI: Water, Glycerin, Sucrose Dilaurate, Polysorbate 20, Pisum Sativum Extract], Active® Powder Whiteness [INCI: Water, Lauryl Methacrylate/Glycol Dimethacrylate Copolymer, Butylene Glycol, Dicaprylyl Ether, Titanium Dioxide, Algae, Citric Acid, Sodium Citrate, Waltheria Indica Leaf Extract, Ferulic Acid, Polyglyceryl-2-Dipolyhydroxystearate], Dermawhite® NF LS 9410 [INCI: Mannitol, Sodium Gluconate, Citric Acid, Sodium Citrate, Waltheria Indica Leaf Extract, Dextrin, Ferulic Acid], Radianskin™ [INCI: Hydroxyphenoxy Propionic Acid] marketed by L. Serobiologiques/Cognis/BASF; Lipobrite® HCA-4 [INCI: PEG-4, Hydroxycinnamic Acid] marketed by Lipochemicals; Whitessence™ [INCI: Artocarpus Heterophyllus Seed Extract, Maltodextrin, Disodium Phosphate, Sodium Phosphate] marketed by Lucas Meyer; Emblica™ [INCI: *Phyllanthus Emblica* Fruit Extract] marketed by Merck; SulforaWhite [INCI: *Lepidium Sativum* Sprout Extract, Glycerin, Lecithin, Phenoxyethanol, Aqua] Delentigo™ [INCI: *Lepidium Sativum* Sprout Extract, Lecithin, Soy Isoflavones, Polysorbate 80, Alcohol, Glycerin, Phenoxyethanol, Water] marketed by Mibelle; Alpha-Arbutin [INCI: Alpha-arbutin], Gigawhite [INCI: Water, Glycerin, *Malva Sylvestris* (Mallow) Extract, *Mentha Piperita* Leaf Extract, *Primula Veris* Extract, *Alchemilla Vulgaris* Extract, *Veronica Officinalis* Extract, *Melissa Officinalis* Leaf Extract, *Achillea Millefolium* Extract], Melfade®-J [INCI: Water, *Arctostaphylos Uva-Ursi* Leaf Extract, Glycerin, Magnesium Ascorbyl Phosphate] marketed by Pentapharm/DSM; CellActive® White [INCI: Aqua, Alcohol denat., Niacinamide, Zinc PCA, *Chlorella Vulgaris/Lupinus Albus* Protein Ferment, *Nasturtium Officinale* Extract] Illumiscin® [INCI: Glycerin, Aqua (Water), *Olea Europaea* Leaf Extract, Ascorbyl Glucoside, Zinc PCA] marketed by Rahn; Arlatone™ Dioic DCA [INCI: Octadecenedioic Acid, BHT], Etioline™ [INCI: Glycerin, Butylene Glycol, *Arctostaphylos Uva Ursi* Leaf Extract, *Mitracarpus Scaber* Extract], Lumiskin™ [INCI: Caprylic/Capric Triglycerid, DiacetylBoldine], Melaclear™ 2 [INCI: Glycerin, Water, Dithiaoctanediol, Gluconic Acid, Sutilains, Beta-carotene], Lumisphere™ [INCI: Water (Aqua), Titanium Dioxide, Polysorbate 20, Cetyl Hydroxyethylcellulose, Polymethylmethacrylate, Trilaurin, Diacetyl boldine], O.D.A.White™ [INCI: Octadecenedioic Acid], Wonderlight™ [INCI: Humulus Lupulus (Hops) Strobile] marketed by Sederma/CRODA; Sepiwhite™ MSH [INCI: Undecylenoyl phenylalanine], Sepicalm™ VG [INCI:

Sodium palmitoyl proline, Nymphaea Alba Flower Extract] marketed by Seppic; Clariskin II [INCI: *Triticum Vulgare* Extract], Dermalight® [INCI: *Tropaeolum Majus* Extract], Whitonyl® [INCI: *Palmaria Palmata* Extract] marketed by Silab; Azeloglicina® [INCI: Potassium Azelaoyl Diglycinate] marketed by Sinerga; Whitesphere Premium [INCI: Sucrose Palmitate, Butylene Glycol, Glyceryl Linoleate, *Prunus Amygdalus Dulcis*, Almond Oil, Water (aqua), *Glycyrrhiza Glabra* (Licorice) Root Extract, Magnesium Ascorbyl Phosphate, *Undaria Pinnatifida* Extract], Axolight [INCI: *Triticum Aestivum* Extract] marketed by Soliance; SymWhite® [INCI: Phenylethyl Resorcinol], Extrapone™ Nutgrass GW [INCI: Cyperus Rotundus Root Extract] marketed by Symrise; Synovea® HR [INCI: Hexylresorcinol] marketed by Sytheon; β-White [INCI: Water, Butylene Glycol, Hydrogenated Lecithin, Sodium Oleate, Oligopeptide-68, Disodium EDTA] marketed by Unipex; Achromaxyl™ [INCI: Brassica Napus Extract] marketed by Vincience/ISP; arbutin and its isomers, kojic acid and its derivatives, vitamin C and its derivatives, for example and not restricted to, 6-O-palmitoylascorbic acid, dipalmitoylascorbic acid, magnesium salt from ascorbic-2-phosphate acid (MAP), sodium from ascorbic-2-phosphate acid (NAP), ascorbyl glucoside or ascorbyl tetraisopalmitate (VCIP) among others, retinol and its derivatives, including tretinoin and isotretinoin, idebenone, hydroxybenzoic acid and its derivatives, flavonoids, soy extract, extract of lemon, extract of orange, extract of ginkgo, extract of cucumber, extract of geranium, extract of bearberry, extract of carob, extract of cinnamon, extract of marjoram, extract of rosemary, extract of clove, soluble extract of licorice, extract of blackberry leaf, niacinamide, liquiritin, resorcinol and its derivatives, hydroquinone, α-tocopherol, γ-tocopherol, azelaic acid, resveratrol, mercury salts, linoleic salts, α-lipoic acid, dihydrolipoic acid, alpha hydroxyacids, beta hydroxyacids, ellagic acid, ferulic acid, cinnamic acid, oleanolic acid, aloesin and its derivatives and/or inhibitors of serine protease activity, for example and not restricted to, inhibitors of tryptase, trypsin or PAR-2 activity, among others An additional aspect of this invention refers to a cosmetic or pharmaceutical composition which comprises a cosmetic or pharmaceutically effective quantity of at least one peptide of the invention or its stereoisomers, mixtures thereof and/or its cosmetically or pharmaceutically acceptable salts, as well as a cosmetically or pharmaceutically quantity of at least one natural extract or essential oil which is anti-itching agent, for example and not restricted to, extracts of *Abelmoschus esculentus, Actaea alba, Aglaia odorata, Alkanna tinctoria, Althaea officinalis, Altingia excelsa, Andropogon virginicus, Aralia nudicaulis, Aralia racemosa, Argemone mexicana, Barleria prionitis, Camelia sinensis, Caesalpinia digyna, Campsis grandiflora, Carissa congesta, Carthamus oxyacantha, Cassia tora, Chrysanthemum indicum, Cimicifuga racemosa, Cinnamomum camphora, Clematis vitalba, Cuscuta reflexa, Diospyros peregrina, Enicostema axillare, Hammamelis virginiana, Jatropha multifida, Lavandula officinalis, Lavandula latifolia, Liquidambar orientalis, Lithospermum officinale, Madhuca longifolia, Martynia annua, Medicago sativa, Michelia champaca, Mikania glomerata, Mimosa pudica, Oryza sativa, Phaseolus vulgaris, Phyllanthus urinaria, Phyllanthus virgatus, Pistacia vera, Polygonum hydropiper, Quercus ilex, Rauvolfia caffra, Ricinus communis, Rubus idaeus, Sagittaria sagittifolia, Sandoricum koetjape, Sapindus mukorossi, Schleichera oleosa, Sesbania grandiflora, Spondias dulcis, Tilia* sp., *Toona ciliata, Tragia involucrata, Trichosanthes quinquangulata, Vaccaria pyramidata, Ventilago madraspatana, Veratrum album* or *Xanthium strumarium* among others or at least one synthetic compound or product of biotechnological origin which is an anti-itching agent, for example and not restricted to mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cyclizine, chlorcyclizine, hydroxyzine, meclizine, cetirizine, levocetirizine, promethazine, thenaldine, alimemazine (trimeprazine), cyproheptadine, azatidine, ketotifen, acrivastine, astemizole, cetirizine, loratadine, desloratadine, mizolastine, terfenadine, fexofenadine, fexofenadine, azelastine, levocabastine, olopatadine, corticosteroids such as cortisone, hydrocortisone dexamethasone, prednisone; Neutrazen™ [INCI: Water, Butylene Glycol, Dextran, Palmitoyl Tripeptide-8] marketed by Atrium Innovations/Unipex Group, Meliprene® [INCI: Dextran, Acetyl Heptapeptide-1] marketed by Institut Europeen de Biologie Cellulaire/Unipex Group, Skinasensyl™ [INCI: Acetyl Tetrapeptide-15] marketed by Laboratoires Serobiologiques/Cognis, SymSitive® 1609 [INCI: 4-t-Butylcyclohexanol] marketed by Symrise, Symbiocell™ [INCI: Extract from *Cestrum Latifolium*] marketed by BASF, Gatuline® Derma-Sensitive [INCI: Octyldodecyl Myristate, *Capparis Spinosa* Fruit Extract] marketed by Gattefossé or MAXnolia [INCI: Magnolia Officinalis Bark Extract, *Vitis Vinifera/Vitis Vinifera* (Grape) Seed Extract, Tocopherol] marketed by Mibelle among others.

An additional aspect of this invention relates to a cosmetic or pharmaceutical composition containing a cosmetically or pharmaceutically effective amount of at least one peptide of the invention, its stereoisomers, mixtures thereof and/or its cosmetically or pharmaceutically acceptable salts, and also a cosmetically or pharmaceutically effective amount of at least one natural extract or essential oil for the treatment of sensitive skin, for example and not restricted to, extracts of *Abelmoschus esculentus*, amaranth seed oil, oil from *Alkanna tinctoria* wood, *Aloe vera, Althaea officinalis, Altingia excelsa, Andropogon virginicus, Aralia nudicaulis, Aralia racemosa, Argemone mexicana, Arnica montana, Artemisia vulgaris, Asarum maximum, Barleria prionitis, Calendula officinalis, Camelia sinensis, Caesalpinia digyna, Campsis grandiflora, Capsicum* spp., *Carissa congesta, Carthamus oxyacantha, Cassia tora, Centipeda cunninghamii, Chamomilla recutita, Chrysanthemum indicum, Cimicifuga racemosa, Cinnamomum camphora, Clematis vitalba, Cuscuta reflexa, Crinum asiaticum, Diospyros peregrina, Enicostema axillare, Hamamelis virginiana, Harpagophytum procumbens, Hypericum perforatum, Jatropha multifida, Lavandula officinalis, Lavandula latifolia, Lilium candidum, Liquidambar orientalis, Lithospermum officinale, Madhuca longifolia, Malva sylvestris, Martynia annua, Melaleuca altemifolia, Medicago sativa, Michelia champaca, Mikania glomerata, Mimosa pudica, Origanum majorana, Origanum vulgare, Oryza sativa, Phaseolus vulgaris, Phyllanthus urinaria, Phyllanthus virgatus, Pistacia vera, Polygonum hydropiper, Prunus laurocerasus, Rosmarinus officinalis, Quercus ilex, Rauvolfia caffra, Ricinus communis, Rubus idaeus, Sagittaria sagittifolia, Salix alba, Sandoricum koetjape, Sapindus mukorossi, Schleichera oleosa, Sesbania grandiflora, Silybum marianum*, extracts of *Spondias dulcis, Tanacetum parthenium, Thymus vulgaris, Tilia* sp., *Toona ciliata, Tragia involucrata, Trichosanthes quinquangulata, Uncaria guianensis* or *Vaccaria pyramidata, Vaccinum myrtillus, Ventilago madraspatana, Veratrum album* or *Xanthium strumarium* among others; coenzyme Q10 or alkyl glycerol ethers, Abyssine® [INCI: Water, Alteromonas Ferment Extract, Butylene Glycol], Aldavine™ [INCI: Water, *Ascophyllum nodosum* extract, *Asparagopsis armata* extract, Sorbitol], Neutrazen™ [INCI: Water, Butylene Glycol, Dextran, Palmitoyl Tripeptide-8] or Melitane® [INCI: Dextran, Acetyl Hexapeptide-1] marketed by Atrium/Unipex; AquaCacteen® [INCI: Glycerin, *Opuntia Ficus Indica* Stem Extract, Phenoxyethanol, Aqua], Calmosensine™ [INCI: Butylene Glycol, Aqua, Laureth-3, Hydroxyethylcellulose, Acetyl Dipeptide-1 Cetyl Ester], Caresoft™ [INCI: Propanediol, Glycerin, Water, Curculigo Orchioides Root Extract], CM-Glucan [INCI: Sodium Carboxymethyl Betaglucan, Phenoxyethanol, Imidazolidinyl Urea, Water (Aqua)] or MAXnolia [INCI: *Magnolia Officinalis* Bark Extract, *Vitis Vinifera/Vitis Vinifera* (Grape) Seed Extract, Tocopherol] marketed by Mibelle; Bacocalmine™ [INCI: PEG-8, Bacopa Monniera Extract, Water (Aqua), Hydroxyethylcellulose] marketed by Sederma/CRODA; Defensil® [INCI: Octyl Dodecanol, *Echium Plantagineum* Seed Oil, *Cardiospermum Halicacabum* Extract, *Helianthus Annuus* Seed Oil Unsaponifiables] marketed by Rahn; DS-PHYTOSPHINGOSINE [INCI: Phytosphingosine], DS-TAPS [INCI: Tetraacetylphytosphingosine] or DS-WHITEKLE [INCI: Acetylphytosphingosine] marketed by Doosan; Elhibin® [INCI: *Glycine Soja* Protein, Water, Glycerin, Disodium cocoamphodiacetate] marketed by Pentapharm/DSM; Gatuline® Derma-Sensitive [INCI: Octyldodecyl Myristate, *Capparis Spinosa* Fruit Extract] marketed by Gattefossé; Glutrapeptide® [INCI: Aqua, Pyroglutamylamidoethyl Indole] or Glistin [INCI: Glutamylamidoethyl Indole, Water (Aqua)] marketed by Exsymol; Inhipase™ [INCI: *Pueraria Lobata* Root Extract, Butylene Glycol] or Symbiocell™ [INCI: *Cestrum Latifolium* Leaf Extract] marketed by BASF; Meliprene® [INCI: Dextran, Acetyl Heptapeptide-1] marketed by Institut Europeen de Biologie Cellulaire/Unipex Group; NAB® *Arnica* Extract [INCI: *Arnica Montana* Flower Extract, Algae Extract] marketed by Arch Chemicals; Ocaline [INCI: Sea water, Water, *Cucurbita pepo* (pumpkin) seed extract] marketed by Soliance; Phytosphingosine [INCI: Phytosphingosine] marketed by Evonik Goldschmidt; Protectol [INCI: Dipropylene glycol, *Betula alba* bark extract, *Scrophularia nodosa* extract] marketed by Greentech; Skinasensyl™ [INCI: Water, Glycerin, Coco-Glucoside, Acetyl Tetrapeptide-15] marketed by L. Serobiologiques/Cognis/BASF; SymSitive® 1609 [INCI: Pentylene Glycol, 4-t-Butylcyclohexanol] marketed by Symrise; Stimu-Tex® AS [INCI: Spent Grain Wax, *Butyrospermum Parkii* (Shea Butter) Extract, *Argania Spinosa* Kernel Oil] marketed by Pentapharm/DSM; Timecode™ [INCI: Palmitoyl Glycine] marketed by Seppic; Unisooth ST-32 [INCI: Water (Aqua), Pentylene Glycol, Tamarindus Indica Seed Extract, Stevioside] marketed by Induchem or Vital ET® [INCI: Disodium Lauriminodipropionate Tocopheryl Phosphates] marketed by ISP, among others.

Likewise, in another particular embodiment, the agent stimulating healing, the coadjuvant healing agent, the agent stimulating reepithelization and/or the coadjuvant healing agent is selected, for example and not restricted to, from the group formed by extracts of *Aristoloquia clematis, Centella asiatica, Rosa moschata, Echinacea angustifolia, Symphytum officinale, Equisetum arvense, Hypericum perforatum, Mimosa tenuiflora, Persea graffsima, Prunus africanum, Tormentilla erectea, Aloe vera*, Polyplant® Epithelizing [INCI: *Calendula Officinalis, Hypericum Perforatum, Chamomilla Recutita, Rosmarinus Officinalis*] marketed by Provital, Cytokinol® LS 9028 [INCI: Hydrolyzed Casein, Hydrolyzed Yeast Protein, Lysine HCl] marketed by Laboratories Serobiologiques/Cognis or Deliner® [INCI: *Zea May* (Corn) Kernel Extract] marketed by Coletica/Engelhard/BASF, allantoin, cadherins, integrins, selectins, hyaluronic acid receptors, immunoglobulins, fibroblast growth factors, connective tissue growth factors, platelet-derived growth factors, vascular endothelial growth factors, epidermal growth factors, insulin-like growth factors, keratinocyte growth factor, colony-stimulating factor, transforming growth factor beta, tumor necrosis factor-alpha, interferons, interleukins, matrix metalloproteinases, receptor protein tyrosine phosphatases, Antarcticine® [INCI: *Pseudoalteromonas* Ferment Extract], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Bodyfensine™ [INCI: Acetyl Dipeptide-3 Aminohexanoate] or Diffuporine™ [INCI: Acetyl Hexapeptide-37] marketed by Lipotec, among others.

In another particular embodiment, the anti-inflammatory agent and/or analgesic is selected, for example and not restricted to, from the group formed by extract of madecassoside, extract of echinacea, amaranth seed oil, sandalwood oil, extract of peach tree leaf, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officinalis, Salix alba, Silybum marianum, Tanacetum parthenium, Thymus vulgaris, Uncaria guianensis* or *Vaccinum myrtillus*, mometasone furoate, prednisolone, non-steroidal anti-inflammatories including cyclooxygenase or lipoxygenase inhibitors, benzydamine, acetylsalicylic acid, rosmarinic acid, ursolic acid, glycyrrhizinate derivatives, α-bisabolol, azulene and analogs, sericoside, ruscogenin, escin, escholine, rutin and analogs, hydrocortisone, clobetasol, dexamethasone, halobetasol, diflorasone, fluocinonide, amcinonide, triamcinolone, fluticasone, fluocinolone, flurandrenolide, prednicarbate, prednisone, paracetamol, amoxiprin, benorilate, choline salicylate, faislamine, methyl salicylate, magnesium salicylate, salsalate, diclofenac, aceclofenac, acemetacin, bromfenac, etodolac, indomethacin, oxamethacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone, omega-3 and omega-6 fatty acids, morphine, codeine, oxycodone, hydrocodone, diamorphine, pethidine, tramadol, buprenorphine, benzocaine, lidocaine, chloroprocaine, tetracaine, procaine, amitriptyline, carbamazepine, gabapentin, pregabalin, bisabolol, Neutrazen™ [INCI: Water, Butylene Glycol, Dextran, Palmitoyl Tripeptide-8] marketed by Atrium Innovations/Unipex Group, Meliprene® [INCI: Dextran, Acetyl Heptapeptide-1] marketed by Institut Europeen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Serobiologiques/Cognis, Calmosensine™ [INCI: Acetyl Dipeptide-1] marketed by Sederma, coenzyme Q10 or alkyl glycerol ethers.

Applications

An aspect of this invention relates to the use of at least one peptide of general formula (I), its stereoisomers, mixtures thereof and/or its cosmetically or pharmaceutically acceptable salts in the preparation of a cosmetic or pharmaceutical composition to inhibit PAR-2 activity.

In a particular embodiment, this invention relates to the use of at least one peptide of general formula (I), its stereoisomers, mixtures thereof and/or its cosmetically or pharmaceutically acceptable salts in the preparation of a cosmetic or pharmaceutical composition for treatment and/or prevention of itching, inflammation, pain, diseases and/or disorders of the respiratory airways.

In a preferable embodiment, the itching is selected from itching associated with conditions, diseases and/or disorders, for example and not restricted to, dermatitis, atopic dermatitis, contact dermatitis, diaper dermatitis, dermatitis herpetiformis, photodermatosis, photosensitivity, dermatosis related to pregnancy, dermatosis related to menopause, eczema, sensitive skin, psoriasis, chickenpox, herpes, herpes zoster, Netherton's syndrome, peeling skin syndrome, lichen planus, acne, dandruff, seborrhea, seborrheic dermatitis, alopecia, athlete's foot, candidiasis, hemorrhoids, vaginal itching, pruritus ani, anogenital pruritus, sunburn, urticaria, pruritic otitis, senile pruritus, aquagenic pruritus, prurigo nodularis, prurigo planus, pityriasis rosea, xerosis and dry skin, or pruritus associated with dialysis, HIV infection, malignant neoplasms, Hodgkin's disease, leukemia, myeloma, lymphoma, solid tumors, adenocarcinomas, lung cancer, hepatic diseases, jaundice, cholestasis, liver failure, cirrhosis, polycythemia, hypereosinophilic syndrome, primary thrombocythemia, myelodysplastic syndrome, anemia due to iron deficiency, systemic lupus erythematosus, endocrine diseases, thyroid diseases, hyperthyroidism, hypothyroidism, parathyroid diseases, diabetes mellitus, kidney diseases, kidney failure, uremia, parasitic diseases, scabies, lice, intestinal worms, allergic reactions, allergies to medication, food allergies, allergies to chemical products, exposure to poisonous plants, exposure to insect bites, chemotherapy, stress and anxiety, among others.

In another particular embodiment, the pain is selected, for example and not restricted to, from the group formed by acute pain, chronic pain, nociceptive pain, neuropathic pain, inflammatory pain, visceral pain, abdominal pain, digestive system pain, respiratory system pain, urogenital system pain, endocrine system pain, heart pain, pancreatic pain, hepatic pain, pain due to gallstones, cholestasis, intestinal pain, stomach pain, pain due to duodenal ulcers, pain due to esophagitis, pain due to gastroesophageal reflux disease, spleen pain, pain in the blood vessels, thalamic syndrome pain, irritable bowel syndrome, pain associated with Crohn's disease, pain associated with ulcerative colitis, diverticulitis, gastrointestinal mucositis, headaches, tension headaches, headache associated with sinusitis, migraines, eye pain, dry eye syndrome, postoperative pain, postoperative pain due to surgical incisions, postoperative pain due to implant insertions in the bone, postoperative pain due to bone substitutions, postoperative pain due to infections, postoperative pain due to limb amputations, pain due to bone fractures, pain due to cancer, pain due to bone cancer, pain associated with benign bone tumors, pain associated with osteoid osteomas, pain associated with osteoblastomas, pain due to cancer treatment, pain due to chemotherapy, pain due to emesis, pain due to emesis resulting from chemotherapy treatment, musculoskeletal pain, spastic muscle pain, fibromyalgia, complex regional pain syndrome, psychogenic pain, neuralgic pain, pain due to demyelinating diseases, neck pain associated with cervical dystonia, back pain, lumbago, sciatica, neurogenic inflammation, neuritis, causalgia, touch sensitivity, cold sensitivity, heat sensitivity, skin irritation, post-hair removal skin irritation, post-shaving skin irritation, psoriasis, sensitive skin, dermatitis, atopic dermatitis, contact dermatitis, diaper dermatitis, seborrheic dermatitis, eczema, lichen planus, burns, sunburn, arthritis, rheumatoid arthritis, osteoarthritis, psoriatic arthritis, uveitis, pain due to nerve damage, neuralgia, postherpetic neuralgia, neuropathies, peripheral neuropathies, phantom pains, allodynia, hyperalgesia, cold hyperalgesia, pain due to carpal tunnel syndrome, burning pain, Grierson-Gopalan syndrome (better known as burning feet syndrome), burning mouth syndrome, paresthesia, Fabry's disease, facial pain, trigeminal neuralgia, neuropathic pain due to diabetes, neuropathic pain due to AIDS, orofacial pain, dental pain, pain due to tooth removal, pain due to removal of a wisdom tooth, tooth sensitivity to the cold, tooth sensitivity to heat, oral mucositis, temporomandibular joint pain, joint pain caused by gout, pain associated with tattoo or tattoo removal processes, bunion pain, testicular pain, myofascial pain, urinary bladder pain, urinary tract pain, cystitis, pain due to kidney stones, renal colic, vulval pain, vaginal pain, post-birth pain, menstrual pain, scrotal pain, perineum pain, pelvic pain or hypersensitivity, skin pain or irritation after surgery, after treatment with intense pulsed light therapy (IPL), after treatment with monochromatic pulsed light therapy (laser), after treatment with chemical peeling agents or after overexposure to aggressive external agents and pain due to chronic alcohol abuse.

In another particular aspect, the inflammation is selected, for example and not restricted to, from the group formed by neurogenic inflammation, joint inflammation, tendon inflammation, muscular inflammation, sepsis, vascular inflammation, respiratory inflammation, chronic obstructive pulmonary disease, rhinitis, allergic rhinitis, asthma, otitis, intestinal inflammation, Crohn's disease, pancreatitis, hepatitis, conditions related to chronic inflammation, acute inflammation, nephritis, systemic lupus erythematosus, arthritis, rheumatoid arthritis, adult and juvenile rheumatoid arthritis, Still's disease, psoriatic arthritis, osteoarthritis, arthritis caused by gout, rheumatoid spondylitis, glomerulonephritis, neuritis, nerve tissue inflammation, multiple sclerosis, immune system disorders, Sjögren's syndrome, atherosclerosis, myocarditis, pericarditis, vasculitis, inflammatory skin conditions, psoriasis, sensitive skin, dermatitis, atopic dermatitis, contact dermatitis, diaper dermatitis, seborrheic dermatitis, eczema, hyperproliferative skin disease, burns, sunburn, inflammation of the vaginal mucus, vulvodynia, vaginitis, inflammation of the oral mucosa, gingivitis, periodontitis, inflammatory eye diseases, uveitis, ocular and vernal conjunctivitis, sarcoidosis, peptic ulcers, urticaria, bullous pemphigoid, scleroderma, fibrosis, angioedema, anaphylaxis, alopecia, cirrhosis of the liver, restenosis, rheumatic polymyalgia, seronegative spondyloarthropathy, including ankylosing spondylitis and Reiter's syndrome, dermatomyositis, inclusion body myositis, polymyositis and lymphangioleiomyomatosis.

In another particular embodiment the diseases and/or disorders of the respiratory airways are selected, for example and not restricted to, from the group formed by asthma, chronic obstructive pulmonary disease, allergic rhinitis and bronchial hyperactivity.

In another particular embodiment, this invention refers to the use of at least one peptide of general formula (I) its stereoisomers, mixtures thereof and/or its cosmetically or pharmaceutically acceptable salts in the preparation of a pharmaceutical composition for the treatment of cancer.

In a preferred embodiment, the cancer is selected, for example and not restricted to, from the group formed by lymphoreticular neoplasms, bone cancer, osteosarcoma, liposarcoma, breast cancer, stomach cancer, pancreatic cancer, bladder cancer, bowel cancer, endometrial cancer, cancer of the uterus, head and neck cancer, lung cancer, cancer of the respiratory airways, melanoma, ovarian cancer, prostate cancer, skin cancer and rectal cancer, among others.

In another particular embodiment, this invention refers to the use of at least one peptide of general formula (I) its stereoisomers, mixtures thereof and/or its cosmetically or pharmaceutically acceptable salts in the preparation of a pharmaceutical composition for the treatment and/or care of conditions, disorders and/or diseases of the digestive system.

In a preferred embodiment, the conditions, disorders and/or diseases of the digestive system are selected, for example and not restricted to, from the group formed by celiac disease, food allergies, Crohn's disease, gastroenteritis, inflammatory intestinal disease, intestinal colic, hepatitis, colitis, ulcerative colitis, irritable bowel syndrome, esophagitis, gastroesophageal reflux disease, idiopathic gastroparesis, pancreatitis including chronic pancreatitis, and gastric and duodenal ulcers.

Another aspect of this invention refers to the use of at least one peptide of general formula (I) its stereoisomers, mixtures thereof and/or its cosmetically or pharmaceutically acceptable salts in the preparation of a cosmetic or pharmaceutical composition for the treatment and/or care of the skin and/or mucous membranes.

In another preferred embodiment, this invention refers to the use of at least one peptide of general formula (I) its stereoisomers, mixtures thereof and/or its cosmetically or pharmaceutically acceptable salts in the preparation of a cosmetic or pharmaceutical composition that stimulates and/or cares for the skin barrier function.

In another particular embodiment, this invention refers to the use of at least one peptide of general formula (I) its stereoisomers, mixtures thereof and/or its cosmetically or pharmaceutically acceptable salts in the preparation of a cosmetic or pharmaceutical composition to heal and/or reepithelize the skin.

In another particular embodiment, this invention refers to the use of at least one peptide of general formula (I) its stereoisomers, mixtures thereof and/or its cosmetically or pharmaceutically acceptable salts in the preparation of a cosmetic or pharmaceutical composition to depigment and/or photoprotect the skin or for the treatment and/or care of those conditions, disorders and/or diseases of the skin which improve or are prevented by the reduction in the pigmentation of the skin or by the photoprotection of the skin.

In a preferred embodiment, the conditions, disorders and/or diseases of the skin which improve or are prevented by the reduction of the pigmentation of the skin or by photoprotection of the skin are selected, for example and not restricted to, from the group formed by freckles, lentigo, melasma, piebaldism, Addison's disease, vitiligo, marks due to exposure to UV radiation, marks due to aging or photoaging, marks caused by inflammation, and in particular inflammation due to laser or IPL treatment or post-aesthetics surgery, marks from acne, eczema, ochronosis, marks due to scars and/or hormonal disturbances such as chloasmas and melasmas.

In another particular embodiment, this invention refers to the use of at least one peptide of general formula (I) its stereoisomers, mixtures thereof and/or its cosmetically or pharmaceutically acceptable salts in the preparation of a cosmetic or pharmaceutical composition for the treatment of the scalp and/or capillary hygiene, and in particular for its use in the treatment and/or care of alopecia, dandruff and/or seborrheic dermatitis.

In another particular embodiment, this invention refers to the use of at least one peptide of general formula (I) its stereoisomers, mixtures thereof and/or its cosmetically or pharmaceutically acceptable salts in the preparation of a cosmetic or pharmaceutical composition for the treatment of oral mucosa and/or oral hygiene, and in particular for its use in the treatment and/or care of periodontitis and/or gingivitis.

In another particular embodiment, this invention refers to the use of at least one peptide of general formula (I) its stereoisomers, mixtures thereof and/or its cosmetically or pharmaceutically acceptable salts in the preparation of a cosmetic or pharmaceutical composition for the treatment of vaginal mucosa and/or intimate hygiene, and in particular for its use in the treatment and/or care of candidiasis, vaginal itching, pruritus ani, anogenital pruritus, and/or hemorrhoids.

In another particular embodiment, this invention refers to the use of at least one peptide of general formula (I) its stereoisomers, mixtures thereof and/or its cosmetically or pharmaceutically acceptable salts in the preparation of a cosmetic or pharmaceutical composition for the inhibition of skin sensitizing agents, and particularly allergens in cosmetic compositions.

In another aspect, this invention refers to a method for the inhibition of PAR-2 activity, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method for the treatment and/or prevention of itching, inflammation, pain, diseases and/or disorders of the respiratory airways, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method for the treatment of cancer, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method for the treatment and/or care of those conditions, disorders and/or diseases of the digestive system, which comprises the administration of a cosmetically or pharmaceutically effective amount of at least one peptide of general formula (I) its stereoisomers, mixtures thereof and/or its cosmetically or pharmaceutically acceptable salts.

Alternatively, the invention refers to a method for the treatment and/or care of the skin and/or mucous membranes, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method to stimulate and/or care for the skin barrier function, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method to heal and/or reepithelize the skin, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method to depigment and/or photoprotect the skin or to treat and/or care for those conditions, disorders and/or diseases of the skin which improve or are prevented by the reduction in the pigmentation of the skin or by the photoprotection of the skin, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method for the treatment of the scalp or for capillary hygiene, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method for the treatment of oral mucosa or for oral hygiene, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method for the treatment of vaginal mucosa or for intimate hygiene, which comprises the administration of a cosmetically or pharmaceutically effective amount of at least one peptide of general formula (I) its stereoisomers, mixtures thereof and/or its cosmetically or pharmaceutically acceptable salts.

In another particular aspect, this invention refers to a method for the inhibition of skin sensitizing agents, which comprises the administration of a cosmetically or pharmaceutically effective amount of at least one peptide of general formula (I) its stereoisomers, mixtures thereof and/or its cosmetically or pharmaceutically acceptable salts.

The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day.

The following specific examples provided here illustrate the nature of this invention. These examples are included for illustrative purposes only and should not be construed as limitations on the invention claimed herein.

EXAMPLES

The following examples serve to illustrate the invention and should not be construed as limitations to its scope.

ABBREVIATIONS

The abbreviations used for amino acids follow the 1983 IUPAC-IUB Commission on Biochemical Nomenclature recommendations outlined in *Eur. J. Biochem.*, (1984), 138, 9-37.

®, resin; 2,6-diClZ, 2,6-dichlorobenzyl; 2-BrZ, bromobenzyloxycarbonyl; 2-ClTrt®, 2-chlorotrityl resin; Ac, acetyl; Adpoc, 1-(1-adamantyl)-1-methylethoxy-carbonyl; AIDS: acquired immune deficiency syndrome; Ala, alanine; All, allyl; Alloc, allyloxycarbonyl; AM, 2-[4-aminomethyl-(2,4-dimethoxyphenyl)] phenoxyacetic acid; Arg, arginine; Asn, asparagine; Asp, aspartic acid; Boc, tert-butyloxycarbonyl; Bom, benzyloxymethyl; Brz, bromobenzyloxycarbonyl; Bzl, benzyl; Cbz, carboxybenzyl; CGRP, calcitonin gene-related peptide; CAMP, cyclic adenosine monophosphate, AMP cyclic adenosine phosphate; cHx, cyclohexyl; Cit, citrulline; ClZ, 2-chlorobenzyl; CFA, Complete Freund's Adjuvant; C-terminal, carboxy-terminal; DCM, dichloromethane, methylene chloride; Dde, N-[1-(4,4-dimethyl-2,6-dioxocyclohex-1-ylidene)ethyl; DIEA, N,N'-diisopropylethylamine; DIPCDI, N,N'-diisopropylcarbodiimide; Dmab, 4-(N-[1-(4,4-dimethyl-2,6-dioxocyclohexylidene)-3-methylbutyl] amino)benzyl; DMEM, Dulbecco modified Eagle's medium; DMF, N,N-dimethylformamide; DNA, deoxyribonucleic acid; Dnp, 2,4-dinitrophenol; DRG, dorsal root ganglion; EAE, experimental autoimmune encephalomyelitis; EDTA, ethylenediaminetetraacetic acid; ELISA, enzyme-linked immunosorbent assay; equiv: equivalent; ESI-MS, electrospray ionization mass spectrometry; FBS, fetal bovine serum; Fm, fluorenylmethyl; Fmoc, 9-fluorenylmethyloxycarbonyl; For, formyl; FVIIa, coagulation factor VIIa; Fxa, coagulation factor Xa; Gln, glutamine; HBSS, Hank's balanced salt solution; HDFa, human dermal fibroblasts, adult; His, histidine; HOAt, 1-hydroxy-7-azabenzotriazole; HOBt, 1-hydroxybenzotriazole; HPLC, high performance liquid chromatography; IBD, irritable bowel syndrome; IL-6, interleukin-6; IL-8, interleukin-8; Ile, isoleucine; INCI, International Nomenclature of Cosmetic Ingredients; IPL, Intense Pulsed Light; ivDde, 1-(4,4-dimethyl-2,6-dioxocyclohexylidene)-3-methyl-butyl; LDMA-25, laurdimonium hydrolyzed protein; Lys, lysine; MAP, magnesium ascorbyl-2phosphate acid; MBHA, p-methylbenzhydrylamine; Me, methyl; MeCN, acetonitrile; MeOH, methanol; Met, methionine; mRNA, messenger ribonucleic acid; Mtr, 4-methoxy-2,3,6-trimethylbenzenesulfonyl; Mts, mesitylenesulfonyl; Mtt, methoxytrityl or methyltrityl; Nle, norleucine; N-terminal, amino-terminal; Nva, norvaline; Orn, ornithine; PAL, 5-(4-aminomethyl-3,5-dimethoxyphenoxy) valeric acid; Palm, palmitoyl; PAR, protease-activated receptor; Pbf, 2,2,4,6,7-pentamethyldihydrobenzofuran-5-sulfonyl; PBS, phosphate buffered saline; PEG, polyethylene glycol; Phe, phenylalanine; Phg, phenylglycine; PGC-1α, PPARγ 1α co-activator; Pmc, 2,2,5,7,8-pentamethylchroman-6-sulfonyl; PPAR, peroxisome proliferator-activated receptor γ; pNZ, p-nitrobenzyloxycarbonyl; q.s., quantity sufficient; q.s.p., quantity sufficient for; RHE, Reconstructed human epidermis; RNA, ribonucleic acid; SCCE, stratum corneum chymotryptic enzyme; SCTE, stratum corneum tryptic enzyme; Ser, serine; SP, substance P; tBu, tert-butyl; TAPS, Tetraacetyl Phytosphingosine; Teoc, 2-(trimethylsilyl)ethyloxycarbonyl; TF, tissue factor; TFA, trifluoroacetic acid; THF, tetrahydrofuran; Thr, threonine; TIS, triisopropylsilane; Tos, tosyl or p-toluenesulfonyl; TRK, tropomyosin receptor kinase; Troc, 2,2,2 trichloroethoxycarbonyl; TRP, transient receptor potential; Trp, tryptophan; TRPV-1, transient receptor potential vanilloid subfamily 1; Trt, triphenylmethyl or trityl; Tyr, tyrosine; IUPAC, International Union of Pure and Applied Chemistry; IUB, International Union of Biochemistry; ULV, unilaminar vesicles; UVA, ultraviolet radiation A; UVB, ultraviolet radiation B; Val, valine; VCIP, ascorbyl tetraisopalmitate; Xan, xanthyl; Z, benzyloxycarbonyl.

Chemical Synthesis

All synthetic processes were carried out in polypropylene syringes fitted with porous polyethylene discs. All the reagents and solvents were synthesis quality and were used without any additional treatment. The solvents and soluble reagents were removed by suction. The Fmoc group was removed with piperidine-DMF (2:8, v/v) (1×1 min, 1×5 min, 5 mL/g resin) [Lloyd-Williams P. et al., "*Chemical Approaches to the Synthesis of Peptides and Proteins*", (1997), CRC, Boca Raton (FL, USA)]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser E. et al., "*Color test for detection of free terminal amino groups in the solid-phase synthesis of peptides*", (1970), Anal. Biochem., 34(2), 595-598] or chloranil test [Christensen T, "*A Qualitative Test for Monitoring Coupling Completeness in Solid Phase Peptide Synthesis Using Chloranil*", (1979), Acta Chem. Scand., 33B, 763-766]. All synthetic reactions and washes were carried out at 25° C.

The HPLC chromatographic analysis was carried out with Shimadzu equipment (Kyoto, Japan) using a reversed-phase column thermostatized at 30° C. (250×4.0 mm, Kromasil $C_8$, 5 µm, Akzo Nobel, Sweden). The elution was carried out using a gradient of acetonitrile (+0.07% TFA) in water (+0.1% TFA) at a flow rate of 1 mL/min and detection was carried out at 220 nm. The electrospray ionization mass spectrometry analysis was carried out in a WATERS Alliance ZQ 2000 detector using a mixture of $MeCN:H_2O$ 4:1 (+0.1% TFA) as the mobile phase and a flow rate of 0.2 mL/min.

Example 1

Obtaining Fmoc-$W_n$-$X_m$-$AA_1$-$AA_2$-$AA_3$-$AA_4$-$AA_5$-$AA_6$-$Y_p$-$Z_q$-O-2-ClTrt-®, wherein $AA_1$ is -L-Phe-, -L-Ser-, -L-Trp- or -L-Phg-; $AA_2$ is -L-Met-, -L-Phe-, -L-Nle-, -L-Trp-, -L-Phg- or -L-Nva-; $AA_3$ is -L-Arg-, -L-Gln-, -L-Trp-, -L-Lys-, -L-Orn-, -L-His-, -L-Cit-, -L-Asn- or -L-Phg-; $AA_4$ is -L-Asp-, -L-Phe-, -L-Asn-, -L-Gln-, -L-Tyr-, -L-Trp- or -L-Phg-; $AA_5$ is -L-His-, -L-Orn-, -L-Cit-, -L-Nle- or -L-Nva-; $AA_6$ is -L-Ser-, -L-Val-, -L-Thr, -L-Nle-, -L-Ile-, -L-Ala- or -L-Nva-; and n, m, p and q are 0

8.8 mmol (1 equiv) Fmoc-L-Ser(tBu)-OH, Fmoc-L-Val-OH, Fmoc-L-Thr(tBu)-OH, Fmoc-L-Nle-OH, Fmoc-L-Ile-OH, Fmoc-L-Ala-OH or Fmoc-L-Nva-OH dissolved in 55 mL of DCM are incorporated to which 0.86 equiv of DIEA are added to the 2-chlorotrityl resin (5.5 g; 8.8 mmol) dry resin. They are stirred for 5 min, after which 1.66 equiv of DIEA are added. The mixture is left to react for 40 min. The remaining chloride groups are blocked by treatment with 4.4 mL of MeOH.

The N-terminal Fmoc group is deprotected as described in the general methods and 2.5 equiv of Fmoc-L-His(Trt)-OH, Fmoc-L-Ile-OH, Fmoc-L-Orn(Boc)-OH, Fmoc-L-Cit-OH, Fmoc-L-Nle-OH or Fmoc-L-Nva-OH are coupled onto the peptidyl resins in the presence of 2.5 equiv of DIPCDI and 2.5 equiv of HOBt using DMF as a solvent for 1 hour. The resins are then washed as described in the general methods and the deprotection treatment of the Fmoc group is repeated to couple the next amino acid. Following the protocols described, 2.5 equiv of Fmoc-L-Asp(OtBu)-OH, Fmoc-L-Phe-OH, Fmoc-L-Asn(Trt)-OH, Fmoc-L-Gln(Trt)-OH, Fmoc-L-Tyr(tBu)-OH, Fmoc-L-Trp(Boc)-OH or Fmoc-L-Phg-OH; 2.5 equiv of Fmoc-L-Arg(Pbf)-OH, Fmoc-L-Gln(Trt)-OH, Fmoc-L-Trp(Boc)-OH, Fmoc-L-Lys(Boc)-OH, Fmoc-L-Orn(Boc)-OH, Fmoc-L-His(Trt)-OH, Fmoc-L-Cit-OH, Fmoc-L-Asn(Trt)-OH or Fmoc-L-Phg-OH; 2.5 equiv of Fmoc-L-Met-OH, Fmoc-L-Phe-OH, Fmoc-L-Nle-OH, Fmoc-L-Trp(Boc)-OH, Fmoc-L-Phg-OH or Fmoc-L-Nva-OH and finally 2.5 equiv of Fmoc-L-Phe-OH, Fmoc-L-Ser(tBu)-OH, Fmoc-L-Trp(Boc)-OH or Fmoc-L-Phg-OH are sequentially coupled in the presence of 2.5 equiv of HOBt and 2.5 equiv of DIPCDI at each coupling.

After the synthesis, the peptidyl resins are washed with DCM (5×3 min) and dried by nitrogen stream.

Example 2

Obtaining Fmoc-$W_n$-$X_m$-$AA_1$-$AA_2$-$AA_3$-$AA_4$-$AA_5$-$AA_6$-$Y_p$-$Z_q$-AM-MBHA-®, wherein $AA_1$ is -L-Phe-, -L-Ser-, -L-Trp- or -L-Phg-; $AA_2$ is -L-Met-, -L-Phe-, -L-Nle-, -L-Trp-, -L-Phg- or -L-Nva-; $AA_3$ is -L-Arg-, -L-Gln-, -L-Trp-, -L-Lys-, -L-Orn-, -L-His-, -L-Cit-, -L-Asn- or -L-Phg-; $AA_4$ is -L-Asp-, -L-Phe-, -L-Asn-, -L-Gln-, -L-Tyr-, -L-Trp- or -L-Phg-; $AA_5$ is -L-His-, -L-Orn-, -L-Cit-, -L-Nle- or -L-Nva-; $AA_6$ is -L-Ser-, -L-Val-, -L-Thr, -L-Nle-, -L-Ala- or -L-Nva-; and n, m, p and q are 0

In the following, weights have been normalized. 5 mmol (1 equiv) of the Fmoc-AM-MBHA resin with a functionalization of 0.73 mmol/g were treated with piperidine-DMF according to the described general protocol in order to remove the Fmoc group. 2.5 equiv of Fmoc-L-Ser(tBu)-OH, Fmoc-L-Val-OH, Fmoc-L-Thr(tBu)-OH, Fmoc-L-Nle-OH, Fmoc-L-Ile-OH, Fmoc-L-Ala-OH or Fmoc-L-Nva-OH were incorporated onto the deprotected resin in the presence of 2.5 equiv of DIPCDI and 2.5 equiv of HOBt using DMF as a solvent for 1 hour.

The resins were then washed as described in the general methods and the deprotection treatment of the Fmoc group was repeated to couple the next amino acid. The Fmoc N-terminal group was deprotected as described in the general methods and the 2.5 equiv of Fmoc-L-His(Trt)-OH, Fmoc-L-Ile-OH, Fmoc-L-Orn(Boc)-OH, Fmoc-L-Cit-OH, Fmoc-L-Nle-OH or Fmoc-L-Nva-OH; 2.5 equiv of Fmoc-L-Asp(OtBu)-OH, Fmoc-L-Phe-OH, Fmoc-L-Asn(Trt)-OH, Fmoc-L-Gln(Trt)-OH, Fmoc-L-Tyr(tBu)-OH, Fmoc-L-Trp(Boc)-OH or Fmoc-L-Phg-OH; 2.5 equiv of Fmoc-L-Arg(Pbf)-OH, Fmoc-L-Gln(Trt)-OH, Fmoc-L-Trp(Boc)-OH, Fmoc-L-Lys(Boc)-OH, Fmoc-L-Orn(Boc)-OH, Fmoc-L-His(Trt)-OH, Fmoc-L-Cit-OH, Fmoc-L-Asn(Trt)-OH or Fmoc-L-Phg-OH; 2.5 equiv of Fmoc-L-Met-OH, Fmoc-L-Phe-OH, Fmoc-L-Nle-OH, Fmoc-L-Trp(Boc)-OH, Fmoc-L-Phg-OH or Fmoc-L-Nva-OH and finally 2.5 equiv of Fmoc-L-Phe-OH, Fmoc-L-Ser(tBu)-OH, Fmoc-L-Trp(Boc)-OH or Fmoc-L-Phg-OH were incorporated onto the peptidyl resins, in the presence of 2.5 equiv of HOBt and 2.5 equiv of DIPCDI at each coupling.

After the synthesis, the peptidyl resins were washed with DCM (5×3 min) and dried by nitrogen stream.

Example 3

General Process for Removal of Fmoc N-Terminal Protective Group

Weights have been normalized. The N-terminal Fmoc group of the peptidyl resins obtained in example 2 was deprotected as described in the general methods (20% piperidine in DMF, 1×5 min+1×20 min). The peptidyl resins were washed with DMF (5×1 min), DCM (4×1 min), diethyl ether (4×1 min) and dried under vacuum. The same process could have been applied to the N-terminal Fmoc group of peptidyl resins obtained in Example 1.

Example 4

Process for Introducing the $R_1$ Palmitoyl Group onto the Peptidyl Resins Obtained in Example 3

10 equiv of pre-dissolved palmytic acid in DMF (1 mL) are incorporated onto 1 mmol (1 equiv) of the peptidyl resins obtained in Example 3, in the presence of 10 equiv of HOBt and 10 equiv of DIPCDI. They are allowed to react for 15 hours, after which the resins are washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and are dried under vacuum.

Example 5

Process for Introducing the $R_1$ Acetyl Group onto the Peptidyl Resins Obtained in Example 3

Weights have been normalized. 1 mmol (1 equiv) of the peptidyl resins obtained in Example 3 was treated with 25 equiv of acetic anhydride in the presence of 25 equiv of DIEA using 5 mL of DMF as a solvent. They were left to react for 30 mins, after which the peptidyl resins were washed with DMF (5×1 min), DCM (4×1 min), diethyl ether (4×1 min) and were dried under vacuum.

Example 6

Cleavage Process from the Polymeric Support of the Peptidyl Resins Obtained in Examples 3, 4 and 5

Weights have been normalized. 200 mg of the dried peptidyl resins obtained in Examples 5 were treated with 5 mL of TFA:TIS:$H_2O$ (90:5:5) for 2 hours at room temperature under stirring. The filtrates were collected onto 50 mL cold diethyl ether, they were filtered through polypropylene syringes fitted with porous polyethylene discs and washed 5 times with 50 mL diethyl ether. The final precipitates were dried under vacuum. The same processes could have been applied to the peptidyl resins obtained in Examples 3 and 4.

HPLC analysis of the obtained peptides in gradients of MeCN (+0.0% TFA) in $H_2O$ (+0.1% TFA) showed a purity exceeding 80% in all cases. The identity of the peptides obtained was confirmed by ESI-MS.

Example 7

Cleavage process of the polymeric support and functionalization with $R_2$ substituted amine: Obtaining Ac-$W_n$-$X_m$-$AA_1$-$AA_2$-$AA_3$-$AA_4$-$AA_5$-$AA_6$-$Y_p$-$Z_q$-NH—$(CH_2)_{15}$—$CH_3$, wherein $AA_1$ is -L-Phe-, -L-Ser-, -L-Trp- or -L-Phg-; $AA_2$ is -L-Met-, -L-Phe-, -L-Nle-, -L-Trp-, -L-Phg- or -L-Nva-; $AA_3$ is -L-Arg-, -L-Gln-, -L-Trp-, -L-Lys-, -L-Orn-, -L-His-, -L-Cit-, -L-Asn- or -L-Phg-; $AA_4$ is -L-Asp-, -L-Phe-, -L-Gln-, -L-Tyr-, -L-Trp- or -L-Phg-; $AA_5$ is -L-His-, -L-Orn-, -L-Cit-, -L-Nle- or -L-Nva-; $AA_6$ is -L-Ser-, -L-Val-, -L-Thr-, -L-Nle-, -L-Ile-, -L-Ala- or -L-Nva-; and n, m, p and q are 0

The peptides Ac-$W_n$-$X_m$-$AA_1$-$AA_2$-$AA_3$-$AA_4$-$AA_5$-$AA_6$-$Y_p$-$Z_q$-OH with fully protected side chains are obtained by treating 150 mg of the peptidyl resins Ac-$W_n$-$X_m$-$AA_1$-$AA_2$-$AA_3$-$AA_4$-$AA_5$-$AA_6$-$Y_p$-$Z_q$-O-2-ClTrt-® of Example 5, previously dried under vacuum in the presence of KOH, with 3 mL of a 3% solution of TFA in DCM for 5 min. The filtrates are collected onto 50 mL of cold diethyl ether and the treatment is repeated three times. The ethereal solutions are evaporated to dryness at reduced pressure and room temperature, the precipitates are redissolved in 50% MeCN in $H_2O$ and lyophilized. 10 mg of the obtained crude peptides are weighed in a flask and 3 equiv of hexadecylamine and 25 mL of anhydrous DMF are added. 2 equiv of DIPCDI are added, and left to react being magnetically stirred at 47° C. The reactions are monitored by HPLC until disappearance of the initial products, which are complete after 24-48 hours. The solvents are evaporated to dryness and co-evaporated twice with DCM. The obtained residues [Ac-$W_n$-$X_m$-$AA_1$-$AA_2$-$AA_3$-$AA_4$-$AA_5$-$AA_6$-$Y_p$-$Z_q$-NH—$(CH_2)_{15}$—$CH_3$ with fully protected side chains] are redissolved in 25 mL of a mixture of TFA-DCM-anisole (49:49:2) and left to react for 30 min at room temperature. 250 mL of cold diethyl ether are added, the solvents are evaporated under reduced pressure and two additional co-evaporations with ether are carried out. The residues are dissolved in a mixture of 50% MeCN in $H_2O$ and lyophilized.

HPLC analysis of the obtained peptides in gradients of MeCN (+0.07% TFA) in $H_2O$ (+0.1% TFA) show a purity exceeding 60% in all cases. The identity of the peptides obtained is confirmed by ESI-MS.

Example 8

Inhibition of PAR-2 Activity by the Peptides of the Invention

Human keratinocytes were seeded in 96-well plates at a density of 10,000 cells per well in 100 µL of complete DMEM culture medium. After 48 hours, the medium was removed and the cells were incubated with 100 µL of a solution of the peptides of the invention at 1 mg/mL for 1 hour at 37° C. in a $CO_2$ incubator. After the incubation, 100 µL of a mixture from the Fluo-4 NW (Invitrogen) fluorescent calcium probe and Probenecid was added to each well, prepared according to the supplier's instructions (Invitrogen), and the plate was incubated for 30 min at 37° C. in a $CO_2$ incubator, after which PAR-2 was activated by treatment with 1 µg/mL of the PAR-2 agonist I (Calbiochem).

The PAR-2 activity was determined by reading the fluorescence in a FLUOstar Galaxy reader (BMG LabTechnologies) using the 500 nm filters for the excitation and 520 nm for the emission, recording the fluorescence before and after PAR-2 activation. The fluorescence measurements were corrected with regard to the corresponding background fluorescences for each measurement and were standardized with regard to the maximum fluorescence observed in the treatment with the PAR-2 agonist I. The inhibition values of PAR-2 activity were calculated by comparing the maximum fluorescence corresponding to PAR-2 activation with agonist I and the values for each treatment. Table 3 details the best inhibition values of PAR-2 activity obtained for the peptides of the invention.

TABLE 3

| Treatment | PAR-2 activity | Inhibition PAR-2 activity |
|---|---|---|
| control | 0.0 | — |
| PAR-2 agonist I | 100.0 | 0 |
| 1 mg/mL Ac-L-Phe-L-Met-L-Arg-L-Asp-L-His-L-Ser-NH$_2$ (Ac-SEQ ID NO: 2)-NH$_2$) | 33.1 | 66.9 |
| 1 mg/mL Ac-L-Phe-L-Met-L-Gln-L-Phe-L-His-L-Ser-NH$_2$ (Ac-SEQ ID NO: 3)-NH$_2$) | 77.0 | 23.0 |
| 1 mg/mL Ac-L-Phe-L-Phe-L-Gln-L-Phe-L-His-L-Ser-NH$_2$ (Ac-SEQ ID NO: 4)-NH$_2$) | 62.6 | 37.4 |
| 1 mg/mL Ac-L-Ser-L-Phe-L-Gln-L-Phe-L-His-L-Ser-NH$_2$ (Ac-SEQ ID NO: 5)-NH$_2$) | 90.1 | 9.9 |
| 1 mg/mL Ac-L-Phe-L-Met-L-Trp-L-Phe-L-His-L-Ser-NH$_2$ (Ac-SEQ ID NO: 6)-NH$_2$) | 27.8 | 72.2 |
| 1 mg/mL Ac-L-Ser-L-Met-L-Trp-L-Phe-L-His-L-Ser-NH$_2$ (Ac-SEQ ID NO: 7)-NH$_2$) | 35.1 | 64.9 |
| 1 mg/mL Ac-L-Phe-L-Phe-L-Trp-L-Phe-L-His-L-Ser-NH$_2$ (Ac-SEQ ID NO: 8)-NH$_2$) | 50.8 | 49.2 |
| 1 mg/mL Ac-L-Ser-L-Phe-L-Trp-L-Phe-L-His-L-Ser-NH$_2$ (Ac-SEQ ID NO: 9)-NH$_2$) | 73.6 | 26.4 |
| 1 mg/mL Ac-L-Phe-L-Phe-L-Gln-L-Asp-L-Ile-L-Ser-NH$_2$ (Ac-SEQ ID NO: 10)-NH$_2$) | 73.0 | 27.0 |
| 1 mg/mL Ac-L-Phe-L-Met-L-Trp-L-Asp-L-Ile-L-Ser-NH$_2$ (Ac-SEQ ID NO: 11)-NH$_2$) | 73.5 | 26.5 |
| 1 mg/mL Ac-L-Phe-L-Phe-L-Trp-L-Asp-L-Ile-L-Ser-NH$_2$ (Ac-SEQ ID NO: 12)-NH$_2$) | 61.6 | 38.4 |
| 1 mg/mL Ac-L-Phe-L-Met-L-Arg-L-Phe-L-Ile-L-Ser-NH$_2$ (Ac-SEQ ID NO: 13)-NH$_2$) | 64.9 | 35.1 |
| 1 mg/mL Ac-L-Ser-L-Phe-L-Arg-L-Phe-L-Ile-L-Ser-NH$_2$ (Ac-SEQ ID NO: 14)-NH$_2$) | 83.8 | 16.2 |
| 1 mg/mL Ac-L-Phe-L-Met-L-Gln-L-Phe-L-Ile-L-Ser-NH$_2$ (Ac-SEQ ID NO: 15)-NH$_2$) | 10.9 | 89.1 |
| 1 mg/mL Ac-L-Ser-L-Met-L-Gln-L-Phe-L-Ile-L-Ser-NH$_2$ (Ac-SEQ ID NO: 16)-NH$_2$) | 47.4 | 52.6 |
| 1 mg/mL Ac-L-Phe-L-Phe-L-Gln-L-Phe-L-Ile-L-Ser-NH$_2$ (Ac-SEQ ID NO: 17)-NH$_2$) | 40.7 | 59.3 |
| 1 mg/mL Ac-L-Ser-L-Phe-L-Gln-L-Phe-L-Ile-L-Ser-NH$_2$ (Ac-SEQ ID NO: 18)-NH$_2$) | 61.0 | 39.0 |
| 1 mg/mL Ac-L-Phe-L-Met-L-Trp-L-Phe-L-Ile-L-Ser-NH$_2$ (Ac-SEQ ID NO: 19)-NH$_2$) | 32.3 | 67.7 |
| 1 mg/mL Ac-L-Ser-L-Met-L-Trp-L-Phe-L-Ile-L-Ser-NH$_2$ (Ac-SEQ ID NO: 20)-NH$_2$) | 32.2 | 67.8 |
| 1 mg/mL Ac-L-Phe-L-Phe-L-Trp-L-Phe-L-Ile-L-Ser-NH$_2$ (Ac-SEQ ID NO: 21)-NH$_2$) | 33.7 | 66.3 |
| 1 mg/mL Ac-L-Ser-L-Phe-L-Trp-L-Phe-L-Ile-L-Ser-NH$_2$ (Ac-SEQ ID NO: 22)-NH$_2$) | 60.8 | 39.2 |
| 1 mg/mL Ac-L-Phe-L-Phe-L-Arg-L-Asp-L-His-L-Val-NH$_2$ (Ac-SEQ ID NO: 23)-NH$_2$) | 39.7 | 60.3 |
| 1 mg/mL Ac-L-Phe-L-Phe-L-Trp-L-Asp-L-His-L-Val-NH$_2$ (Ac-SEQ ID NO: 24)-NH$_2$) | 85.2 | 14.8 |
| 1 mg/mL Ac-L-Phe-L-Met-L-Arg-L-Phe-L-His-L-Val-NH$_2$ (Ac-SEQ ID NO: 25)-NH$_2$) | 60.0 | 40.0 |
| 1 mg/mL Ac-L-Phe-L-Phe-L-Arg-L-Phe-L-His-L-Val-NH$_2$ (Ac-SEQ ID NO: 26)-NH$_2$) | 76.6 | 23.4 |
| 1 mg/mL Ac-L-Phe-L-Met-L-Gln-L-Phe-L-His-L-Val-NH$_2$ (Ac-SEQ ID NO: 27)-NH$_2$) | 77.5 | 22.6 |
| 1 mg/mL Ac-L-Ser-L-Met-L-Gln-L-Phe-L-His-L-Val-NH$_2$ (Ac-SEQ ID NO: 28)-NH$_2$) | 84.9 | 15.1 |
| 1 mg/mL Ac-L-Phe-L-Phe-L-Gln-L-Phe-L-His-L-Val-NH$_2$ (Ac-SEQ ID NO: 29)-NH$_2$) | 80.1 | 19.9 |
| 1 mg/mL Ac-L-Phe-L-Met-L-Trp-L-Phe-L-His-L-Val-NH$_2$ (Ac-SEQ ID NO: 30)-NH$_2$) | 23.5 | 76.5 |
| 1 mg/mL Ac-L-Ser-L-Met-L-Trp-L-Phe-L-His-L-Val-NH$_2$ (Ac-SEQ ID NO: 31)-NH$_2$) | 86.5 | 13.5 |
| 1 mg/mL Ac-L-Phe-L-Phe-L-Trp-L-Phe-L-His-L-Val-NH$_2$ (Ac-SEQ ID NO: 32)-NH$_2$) | 32.2 | 67.8 |
| 1 mg/mL Ac-L-Ser-L-Phe-L-Trp-L-Phe-L-His-L-Val-NH$_2$ (Ac-SEQ ID NO: 33)-NH$_2$) | 41.7 | 58.3 |
| 1 mg/mL Ac-L-Phe-L-Phe-L-Arg-L-Asp-L-Ile-L-Val-NH$_2$ (Ac-SEQ ID NO: 34)-NH$_2$) | 61.0 | 39.0 |
| 1 mg/mL Ac-L-Phe-L-Met-L-Gln-L-Asp-L-Ile-L-Val-NH$_2$ (Ac-SEQ ID NO: 35)-NH$_2$) | 90.3 | 9.7 |
| 1 mg/mL Ac-L-Phe-L-Phe-L-Gln-L-Asp-L-Ile-L-Val-NH$_2$ (Ac-SEQ ID NO: 36)-NH$_2$) | 64.1 | 35.9 |
| 1 mg/mL Ac-L-Phe-L-Met-L-Trp-L-Asp-L-Ile-L-Val-NH$_2$ (Ac-SEQ ID NO: 37)-NH$_2$) | 13.9 | 86.1 |
| 1 mg/mL Ac-L-Phe-L-Phe-L-Trp-L-Asp-L-Ile-L-Val-NH$_2$ (Ac-SEQ ID NO: 38)-NH$_2$) | 32.6 | 67.4 |

TABLE 3-continued

| Treatment | PAR-2 activity | Inhibition PAR-2 activity |
|---|---|---|
| 1 mg/mL Ac-L-Phe-L-Met-L-Arg-L-Phe-L-Ile-L-Val-$NH_2$ (Ac-SEQ ID NO: 39)-$NH_2$) | 59.1 | 40.9 |
| 1 mg/mL Ac-L-Ser-L-Met-L-Arg-L-Phe-L-Ile-L-Val-$NH_2$ (Ac-SEQ ID NO: 40)-$NH_2$) | 24.8 | 75.2 |
| 1 mg/mL Ac-L-Phe-L-Phe-L-Arg-L-Phe-L-Ile-L-Val-$NH_2$ (Ac-SEQ ID NO: 41)-$NH_2$) | 46.3 | 53.7 |
| 1 mg/mL Ac-L-Ser-L-Phe-L-Arg-L-Phe-L-Ile-L-Val-$NH_2$ (Ac-SEQ ID NO: 42)-$NH_2$) | 41.1 | 58.9 |
| 1 mg/mL Ac-L-Phe-L-Met-L-Gln-L-Phe-L-Ile-L-Val-$NH_2$ (Ac-SEQ ID NO: 43)-$NH_2$) | 71.4 | 28.6 |
| 1 mg/mL Ac-L-Ser-L-Met-L-Gln-L-Phe-L-Ile-L-Val-$NH_2$ (Ac-SEQ ID NO: 44)-$NH_2$) | 76.7 | 23.4 |
| 1 mg/mL Ac-L-Phe-L-Phe-L-Gln-L-Phe-L-Ile-L-Val-$NH_2$ (Ac-SEQ ID NO: 45)-$NH_2$) | 75.9 | 24.1 |
| 1 mg/mL Ac-L-Ser-L-Phe-L-Gln-L-Phe-L-Ile-L-Val-$NH_2$ (Ac-SEQ ID NO: 46)-$NH_2$) | 73.8 | 26.2 |
| 1 mg/mL Ac-L-Phe-L-Met-L-Trp-L-Phe-L-Ile-L-Val-$NH_2$ (Ac-SEQ ID NO: 47)-$NH_2$) | 79.3 | 20.7 |
| 1 mg/mL Ac-L-Ser-L-Met-L-Trp-L-Phe-L-Ile-L-Val-$NH_2$ (Ac-SEQ ID NO: 48)-$NH_2$) | 56.7 | 43.3 |
| 1 mg/mL Ac-L-Phe-L-Phe-L-Trp-L-Phe-L-Ile-L-Val-$NH_2$ (Ac-SEQ ID NO: 49)-$NH_2$) | 86.1 | 13.9 |

Example 9

Inhibition of Sensitization of TRPV1 Mediated by PAR-2 Activity in Sensory Neurons in Culture. Determination of CGRP Levels PAR-2 activation induces sensitization of the transient receptor potential vanilloid subfamily 1 (TRPV-1) in peptidergic sensory neurons, resulting in an entry of $Ca^{2+}$ which activates the intracellular signaling cascade and, concomitantly, leads to the release of pro-inflammatory peptides such as substance P (SP) and the α-calcitonin gene related peptide (CGRP), amplifying the response to pain, inflammation and itching [Dai Y. et al., "*Proteinase-Activated Receptor 2-Mediated Potentiation of Transient Receptor Potential Vanilloid Subfamily* 1 *Activity Reveals a Mechanism for Proteinase-Induced Inflammatory Pain*", (2004), *J. Neurosci.*, 24(18), 4293-4299]. Thus, the effectiveness and potential of the peptides in the inhibition of α-CGRP release due to TRPV-1 sensitization mediated by PAR-2 activity in in culture of rat DRG neurons was evaluated.

DRG neurons in culture were incubated with the different treatments at the indicated concentrations in buffer medium HBSS (Hank's Balanced salt solution) for 15 min at 37° C., after which the neurons were sensitized by treatment with the PAR-2 agonist I at 30 µM for 15 min at 37° C. Lastly α-CGRP release was induced by treatment with capsaicin 1 µM for 5 min at 37° C. The supernatants were collected and the amount of α-CGRP released was determined by enzyme immunoassay using the Rat CGRP EIA kit (SPI-Bio, Societe de Pharmacologie et d'Immunologie-BIO, France) following the supplier's instructions. The intensity of the color, determined by reading the absorbency at 405 nm, is proportional to the amount of CGRP released. The relative values of CGRP released were determined by double standardization with regard to the basal release of CGRP of the negative control (cells treated with HBSS) and the maximum releases of CGRP induced by the treatment with the cells with the PAR-2 agonist I and capsaicin. Table 4 details the values of CGRP determined for the different treatments.

TABLE 4

Levels of CGRP induced by sensitization of TRPV1 mediated by PAR-2 activity

| Treatment | % CGRP |
|---|---|
| HBSS | 0.0 |
| PAR-2 Agonist I/capsaicin | 100.0 |
| 25 µg/mL Ac-L-Phe-L-Met-L-Trp-L-Phe-L-His-L-Val-$NH_2$ (Ac-SEQ ID NO: 2)-$NH_2$) | 70.1 |
| 0.5 mg/mL Ac-L-Phe-L-Met-L-Trp-L-Phe-L-His-L-Val-$NH_2$ (Ac-SEQ ID NO: 30)-$NH_2$) | 20.2 |
| 25 µg/mL Ac-L-Phe-L-Phe-L-Trp-L-Phe-L-His-L-Val-$NH_2$ (Ac-SEQ ID NO: 32)-$NH_2$) | 58.9 |
| 0.5 mg/mL Ac-L-Phe-L-Phe-L-Trp-L-Phe-L-His-L-Val-$NH_2$ (Ac-SEQ ID NO: 32)-$NH_2$) | 17.7 |
| 25 µg/mL Ac-L-Phe-L-Phe-L-Trp-L-Asp-L-Ile-L-Val-$NH_2$ (Ac-SEQ ID NO: 38)-$NH_2$) | 78.7 |
| 0.5 mg/mL Ac-L-Phe-L-Phe-L-Trp-L-Asp-L-Ile-L-Val-$NH_2$ (Ac-SEQ ID NO: 38)-$NH_2$) | 20.3 |

The peptides were capable of inhibiting the release of CGRP induced by the sensitization of TRPV1 mediated by PAR-2 activity in a range of 20-40% at 25 µg/mL and about 80% at 0.5 mg/mL.

Example 10

Inhibition of the Release of IL-6 Induced by PAR-2 Activity in Human Keratinocytes Human keratinocytes were cultivated in supplemented Epilife® medium until confluence was achieved. The cells were then separated by treatment with trypsin and seeded at a density of 18,000 cells per well in 96-well plates pre-treated with collagen matrix. After 48 hours of incubation in supplemented Epilife® medium at 37° C. in a humidified atmosphere of 5% $CO_2$ a fresh medium was added with different concentrations of the product of the invention together with PAR2 Agonist I at 50 µM. Cells treated with supplemented Epilife® medium were added as a negative control (Control). The cells were incubated for another 48 hours under the same conditions, after which the supernatants were collected and the amount of IL-6 released was determined using the Human IL-6 ELISA Ready-SET-GOI® commercial kit (eBioscience, Inc.) following the supplier's instructions. The absorbance of each well was determined by reading the spectrophotometer Multiskan Ascent Reader at 450 nm correcting for each determination with its corresponding reading at 570 nm. The relative levels of IL-6 were calculated standardized with regard to the absorbance corresponding to the treatment of the cells with the PAR-2 Agonist I (maximum release of IL-6 in this cell model).

TABLE 5

Levels of IL-6 induced by PAR-2 activity

| Treatment | % IL-6 |
|---|---|
| Control | 42.7 |
| PAR-2 Agonist I | 100.0 |
| 0.1 mg/mL Ac-L-Phe-L-Met-L-Trp-L-Phe-L-His-L-Val-NH$_2$ (Ac-SEQ ID NO: 30)-NH$_2$) | 84.6 |
| 0.5 mg/mL Ac-L-Phe-L-Met-L-Trp-L-Phe-L-His-L-Val-NH$_2$ (Ac-SEQ ID NO: 30)-NH$_2$) | 42.3 |
| 0.1 mg/mL Ac-L-Phe-L-Phe-L-Trp-L-Phe-L-His-L-Val-NH$_2$ (Ac-SEQ ID NO: 32)-NH$_2$) | 61.8 |
| 0.5 mg/mL Ac-L-Phe-L-Phe-L-Trp-L-Phe-L-His-L-Val-NH$_2$ (Ac-SEQ ID NO: 32)-NH$_2$) | 30.4 |
| 0.1 mg/mL Ac-L-Phe-L-Phe-L-Trp-L-Asp-L-Ile-L-Val-NH$_2$ (Ac-SEQ ID NO: 38)-NH$_2$) | 36.2 |
| 0.5 mg/mL Ac-L-Phe-L-Phe-L-Trp-L-Asp-L-Ile-L-Val-NH$_2$ (Ac-SEQ ID NO: 38)-NH$_2$) | 11.5 |

The peptides were capable of inhibiting the release of IL-6 induced by PAR-2 activity with a growing dose-response.

Example 11

Effect of Ac-L-Phe-L-Phe-L-Trp-L-Phe-L-his-L-Val-NH$_2$ (Ac-(SEQ ID NO:32)-NH$_2$) on the Proliferation of Human Epidermal Keratinocytes in Culture Cell proliferation was evaluated by a fluorescence-based cell viability method, in which the live cells are distinguished from the dead cells by the enzymatic conversion of calcein-AM to its fluorescent form.

Human keratinocytes were cultivated in DMEM supplemented with fetal bovine serum (FBS) until confluence was achieved. The cells were then separated using trypsin and were seeded at a density of 100,000 cells per well in 96-well plates. After 24 hours of incubation in DMEM at 37° C. in a humidified atmosphere at 5% CO$_2$ a fresh medium was added with different concentrations of the product of the invention. Cells treated with DMEM as a negative control were used. The cells were incubated for another 24 hours under the same conditions and the medium was substituted by 100 µl of calcein-AM (Molecular Probes) at 0.4 µM diluted in phosphate buffered saline (PBS). After 30 minutes of incubation at 37° C. the fluorescence was measured at excitation 485 nm and emission 530 nm in a plate reader (Genios, Tecan). The total growth percentage was calculated as T/C×100 wherein T is the fluorescence of the wells treated with the peptides of the invention and C the fluorescence of the control wells treated with DMEM.

Table 6 shows the values of the stimulation of human epidermal keratinocyte proliferation after incubation with the peptides of the invention at the stated concentrations, calculated as [(T-C)/C].

TABLE 6

Proliferation of human epidermal keratinocytes

| Treatment | % Stimulation of proliferation |
|---|---|
| Control | 0.0 |
| 10 µg/mL Ac-L-Phe-L-Phe-L-Trp-L-Phe-L-His-L-Val-NH$_2$ (Ac-SEQ ID NO: 32)-NH$_2$) | 21.3 |
| 25 µg/mL Ac-L-Phe-L-Phe-L-Trp-L-Phe-L-His-L-Val-NH$_2$ (Ac-SEQ ID NO: 32)-NH$_2$) | 23.2 |

The peptide Ac-L-Phe-L-Phe-L-Trp-L-Phe-L-His-L-Val-NH$_2$ (Ac-(SEQ ID NO:32)-NH$_2$) stimulated the proliferation of human keratinocytes by 23% at 25 µg/mL, therefore improving the barrier function of the skin.

Example 12

Evaluation of the Induction of Healing Through Treatment with Ac-L-Phe-L-Phe-L-Trp-L-Phe-L-his-L-Val-NH$_2$ (Ac-(SEQ ID NO:32)-NH$_2$) in Human Epidermal Keratinocytes in Culture Human keratinocytes were cultivated in DMEM supplemented with fetal bovine serum (FBS) until confluence was achieved. The cells were then separated using trypsin and were seeded at a density of 50,000 cells per well in 48-well plates. After 48 hours of incubation in DMEM at 37° C. in a humidified atmosphere at 5% CO$_2$ a cut in the cultivation with a pipette point to create an area without cells simulating an injury and photographs were taken of said area with a Zeiss Axiovert 40 CFL microscope equipped with a AxioCam MRc5 camera, calculating the area of the zone without cells using the (A0) equipment software. A fresh medium was then added with different concentrations of the product of the invention. Cells treated with DMEM as a negative control were used, and cells treated with DMEM and FBS as the positive healing control. The cells were incubated for another 48 hours under the same conditions to enable cell migration in the injury area, after which photographs were taken of the injury area once again and the corresponding areas of the zones without cells were calculated (A48).

The healing percentage was calculated as the ratio of the reduction to the area without cells after 48 hours and the area without cells before incubation with the peptide [(A0-A48)/A0]. Table 7 shows the healing values after incubation with the peptides of the invention at the stated concentrations.

TABLE 7

Healing of human epidermal keratinocyte

| Treatment | % Healing |
|---|---|
| Negative control | 20.5 |
| Positive control | 100.0 |
| 25 µg/mL Ac-L-Phe-L-Phe-L-Trp-L-Phe-L-His-L-Val-NH$_2$ (Ac-(SEQ ID NO: 32)-NH$_2$) | 40.0 |
| 0.5 mg/mL Ac-L-Phe-L-Phe-L-Trp-L-Phe-L-His-L-Val-NH$_2$ (Ac-(SEQ ID NO: 32)-NH$_2$) | 44.8 |

The peptide Ac-L-Phe-L-Phe-L-Trp-L-Phe-L-His-L-Val-NH$_2$ (Ac-(SEQ ID NO:32)-NH$_2$) stimulated healing of human keratinocytes by 45% at 0.5 mg/mL, therefore improving skin healing.

Example 13

Assay of the Photoprotective Effectiveness of Ac-L-Phe-L-Phe-L-Trp-L-Phe-L-his-L-Val-NH$_2$ (Ac-(SEQ ID NO:32)-NH$_2$) in Human Dermal Fibroblasts in Culture The human dermal fibroblasts were maintained in culture for 24 hours in 96-well plates for the formation of monolayers and the cells were preincubated in the dark with 10 μg/mL of Ac-L-Phe-L-Phe-L-Trp-L-Phe-L-His-L-Val-NH$_2$ or phosphate buffered saline (irradiated control, IC) for 1 hour at 37° C. and humidified air with 5% CO$_2$. The cells were then irradiated with a solar simulation lamp with an energy of 37 J/cm$^2$ at room temperature for 150 min. A control plate was kept in the dark for the same time at room temperature (non-irradiated control, NIC). After the irradiation period the cell medium was replaced by a fresh one and the cells were incubated for another 24 hours. Cell viability was determined by Neutral Red dye, measuring the optical density at 540 nm in a spectrophotometer, standardizing the values of each simple with regard to the cell viability of the non-irradiated control sample (CV$_{NIC}$).

Table 8 shows the photoprotective effectiveness of Ac-L-Phe-L-Phe-L-Trp-L-Phe-L-His-L-Val-NH$_2$, which was determined by comparing the viability obtained in the cells treated with the peptide of the invention (CV) with regard to the irradiated control cell response (CVO by formula (CV$_i$−CV$_{IC}$)/CV$_{IC}$.

TABLE 8

Photoprotective effectiveness in human dermal fibroblasts

| TREATMENT | CELL VIABILITY (%) | % PHOTOPROTECTIVE EFFECTIVENESS |
|---|---|---|
| Non-irradiated control | 100.0 | — |
| Irradiated control | 18.0 | — |
| 0.01 μg/mL Ac-L-Phe-L-Phe-L-Trp-L-Phe-L-His-L-Val-NH$_2$ (Ac-(SEQ ID NO: 32)-NH$_2$) | 37.1 | 105.9 |

Example 14

Preparation of Coacervates of Nanostructured Lipid Carriers Containing Ac-L-Phe-L-Phe-L-Trp-L-Phe-L-his-L-Val-NH$_2$(Ac-(SEQ ID NO:32)-NH$_2$ In a suitable beaker the following were added in this order: water [INCI: Water (Aqua)], hydroxypropyl starch phosphate [INCI: Hydroxypropyl Starch Phosphate], *sclerotium* gum [INCI: *Sclerotium* Gum], sodium hyaluronate [INCI: Sodium Hyaluronate], propanediol [INCI: Propanediol], phenoxyethanol [INCI: Phenoxyethanol] (phase A ingredients). It was stirred until complete solution, after which it was heated to 70° C.

In a separate beaker the following were mixed together: sorbitan sesquiolate [INCI: SORBITAN SESQUIOLEATE], caprylic/capric triglycerides [INCI: CAPRYLIC/CAPRIC TRIGLYCERIDES] and isohexadecane [INCI: ISOHEXADECANE] until complete homogenization heating to 85° C., after which the peptide Ac-L-Phe-L-Phe-L-Trp-L-Phe-L-His-L-Val-NH$_2$ was added.

Once the two phases were obtained, phase B was added to phase A little by little under stirring, after which the size of the particles of the mixture were reduced with a high pressure Microfluidizer®.

Separately, QUAT-SOY LDMA-25 [INCI: Water (Aqua), Lauryldimonium hydroxypropyl Hydrolyzed Soy Protein was dissolved in water [INCI: Water (Aqua)] in another beaker and added to the previous mixture. Finally, phase D was added little by little under stirring, obtaining a cosmetic composition with the proportions shown in Table 9.

TABLE 9

Coacervates of nanostructured lipid carriers

| Phase | INGREDIENT | % in weight |
|---|---|---|
| A | WATER (AQUA) | q.s.p. 100 |
| A | HYDROXYPROPYL STARCH PHOSPHATE | 0.3 |
| A | SCLEROTIUM GUM | 0.1 |
| A | SODIUM HYALURONATE | 0.01 |
| A | PROPANEDIOL | 5 |
| A | PHENOXYETHANOL | 2.5 |
| B | SORBITAN SESQUIOLEATE | 5 |
| B | ISOHEXADECANE | 5 |
| B | Ac-L-Phe-L-Phe-L-Trp-L-Phe-L-His-L-Val-NH$_2$ | 0.05 |
| B | CAPRYLIC/CAPRIC TRIGLYCERIDES | 8 |
| C | WATER (AQUA) | 4.25 |
| C | QUAT-SOY LDMA-25 | 0.2 |
| D | HYDROXYPROPYL STARCH PHOSPHATE | 1.5 |
| D | SCLEROTIUM GUM | 1.5 |

Example 15

Preparation of Liposomes Containing Ac-L-Phe-L-Met-L-Trp-L-Phe-L-his-L-Val-NH$_2$ (Ac-(SEQ ID NO:30)-NH$_2$)

In a suitable beaker the preservatives propanediol [INCI: Propanediol], phenoxyethanol [INCI: Phenoxyethanol] were mixed with water until complete solution (phase A). Afterwards, lecithin [INCI: LECITHIN] was incorporated little by little under stirring to phase A, maintaining the stirring until obtaining a homogenous dispersion. In a separate beaker, caprylic/capric triglycerides [INCI: CAPRYLIC/CAPRIC TRIGLYCERIDES] and isohexadecane [INCI: ISOHEXADECANE] were mixed, after which the peptide Ac-L-Phe-L-Phe-L-Trp-L-Phe-L-His-L-Val-NH$_2$ (phase C) was dispersed. Next, phase C was added slowly to phase A and B and was stirred until completely homogenized. Finally, the mixture was passed through a high pressure Microfluidizer®.

TABLE 10

Liposomes

| Phase | INGREDIENT | % in weight |
|---|---|---|
| A | AQUA (WATER) | Qsp 100 |
| A | PROPANEDIOL | 5 |
| A | PHENOXYETHANOL | 2.5 |
| B | LECITHIN | 4 |
| C | CAPRYLIC/CAPRIC TRIGLYCERIDES | 5 |
| C | ISOHEXADECANE | 3 |
| C | Ac-L-Phe-L-Met-L-Trp-L-Phe-L-His-L-Val-NH$_2$ (Ac-SEQ ID NO: 30)-NH$_2$) | 0.05 |

Example 16

Preparation of a Cosmetic Facial Composition Containing Ac-L-Phe-L-Phe-L-Trp-L-Phe-L-his-L-Val-NH$_2$(Ac-(SEQ ID NO:32)-NH$_2$)

In a suitable beaker betaine [INCI: BETAINE] and disodium EDTA [INCI: DISODIUM EDTA] were dissolved in water [INCI: WATER (AQUA)] (Phase A), after which phase B was added, stirring until complete incorporation. In a separate beaker, caprylic/capric triglycerides [INCI: CAPRYLIC/CAPRIC TRIGLYCERIDES], tocopheryl acetate [INCI: TOCOPHERYL ACETATE] (phase C) were mixed together until complete homogenization and added to phase C on the mixture of A and B. In another separate beaker, citric acid [INCI: CITRIC ACID] was dissolved in water [INCI: WATER (AQUA)], after which butylene glycol [INCI: BUTYLENE GLYCOL] was incorporated and finally the peptide Ac-L-Phe-L-Phe-L-Trp-L-Phe-L-His-L-Val-NH$_2$ (phase E). Once the resulting mixture was dissolved, phases D and E were added to the mixture of A, B and C. Afterwards polymethyl methacrylate [INCI: POLYMETHYL METHACRYLATE] (phase F) and MIKROKILL ECT (phase G) were added under constant stirring until complete incorporation. The pH was adjusted to 6.0, after which the fragrance from phase I was added under stirring.

TABLE 11

Cosmetic facial composition

| Phase | INGREDIENT | % in weight |
|---|---|---|
| A | WATER (AQUA) | Qsp 100 |
| A | BETAINE | 2.00 |
| A | DISODIUM EDTA | 0.30 |
| B | SODIUM ACRYLATES COPOLYMER | 2.00 |
| C | ISONONYL ISONONANOATE | 4.00 |
| C | BUTYLENE GLYCOL DICAPRYLATE/DICAPRATE | 3.00 |
| C | CAPRYLIC/CAPRIC TRIGLYCERIDE | 3.00 |
| C | TOCOPHERYL ACETATE | 0.50 |
| D | ANTARCTICINE ® C (INCI: WATER (AQUA), *PSEUDOALTEROMONAS* FERMENT EXTRACT, CAPRYLYL GLYCOL) | 4.00 |
| E | Ac-L-Phe-L-Phe-L-Trp-L-Phe-L-His-L-Val-NH$_2$ (Ac-SEQ ID NO: 32)-NH$_2$) | 0.001 |
| E | BUTYLENE GLYCOL | 3.2 |
| E | WATER (AQUA) | 0.8 |
| E | CITRIC ACID | 0.04 |
| F | POLYMETHYL METHACRYLATE | 2.00 |
| G | MIKROKILL ECT (INCI: BENZYL ALCOHOL, SALICYLIC ACID, GLYCERIN, SORBIC ACID) | 1.00 |
| H | 20% SODIUM HYDROXIDE | Qsp pH 6.0 |
| I | FRAGRANCE (PARFUM) | 0.15 |

Example 17

Preparation of a Facial Cosmetic Composition Containing Ac-L-Phe-L-Phe-L-Trp-L-Phe-L-his-L-Val-NH$_2$(Ac-(SEQ ID NO:32)-NH$_2$)

In a suitable beaker pentylene glycol [INCI: PENTYLENE GLYCOL] and benzyl alcohol [INCI: BENZYL ALCOHOL] were mixed together with water [INCI: WATER (AQUA)] (phase A). Afterwards, carbomer [INCI: CARBOMER] and potassium cetyl phosphate [INCI: POTASSIUM CETYL PHOSPHATE] were added under constant stirring, after which the mixture was heated to 70-75° C. In a separate beaker, the components ethylhexyl cocoate [INCI: ETHYLHEXYL COCOATE], C12-15 alkyl benzoate [INCI: C12-15 ALKYL BENZOATE], phenoxyethanol [INCI: PHENOXYETHANOL], PHYTOCREAM 2000® [INCI: GLYCERYL STEARATE, CETEARYL ALCOHOL, POTASSIUM PALMITOYL HYDROLYZED WHEAT PROTEIN] and tocopheryl acetate [INCI: TOCOPHERYL ACETATE] (phase B) were mixed together and heated to 70-75° C. The heated phase B was added to phases A+A1+A2 and were stirred with a turbine to form the emulsion. Stirring was maintained until it reached 40° C., after which the peptide Ac-L-Phe-L-Phe-L-Trp-L-Phe-L-His-L-Val-NH$_2$, citric acid [INCI: CITRIC ACID] in water [INCI: WATER (AQUA)], butylene glycol [INCI: BUTYLENE GLYCOL] (phase C) and dimethicone silicone [INCI: DIMETHICONE] were added. Sepigel® 305 [INCI: POLYACRYLAMIDE, WATER (AQUA), C13-14 ISOPARAFFIN, LAURETH-7] was added under stirring and afterwards the fragrance [INCI: FRAGRANCE (PARFUM)]. Finally, phase G was added little by little until the pH was adjusted to 5.5-7.0.

TABLE 12

Facial cosmetic composition

| Phase | INGREDIENT | % in weight |
|---|---|---|
| A | WATER (AQUA) | 75.000 |
| A | PENTYLENE GLYCOL | 5.000 |
| A | BENZYL ALCOHOL | 1.000 |
| A1 | CARBOMER | 0.500 |
| A2 | POTASSIUM CETYL PHOSPHATE | 0.500 |
| B | ETHYLHEXYL COCOATE | 5.000 |
| B | C12-15 ALKYL BENZOATE | 5.000 |
| B | PHENOXYETHANOL | 0.900 |
| B | PHYTOCREAM 2000 ® (INCI: GLYCERYL STEARATE, CETEARYL ALCOHOL, POTASSIUM PALMITOYL HYDROLYZED WHEAT PROTEIN) | 5.000 |
| B | TOCOPHERYL ACETATE | 0.500 |
| C | Ac-L-Phe-L-Phe-L-Trp-L-Phe-L-His-L-Val-NH$_2$ | 0.001 |
| C | BUTYLENE GLYCOL | 3.2 |
| C | WATER (AQUA) | 0.759 |
| C | CITRIC ACID | 0.04 |
| D | DIMETHICONE | 1.000 |
| E | SEPIGEL ® 305 (INCI: POLYACRYLAMIDE, WATER (AQUA), C13-14 ISOPARAFFIN, LAURETH-7) | 1.000 |
| F | FRAGRANCE (PARFUM) | 0.100 |
| G | 20% SODIUM HYDROXIDE | qsp pH 5.5-7.0 |

Example 18

Preparation of a Body Lotion Containing Ac-L-Phe-L-Phe-L-Trp-L-Asp-L-Ile-L-Val-NH$_2$ (Ac-(SEQ ID NO:38)-NH$_2$)

In a suitable beaker pentylene glycol [INCI: PENTYLENE GLYCOL], propylene glycol [INCI: PROPYLENE GLYCOL], glycerin [INCI: GLYCERIN], panthenol [INCI: PANTHENOL] and benzyl alcohol [INCI: BENZYL ALCOHOL] with water [INCI: WATER (AQUA)] (phase A) were dissolved under constant, light stirring. Once homogenized, phase A1 was added and stirring was maintained until complete solution. In a separate beaker the components from phase B were mixed together and, once homogenized, phase B was added little by little to phase A under constant stirring. In another separate beaker, citric acid [INCI: CITRIC ACID] was dissolved in water [INCI: WATER (AQUA)], butylene glycol was added [INCI: BUTYLENE GLYCOL], after which the peptide of the invention was dissolved. This mixture was added to phases A+B under constant stirring. Afterwards, phase D was added, also under constant stirring. Once the mixture was left homogenous, Sepigel® 305 was added and the pH was adjusted to 6.0-6.5 with phase F. Finally, the fragrance was added.

TABLE 13

Body lotion composition

| Phase | INGREDIENT | % in weight |
|---|---|---|
| A | WATER (AQUA) | qsp 100 |
| A | PENTYLENE GLYCOL | 5.000 |
| A | GLYCERIN | 2.000 |
| A | PROPYLENE GLYCOL | 2.000 |
| A | BENZYL ALCOHOL | 1.000 |
| A | PANTHENOL | 1.000 |
| A1 | ACRYLATES/C10-30 ALKYL ACRYLATE CROSSPOLYMER | 0.300 |
| B | ISOHEXADECANE | 3.000 |
| B | TRIETHYLHEXANOIN | 3.000 |
| B | SILICONE DC 1401 (INCI: CYCLOMETHICONE, DIMETHICONOL) | 1.000 |
| B | DIMETHICONE | 1.000 |
| B | PHENOXYETHANOL | 0.900 |
| B | TOCOPHERYL ACETATE | 0.500 |
| C | Ac-L-Phe-L-Phe-L-Trp-L-Asp-L-Ile-L-Val-$NH_2$ (Ac-SEQ ID NO: 38)-$NH_2$) | 0.0005 |
| C | BUTYLENE GLYCOL | 1.6 |
| C | WATER (AQUA) | 0.4 |
| C | CITRIC ACID | 0.02 |
| D | XPERTMOIST ™ (INCI: WATER (AQUA), GLYCERIN, PSEUDOALTEROMONAS FERMENT EXTRACT, XANTHAN GUM, PROLINE, ALANINE, SERINE, SODIUM PHOSPHATE, SODIUM HYDROXIDE, CAPRYLYL GLYCOL, ETHYLHEXYLGLYCERIN) | 7.000 |
| E | SEPIGEL ® 305 (INCI: POLYACRYLAMIDE, WATER (AQUA), C13-14 ISOPARAFFIN, LAURETH-7) | 2.000 |
| F | 20% SODIUM HYDROXIDE | qsp pH 6.0-6.5 |
| G | FRAGRANCE (PARFUM) | 0.150 |

Example 19

Preparation of a Capillary Lotion Containing Ac-L-Phe-L-Phe-L-Trp-L-Phe-L-his-L-Val-$NH_2$ In a suitable beaker the components of phase A are dissolved under constant, light stirring. In a separate beaker, the citric acid is dissolved in water and the butylene glycol is added, after which the peptide of the invention is added. Once homogenized, phase B is added to phase A under constant stirring until complete homogenization.

TABLE 14

Capillary lotion composition

| Phase | INGREDIENT | % in weight |
|---|---|---|
| A | ALCOHOL DENAT | 50 |
| A | WATER (AQUA) | qsp 100 |
| A | PANTHENOL | 0.1 |
| A | ZINC RICINOLEATE | 0.1 |
| A | FRAGRANCE (PARFUM) | 0.15 |
| B | Ac-L-Phe-L-Phe-L-Trp-L-Phe-L-His-L-Val-$NH_2$ | 0.0005 |
| B | BUTYLENE GLYCOL | 1.6 |
| B | WATER (AQUA) | 0.4 |
| B | CITRIC ACID | 0.02 |

Example 20

Preparation of a Mouthwash Containing Ac-L-Phe-L-Phe-L-Trp-L-Phe-L-his-L-Val-$NH_2$ In a suitable beaker the components of phase A are dissolved under constant, light stirring. In a separate beaker, the citric acid is dissolved in the water and the butylene glycol is added, after which the peptide of the invention is dissolved. Once homogenized, phase B is added to phase A under stirring until complete homogenization.

TABLE 15

Mouthwash composition

| Phase | INGREDIENT | % in weight |
|---|---|---|
| A | WATER (AQUA) | qsp 100 |
| A | ALCOHOL DENAT | 15 |
| A | SODIUM SACCARIN | 0.02 |
| A | SORBITOL | 5 |
| A | PROPYLENE GLYCOL | 10 |
| A | PEG-60 HYDROGENATED CASTOR OIL | 2 |
| B | Ac-L-Phe-L-Phe-L-Trp-L-Phe-L-His-L-Val-$NH_2$ | 0.0005 |
| B | BUTYLENE GLYCOL | 1.6 |
| B | WATER (AQUA) | 0.4 |
| B | CITRIC ACID | 0.02 |

Example 21

Effect of the Composition of Example 17 on the Reduction of the Stinging Caused by the Application of Capsaicin to the Skin A study of the stinging induced by the application of capsaicin was carried out on 12 Caucasian volunteers between the ages of 20 and 45, selected with a degree of response in a Stinging test (subjective self-evaluation of the intensity of the stinging after the application of a solution of capsaicin to the forearm) of 1-3 (0 no stinging, 3 intense stinging). Throughout the duration of the study the subjects did not use different products on the areas tested and avoided exposure to UV radiation. The volunteers applied the composition of Example 17 to one forearm and a placebo composition (the same composition from Example 17 without the peptide) to the other forearm, twice a day for 7 days, after which a 0.05% solution of *Capsicum frutescens* in sunflower seed oil was applied to each forearm (final concentration of capsaicin of 0.03%). The subjective self-evaluation of the intensity of the stinging was carried out again 15 min after the application of capsaicin, and the reduction in the stinging sensation was determined for each measurement point with regard to the forearm treated with the placebo composition.

The reduction in the stinging obtained by treatment of the skin with the cream from Example 17 is shown in Table 16.

TABLE 16

Evaluation of the reduction in the stinging induced by application of capsaicin to the skin

| | Degree of stinging Placebo cream | Degree of stinging Cream Example 17 | % Reduction stinging |
|---|---|---|---|
| $T_{15\,min}$ | 2.17 | 1.33 | 38.5 |

The results obtained show that the formulation of Example 17 reduces the stinging on the skin by 38.5% with regard to the placebo formulation 15 min after the application of capsaicin.

Example 22

Preparation of a Cosmetic Composition Containing Coacervates of Nanostructured Lipid Carriers of Ac-L-Phe-L-Phe-L-Trp-L-Phe-L-his-L-Val-NH$_2$ The cosmetic composition of the Example 17 was prepared, but replacing the peptide of that example by the coacervated nanostructured lipid carriers of Example 14 and with the amounts of table 17.

TABLE 17

Cosmetic composition

| Phase | INGREDIENT | % in weight |
|---|---|---|
| A | WATER (AQUA) | 74.000 |
| A | PENTYLENE GLYCOL | 5.000 |
| A | BENZYL ALCOHOL | 1.000 |
| A1 | CARBOMER | 0.500 |
| A2 | POTASSIUM CETYL PHOSPHATE | 0.500 |
| B | ETHYLHEXYL COCOATE | 5.000 |
| B | C12-15 ALKYL BENZOATE | 5.000 |
| B | PHENOXYETHANOL | 0.900 |
| B | PHYTOCREAM 2000 ® (INCI: GLYCERYL STEARATE, CETEARYL ALCOHOL, POTASSIUM PALMITOYL HYDROLYZED WHEAT PROTEIN) | 5.000 |
| B | TOCOPHERYL ACETATE | 0.500 |
| C | Composition Example 14 | 1.000 |
| C | BUTYLENE GLYCOL | 3.2 |
| C | WATER (AQUA) | 0.759 |
| C | CITRIC ACID | 0.04 |
| D | DIMETHICONE | 1.000 |
| E | SEPIGEL ® 305 (INCI: POLYACRYLAMIDE, WATER (AQUA), C13-14 ISOPARAFFIN, LAURETH-7) | 1.000 |
| F | FRAGRANCE (PARFUM) | 0.100 |
| G | 20% SODIUM HYDROXIDE | qsp pH 5.5-7.0 |

Example 23

Preparation of a Facial Cosmetic Composition Containing Ac-L-Phe-L-Phe-L-Trp-L-Phe-L-his-L-Val-NH$_2$ In a suitable beaker pentylene glycol [INCI: PENTYLENE GLYCOL] and benzyl alcohol [INCI: BENZYL ALCOHOL] were mixed together in water [INCI: WATER (AQUA)], and then carbomer [INCI: CARBOMER] was added little by little under stirring until complete solution. Afterwards, potassium cetyl phosphate [INCI: POTASSIUM CETYL PHOSPHATE] was added under constant stirring to dispersion, and the mixture was heated to 70-75° C. (phases A+A1+A2). In a separate beaker, the components ethylhexyl cocoate [INCI: ETHYLHEXYL COCOATE], C12-15 alkyl benzoate [INCI: C12-15 ALKYL BENZOATE], phenoxyethanol [INCI: PHENOXYETHANOL], PHYTOCREAM 2000® [INCI: GLYCERYL STEARATE, CETEARYL ALCOHOL, POTASSIUM PALMITOYL HYDROLYZED WHEAT PROTEIN] and tocopheryl acetate [INCI: TOCOPHERYL ACETATE] (phase B) were mixed together and heated to 70-75° C. The heated phase B was added to phases A+A1+A2 and were stirred with a turbine to form the emulsion. Stirring was maintained until it reached 50° C., after which the peptide Ac-L-Phe-L-Phe-L-Trp-L-Phe-L-His-L-Val-NH$_2$, citric acid [INCI: CITRIC ACID] in water [INCI: WATER (AQUA)], butylene glycol [INCI: BUTYLENE GLYCOL] (phase C) and dimethicone silicone [INCI: DIMETHICONE] were added. Sepigel® 305 [INCI: POLYACRYLAMIDE, WATER (AQUA), C13-14 ISOPARAFFIN, LAURETH-7] was added under stirring. Afterwards the fragrance [INCI: FRAGRANCE (PARFUM)], cinnamal [INCI: CINNAMAL] and farnesol [INCI: FARNESOL] were also added under stirring. Finally, phase G was added little by little until the pH was adjusted to 6.0-6.5.

TABLE 18

Facial cosmetic composition

| Phase | INGREDIENT | % in weight |
|---|---|---|
| A | WATER (AQUA) | 71.600 |
| A | PENTYLENE GLYCOL | 5.000 |
| A | BENZYL ALCOHOL | 1.000 |
| A1 | CARBOMER | 0.500 |
| A2 | POTASSIUM CETYL PHOSPHATE | 0.500 |
| B | ETHYLHEXYL COCOATE | 2.500 |
| B | C12-15 ALKYL BENZOATE | 5.000 |
| B | PHENOXYETHANOL | 0.900 |
| B | GLYCERYL STEARATE, | 2.050 |
| B | CETEARYL ALCOHOL, | 2.050 |
| B | POTASSIUM PALMITOYL HYDROLYZED WHEAT PROTEIN | 0.900 |
| B | TOCOPHERYL ACETATE | 0.500 |
| C | Ac-L-Phe-L-Phe-L-Trp-L-Phe-L-His-L-Val-NH$_2$ | 0.001 |
| C | BUTYLENE GLYCOL | 3.2 |
| C | WATER (AQUA) | 0.759 |
| C | CITRIC ACID | 0.04 |
| D | DIMETHICONE | 1.000 |
| E | POLYACRYLAMIDE | 0.400 |
| E | WATER (AQUA) | 0.340 |
| E | C13-14 ISOPARAFFIN | 0.200 |
| E | LAURETH-7 | 0.060 |
| F | FRAGRANCE (PARFUM) | 0.100 |
| F | CINNAMAL | 0.400 |
| F | FARNESOL | 1.000 |
| G | 20% SODIUM HYDROXIDE | qsp pH 6.0-6.5 |

Example 24

In Vivo Study of Skin Hydration

A comparative in vivo study of the hydrating capacity of the skin of the cosmetic composition in example 22 and its placebo composition, which contained the same ingredients and in the same percentages as the composition of example 22, except the peptide of the invention, Ac-L-Phe-L-Phe-L-Trp-L-Phe-L-His-L-Val-NH$_2$, which was substituted by water.

The measurements of this study were carried out after the test persons were acclimatized for 45 minutes in a bioclimatic room (22° C.; 60% relative humidity) and with the purpose of maintaining the temperature and humidity constant during the measuring. The measurements of skin hydration were carried out on the legs using a Corneometer® CM 825 (Courage & Khazaka, Germany). Twenty women with an age between 18 and 55, with sensitive skin and itch sensation on their legs participated in the study; they were instructed not to apply any cosmetic or dermopharmaceutical composition other than those used in the study during its duration, or 7 days prior to the beginning of the study.

All the volunteers applied the placebo composition on their right leg and the cosmetic composition from Example 22 on their left legs twice a day for 4 weeks, always applying the placebo composition to the right leg and the composition from example 22 to the left leg. The volunteers did not apply any cosmetic composition for at least 10 hours before undertaking the instrumental measurements. Skin measurement values were measured at three different places within the respective testing areas. The recorded values were averaged.

The skin hydration measurements were taken before the beginning of the study and a1 and 4 weeks after the first application of the previous compositions.

Table 19 shows the averaged change of skin moisture with the cosmetic composition of example 22 in respect to the placebo composition calculated as [(averaged improvement of composition of example 22)–(averaged improvement of placebo composition)]/(averaged improvement of placebo composition)*100.

TABLE 19

| time | % difference respect placebo composition |
|---|---|
| 1 week | 34.0% |
| 4 weeks | 39.2% |

The results in the table clearly show that the composition from example 22 has greater skin hydration power than the placebo composition, and therefore it is demonstrated that the compound Ac-L-Phe-L-Phe-L-Trp-L-Phe-L-His-L-Val-NH$_2$ improves the skin's hydration in vivo.

Example 25

Anti-Sensitizing Potential of a Cosmetic Cream of Example 23 Containing Ac-L-Phe-L-Phe-L-Trp-L-Phe-L-his-L-Val-NH$_2$ in Reconstructed Human Epidermis (RHE)

Cosmetic creams containing parfums normally show allergic reactions due to some allergenic components like cinnamal or farnesol. The purpose of this experiment was to evaluate the anti-sensitizing potential of a cosmetic cream of Example 23 containing cinnamal, farnesol and the peptide Ac-L-Phe-L-Phe-L-Trp-L-Phe-L-His-L-Val-NH$_2$, compared with a placebo cream (composition of Example 23 without the ingredients of phase C). In order to determine the anti-sensitizing potential the level of interleukin-8, IL-8 was measured for both creams in RHE tissues after 24 h of cream application.

Commercial RHE tissues (SkinEthic, Lyon, RHE/S/17) (0.5 cm$^2$) were treated in triplicate with 15 µg of the composition of Example 23 and the placebo composition over the surface of the tissue. After 24 hours of incubation in growth medium at 37° C. in a humidified atmosphere at 5% CO$_2$, the IL-8 expression in the treated RHE tissues was determined using the ELISA Interleukin detection kit (Invitrogen) following the supplier's instructions. The absorbance was determined by reading the spectrophotometer Synergy MX, Biotek, at 450 nm.

TABLE 20

| Test Condition | IL-8 expression (pg/ml) average 3 tissues |
|---|---|
| Composition Example 23 | 79 |
| Placebo Composition | 189 |

The test shown a reduction of the expression of IL-8 for the composition of example 23 versus the placebo composition, and therefore the peptide Ac-L-Phe-L-Phe-L-Trp-L-Phe-L-His-L-Val-NH$_2$ proved to highly counteract the release of cytokines induced by cosmetic allergens such as cinnamal and farnesol.

The invention claimed is:

1. A peptide of general formula (I)

$$R_1\text{-}X_m\text{-}AA_1\text{-}AA_2\text{-}AA_3\text{-}AA_4\text{-}AA_5\text{-}AA_6\text{-}Y_p\text{-}R_2 \quad (I)$$

its stereoisomers, mixtures thereof and/or its cosmetic or pharmaceutical acceptable salts, wherein:

$AA_1$ is -Phe-, $AA_2$ is -Met-, $AA_3$ is -Trp-, $AA_4$ is -Phe-, $AA_5$ is -His-, and $AA_6$ is -L-Val-; or $AA_1$ is -Phe-, $AA_2$ is -Phe-, $AA_3$ is -Trp-, $AA_4$ is -Phe-, $AA_5$ is -His-, and $AA_6$ is -L-Val-; or $AA_1$ is -Phe-, $AA_2$ is -Phe-, $AA_3$ is -Trp-, $AA_4$ is -Asp-, $AA_5$ is -Ile-, and $AA_6$ is -L-Val-;

X and Y are amino acids and are independently selected from amongst themselves;

m and p are independently selected from amongst themselves and have a value of 0 or 1;

m+p is smaller than 2;

$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ or $R_2$ are not α-amino acids.

2. The peptide according to claim 1, wherein $R_1$ is selected from the group consisting of H and $R_5$—CO— wherein $R_5$ is selected from the group consisting of substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl with 3-10 ring members and substituted or unsubstituted heteroarylalkyl of 2 to 24 carbon atoms and 1 to 3 atoms other than carbon and an alkyl chain of 1 to 6 carbon atoms.

3. The peptide according to claim 2, wherein $R_1$ is selected from the group consisting of H, acetyl, tert-butanol, hexanoyl, 2-methylhexanoyl, cyclohexanecarboxyl, octanoyl, decanoyl, lauroyl, myristoyl, palmitoyl, stearoyl, oleoyl and linoleoyl.

4. The peptide according to claim 1, wherein $R_2$ is —$NR_3R_4$ or —$OR_3$, wherein $R_3$ and $R_4$ are independently selected from the group consisting of H, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl with 3-10 ring members, and substituted or unsubstituted heteroarylalkyl of 2 to 24 carbon atoms and 1 to 3 atoms other than carbon and an alkyl chain of 1 to 6 carbon atoms.

5. The peptide according to claim 4, wherein $R_3$ and $R_4$ are independently selected from the group consisting of H, methyl, ethyl, hexyl, dodecyl and hexadecyl.

6. The peptide according to claim 1, wherein $R_1$ is selected from the group consisting of H, acetyl, lauroyl, myristoyl and palmitoyl and $R_2$ is —$NR_3R_4$ or —$OR_3$ wherein $R_3$ and $R_4$ are independently selected from H, methyl, ethyl, hexyl, dodecyl and hexadecyl.

7. A process for preparing a peptide of general formula (I), its stereoisomers, mixtures thereof and/or its cosmetically or pharmaceutically acceptable salts, according to claim 1, wherein the preparation process is carried out in solid phase or solution.

8. A cosmetic or pharmaceutical composition which comprises a cosmetically or pharmaceutically effective amount of at least one peptide of general formula (I), its stereoisomers, mixtures thereof and/or its cosmetically or pharmaceutically acceptable salts, according to claim 1, and at least one cosmetically or pharmaceutically acceptable excipient or agent.

9. The composition according to claim 8, wherein the peptide of general formula (I), its stereoisomers, mixtures thereof and/or its cosmetically or pharmaceutically acceptable salts, is incorporated into a cosmetic or pharmaceutical delivery system or sustained release system selected from the group consisting of liposomes, mixed liposomes, oleosomes, niosomes, ethosomes, millicapsules, microcapsules, nanocapsules, nanostructured lipid carriers, sponges, cyclodextrins, vesicles, micelles, mixed micelles of surfactants, surfactant-phospholipid mixed micelles, millispheres, microspheres, nanospheres, liposheres, microemulsions, nanoemulsions, miniparticles, milliparticles, microparticles, nanoparticles and solid lipid nanoparticles or is adsorbed on a cosmetically or pharmaceutically acceptable solid organic polymer or solid mineral support selected from the group consisting of talc, bentonite, silica, starch and maltodextrin.

10. The composition according to claim 8, wherein the peptide of general formula (I), its stereoisomers, mixtures thereof and/or its cosmetically or pharmaceutically acceptable salts is in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, soft capsules, hard capsules, tablets, sugar coated tablets, granules, chewing gum, solutions, suspensions, emulsions, syrups, elixirs, polysaccharide films, jellies, and gelatins.

11. The composition according to claim 8, wherein the peptide of general formula (I), its stereoisomers, mixtures thereof and/or its cosmetically or pharmaceutically acceptable salts is incorporated into a product selected from the group consisting of under-eye concealers, make-up foundation, make-up removing lotions, make-up removing milks, eye shadows, lipsticks, lip gloss, lip protectors and powders.

12. The composition according to claim 8, wherein the peptide of general formula (I), its stereoisomers, mixtures thereof and/or its cosmetically or pharmaceutically acceptable salts, is incorporated into a fabric, a non-woven fabric, or a medical device.

13. The composition according to claim 8, wherein the agent is selected from the group consisting of other agents which inhibit PAR-2 activity, other anti-inflammatory and/or analgesic agents, other anti-itching agents, calming agents, anesthetic agents, inhibitors of acetylcholine-receptor aggregation, agents inhibiting muscular contraction, anticholinergic agents, melanin synthesis stimulating or inhibiting agents, whitening or depigmenting agents, propigmenting agents, self-tanning agents, antiaging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances which retain moisture, alpha hydroxyacids, betahydroxy acids, moisturizers, hydrolytic epidermal enzymes, vitamins, amino acids, proteins, pigments or colorants, dyes, biopolymers, gelling polymers, thickening agents, surfactants, softening agents, emulsifiers, binding agents, preservatives, anti-wrinkle agents, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, aquaporin synthesis-stimulating agents, hyaluronic acid synthesis-stimulating agents, fibronectin synthesis-stimulating agents, sirtuin synthesis-stimulating agents, heat shock proteins, heat shock protein synthesis-stimulating agents, agents stimulating the synthesis of lipids and components of the stratum corneum, ceramides, fatty acids, agents that inhibit collagen degradation, agents inhibiting matrix metalloproteinase, agents that inhibit elastin degradation, agents that inhibit serine proteases such as cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, agents inhibiting acetylcholinesterase, skin relaxant agents, glycosaminoglycan synthesis-stimulating agents, anti-hyperkeratosis agents, comedolytic agents, anti-psoriatic agents, DNA repair agents, DNA protecting agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1α synthesis, agents modulating the activity of PPARγ, agents which increase or reduce the triglyceride content of adipocytes, anti-cellulite agents, antiperspirant agents, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, fragrances, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, and mixtures thereof.

14. A method for the inhibition of PAR-2 receptor activity, which comprises the administration of a cosmetically or pharmaceutically effective amount of at least one peptide of general formula (I) its stereoisomers, mixtures thereof and/or its cosmetically or pharmaceutically acceptable salts, according to claim 1.

15. A method for the treatment of itching, inflammation, pain, diseases and/or disorders of the respiratory airways, which comprises the administration of a cosmetically or pharmaceutically effective amount of at least one peptide of general formula (I) its stereoisomers, mixtures thereof and/or its cosmetically or pharmaceutically acceptable salts, according to claim 1.

16. A method for the treatment and/or care of the skin and/or mucous membranes, which comprises the administration of a cosmetically or pharmaceutically effective amount of at least one peptide of general formula (I) its stereoisomers, mixtures thereof and/or its cosmetically or pharmaceutically acceptable salts, according to claim 1.

17. The method according to claim 15, wherein the treatment and/or care stimulates and/or cares for the skin barrier function.

18. The method according to claim 15, wherein the treatment and/or care heals and/or reepithelizes the skin.

19. The method according to claim 15, wherein the treatment and/or care depigments and/or photoprotects the skin or treats and/or cares for those conditions, disorders and/or diseases of the skin which improve or are prevented by the reduction in the pigmentation of the skin or by the photoprotection of the skin.

20. The method according to claim 15, wherein the treatment and/or care is a treatment of the scalp and/or capillary hygiene.

21. The method according to claim 15, wherein the treatment and/or care is a treatment of oral mucosa and/or oral hygiene.

22. The method according to claim 15, wherein the treatment and/or care is a treatment of vaginal mucus and/or intimate hygiene.

23. The method according to claim 15, wherein the treatment and/or care is an inhibition of skin sensitizing agents.

24. The peptide of claim 1, when neither $R_1$ nor $R_2$ is an α-amino acid.

25. The peptide according to claim 2, wherein $R_2$ is —$NR_3R_4$ or —$OR_3$, wherein $R_3$ and $R_4$ are independently selected from the group consisting of H, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl with 3-10 ring members, and substituted or unsubstituted heteroarylalkyl of 2 to 24 carbon atoms and 1 to 3 atoms other than carbon and an alkyl chain of 1 to 6 carbon atoms.

* * * * *